United States Patent
Lee et al.

(10) Patent No.: US 12,240,830 B2
(45) Date of Patent: Mar. 4, 2025

(54) FUSED RING HETEROARYL COMPOUNDS AND USE THEREOF

(71) Applicant: BiSiChem Co., Ltd., Seongnam-si (KR)

(72) Inventors: Jinwoo Lee, Seongnam-si (KR); Byungnam Kang, Seongnam-si (KR); Youngdo Shin, Seongnam-si (KR); Namhee Kim, Seongnam-si (KR); Jungwoo Lee, Seongnam-si (KR); Hongjun Kang, Seongnam-si (KR); Sunjoo Kim, Seongnam-si (KR); Inho Yang, Seongnam-si (KR); Cheolhwan Yoon, Seongnam-si (KR); Cheolkyu Han, Seongnam-si (KR); Jeongbeob Seo, Seongnam-si (KR)

(73) Assignee: BiSiChem Co., Ltd., Seongnam-si (KR)

( * ) Notice: Subject to any disclaimer, the term of this patent is extended or adjusted under 35 U.S.C. 154(b) by 0 days.

(21) Appl. No.: 17/887,424

(22) Filed: Aug. 13, 2022

(65) Prior Publication Data
US 2023/0089180 A1    Mar. 23, 2023

Related U.S. Application Data

(60) Provisional application No. 63/232,808, filed on Aug. 13, 2021.

(51) Int. Cl.
| | |
|---|---|
| *C07D 401/14* | (2006.01) |
| *A61K 31/4439* | (2006.01) |
| *A61K 45/06* | (2006.01) |
| *C07D 471/04* | (2006.01) |

(52) U.S. Cl.
CPC ........ *C07D 401/14* (2013.01); *A61K 31/4439* (2013.01); *A61K 45/06* (2013.01); *C07D 471/04* (2013.01)

(58) Field of Classification Search
CPC .................................................. C07D 401/14
See application file for complete search history.

*Primary Examiner* — Brian E McDowell
(74) *Attorney, Agent, or Firm* — United One Law Group LLC; Kongsik Kim; Jhongwoo Peck

(57) ABSTRACT

The invention provides novel substituted heterocyclic compounds represented by Formula I, or a pharmaceutically acceptable salt, solvate, polymorph, ester, tautomer or prodrug thereof, and a composition comprising these compounds. The compounds provided can be used as inhibitors of ALK5 and are useful in the treatment of chronic fibrosis, vascular disorder, obesity, diabetes, autoimmune diseases and cancer.

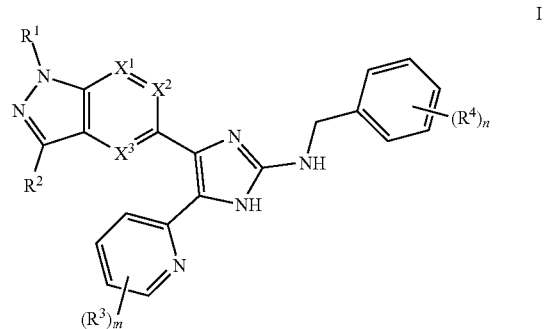

3 Claims, No Drawings

FUSED RING HETEROARYL COMPOUNDS AND USE THEREOF

CROSS-REFERENCE TO RELATED APPLICATION

This application claims priority to U.S. Application No. 63/232,808 filed on Aug. 13, 2021, which is incorporated herein by reference.

TECHNICAL FIELD

This invention relates to a series of substituted heterocyclic compounds which are inhibitors of the transforming growth factor-β (TGF-β) type I receptor (Activin Like Kinase5) and/or the activin type I receptor (ALK4) and are useful in the treatment of obesity, diabetes, glomerulonephritis, diabetic nephropathy, lupus nephritis, hypertension-induced nephropathy, renal interstitial fibrosis, renal fibrosis resulting from complications of drug exposure, HIV associated nephropathy, transplant nephropathy, liver fibrosis due to all etiologies, hepatic dysfunction attributable to infections, alcohol-induced hepatitis, NASH (non-alcoholic steatohepatitis), disorders of the biliary tree, pulmonary fibrosis, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, vascular stenosis, hypertension-induced vascular remodeling, pulmonary arterial hypertension, coronary restenosis, peripheral restenosis, carotid restenosis, stent-induced restenosis, atherosclerosis, ocular scarring, corneal scarring, proliferative vitreoretinopathy, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Peyronie's disease, Dupuytren's contracture, Alzheimer's disease, Raynaud's syndrome, fibrotic cancers, tumor metastasis growth, radiation-induced fibrosis, and thrombosis. This invention also relates to a pharmaceutical composition comprising the compound of the invention, use of the compound in the preparation of a medicament, and method of treatment for hyperproliferative diseases in mammals, especially humans by administering the compound thereof.

BACKGROUND ART

Transforming growth factor-β (TGF-β) is a ubiquitously expressed, a potent pleiotropic cytokine that maintains physiological homeostasis by regulating cellular processes such as apoptosis, proliferation and differentiation.

The TGF-β superfamily represents a diverse set of growth factors, which signal through receptor serine/threonine kinases. The superfamily is subdivided into two branches: the TGF-β/Activin branch and the Bone Morphogenetic Protein (BMP)/Growth and Differentiation Factor (GDF) branch. Each branch is further divided into subgroups based on sequence similarity. The TGF-β/Activin branch includes TGF-β, Activin, Inhibin, Nodal, and Lefty ligands. The BMP/GDF branch includes BMP, GDF, and Mullerian Inhibitory Substance (MIS) ligands. Almost all cells secrete TGF-β and express TGF-β receptors.

Upon binding of active TGF-β to the ALK5 and type II (TGF-βRII) receptor, ALK5 is phosphorylates and activates by TGF-βRII. ALK5, in turn, phosphorylates and activates the R-Smads, Smad2 and Smad3, which form a complex with Smad4. This complex translocates to the nucleus, which binds DNA in conjunction with other transcription factors and interacts with the general transcription machinery to regulate the expression of approximately 100-300 target genes.

Consistent with the many developmental defects that result from experimentally dysregulated TGF-β family signaling, moderate alterations in TGF-β family protein function have been linked to developmental syndromes and many diseases, including impaired wound healing, chronic fibrosis, vascular disorder, obesity, diabetes, autoimmune diseases and cancer.

TGF-β is heavily implicated in a variety of fibrous diseases (Border W A et al, N Engl J Med. 331(19):1286-1292 (1994)). Fibrosis occurs when there is an imbalance in extracellular matrix (ECM) deposition and degradation. Many TGF-β ligands are potent drivers of ECM deposition, and additionally, have natural affinity for the ECM, creating a concentrated pool of pro-fibrotic factors at the site of injury (Kelly L et al, Front in Pharm 8:461 (2017)). In response to injury, the influx of granulocytes, platelets, leukocytes, and additional parenchymal cells increase the presence of TGF-β at the site of the wound (Branton M H, et al, Microbes Infect. 1(15):1349-1365 (1999); Border W A et al, N Engl J Med. 331(19):1286-1292(1994)). TGF-β then induces fibroblast proliferation, myofibroblast differentiation, and remodeling of the extracellular matrix (Branton M H et al, Microbes Infect. 1(15):1349-1365 (1999); Border W A et al, N Engl J Med. 331(19):1286-1292(1994); Xiao L et al, Front Biosci. 17:2667-2674(2012); Roverts A B et al, Proc Natl Acad Sci USA. 83(12):4167-4171(1986)). Fibroblasts derived from hypertrophic scars have been shown to have an alteration in TGF-β signaling. Studies have indicated increased expression and phosphorylation of the Smads2 and/or 3 in hypertrophic scarring (Xie J L et al, Dermatol surg. 34(9):1216-1224 (2008); Kopp J et al, J Biol chem. 280(22):21570-6 (2005)). Activation of Smad2/3 regulates to the expression of several profibrotic genes, including collagens [COL1A1, COL3A1, COL5A2, COL6A1, COL6A3, COL7A1] (Verrecchia F et al, J Biol chem. 276, 17058-17062 (2001)), plsminnogen activator inhibitor-1 (PAI-1) (Dennler S et al, EMBO J. 17:3091-3100 (1998); Hua X et al, Genes Dev. 12:3084-3095 (1998)), various proteoglycans (Schonherr E et al, J Biol Chem. 266:17640-17647 (1991); Romaris M et al, Biochem J. 310:73-81 (1995); Dadlani H et al, J Biol chem. 283:7844-7852 (2008)), integrin (Margadant C et al, EMBO Rep. 11:97-105 (2010)), connective tissue growth factor (Chen Y et al, Kidney Int. 62:1149-1159 (2002)), and matrix metalloproteases (MMPs) (Yuan W et al, J Biol Chem. 276:38502-38510 (2001)). Therefore, Neutralization of TGF-β in animal models inhibits liver fibrosis and reduces the risk of developing cholangiocarcinoma (Fan X et al, PLoS One. 8(12):82190 (2013); Ling H et al, PLoS One. 8(1):e54499 (2013)). ALK5 inhibitor inhibits the transcription and deposition of extracellular matrix and improves the deterioration of liver function in mice (Gouville A C et al, Br J Pharmacol. 145(2):166-77 (2005)). Based on previous reports, TGF-β signaling would appear to be a potential target for the prevention or treatment of fibrotic diseases. Thus, direct inhibition of ALK5 represents an attractive way to prevent detrimental profibrotic effects of TGF-β. Recently described synthetic inhibitors of ALK5 have been shown to block TGF-β effects in cellular assays (Callahan J F et al, J Med Chem. 45:999-1001 (2002); Inman G et al, Mol Pharmacol. 62:65-74 (2002); Laping N et al, Mol Pharmacol. 62:58-64 (2002); Sawyer J S et al, J Med Chem. 46:3953-3956 (2003)).

Misregulation of TGF-β signaling lead to vascular dysfunction and disease, including hypertension (Cambien et al, Hypertension 28(5):881-887 (1996)), cardiac hypertrophy (Schultz et al, Clinical Inv. 109(6):787-796 (2002)) and cardiac fibrosis (Leask A, Cir Res. 106(11):1675-1680 (2010), Nikol S et al, Clinical Inv. 70(4):1582-1592 (1992)) and atherosclerosis (Harradine et al, Annals of Med. 38(6): 403-414 (2006), Bobik et al, Circulation 99(22):2883-2891 (1999)). TGF-β can have direct effects on vascular development and vessel remodeling and play key roles in atherosclerosis and restenosis, regulating endothelial cell (EC), smooth muscle cell (SMC), macrophage, T cell, and probably vascular calcifying cell response. The inhibition of TGF-β signaling by the ALK5 kinase inhibitor SB431542 increases permeability to maintain the EC barrier properties in retinal EC culture (Antonov A S et al, J Cell Physiol. 227(2):759-71 (2012)). SB431542 results in increased expression of the EC specific component Claudin-5 and inhibits expression of adhesion molecules (Watabe et al, J Cell Biol. 163(6):1303-11 (2003)). Systemic inhibition of TGF-β in adult mice led to increased vessel permeability as demonstrated by decreased association between the tight junction proteins ZO-1 and occludin (Walshe et al, Plos One 4(4):e5149 (2009)). EC treatment with SB431542 inhibited TGF-β-induced EC contraction by cytoskelectal remodeling (Birukova et al, FEBS letter 579(18):4031-37 (2005)). Also, SM16, an Orally Active ALK5 inhibitor, prevents the fibrotic hyperplastic vascular response in the rat carotid balloon injury model (Fu et al, Arteriosclerosis, Thrombosis, and Vascular Biology 28(4):665-671 (2008)). ALK5 inhibitor might be useful for therapeutic target in vascular disorder.

Recent findings on the role of TGF-β signaling via ALK5 in the pathogenesis of obesity and type 2 diabetes have underscored its importance in metabolism and adiposity. Indeed, elevated TGF-β has been previously reported in human adipose tissue during morbid obesity and diabetic neuropathy. In vivo findings on the role of TGF-β signaling in metabolism based on the studies using Smad3-knockout (Smad3$^{-/-}$) mice. TGF-β signaling via ALK5 regulates insulin gene transcription in the pancreatic islet β-cells (Lin H M et al, J Biol Chem. 284:12246-12257 (2009)), whereas Smad3 deficiency in mice protects against insulin resistance and type 2 diabetes during high-fat diet-induced obesity (Tan C K et al, Diabetes 60:464-476 (2011); Yadav H et al, Cell Metab. 14:67-79 (2011)). These Smad3$^{-/-}$ mice exhibited diminished adiposity with improved glucose tolerance and insulin sensitivity. These mutant mice also displayed increased β-oxidation in the adipose tissue upon administration of a high-fat diet, thus ameliorating gluco- and lipotoxicity in the pancreas, skeletal muscle and liver by preventing ectopic fat accumulation (Tan C K et al, Diabetes. 60:464-476 (2011)). Notably, when TGF-β signaling was blocks phosphorylation of Smad3 by treatment with a TGF-β neutralizing antibody, it protected the mice from obesity and type 2 diabetes (Yadav H et al, Cell Metab. 14:67-79 (2011)). Small molecule inhibitors of the TGF-β signaling via ALK5 promote β-cell replication in human islets transplanted into NOD-scid IL-2Rgnull mice (Dhawan S et al, Diabetes. 65(5):1208-1218 (2016)). These findings indicate that Smad3, the canonical intracellular mediator of TGF-β/ALK5, serves as a multifaceted regulator of metabolic homeostasis, thus identifying ALK5 mediated Smad3 phosphrylation as a potential target in the treatment of obesity and its associated disorders.

TGFβ1 is the predominant isoform in lymphoid organs (Schmid, P. et al, Development 111, 117 (1991)) TGFβ1 exerts powerful anti-inflammatory functions, and is a master regulator of the immune response (Li M O et al, Annu Rev Immunol 24:99-146 (2006)). However, its seemingly paradoxical role in exacerbating inflammatory responses and, thus, promoting autoimmunity in association with T helper 17 cells (Th17) was documented many years (Wahl, S. M, J. Exp. Med. 180, 1587-1590 (1994), Fava, R. A. et al, J. Exp. Med. 173, 1121-1132 (1991)). Activated TGF-β has both stimulatory T helper 17 (Th17) and regulatory T cells (Treg) influences on T cell function (Chen W et al, Cytokine Growth Factor Rev. 2003, 14: 85-89, Wahl S M et al, Immunol Res. 2003, 28: 167-179). Its essential role in driving the differentiation of Th17 cells, which are responsible for the pathology of autoimmune diseases such as rheumatoid arthritis or experimental autoimmune encephalomyelitis (EAE) (Cua, D. J. et al, Nature 421, 744-748 (2003), Nakae, S. et al, J. Immunol. 171, 6173-6177 (2003)). Recent studies indicate that Th17 cells and their upstream stimulator IL-23, or the IL-23/Th17 pathway, play crucial roles in the pathogenesis of several autoimmune diseases such as rheumatoid arthritis, inflammatory bowel disease and psoriasis (Di Cesare A et al, J Invest Dermatol. 2009; 129:1339-50, Annunziato F et al, Nat Rev Rheumatol. 2009:325-31, de Cid R et al, Nat Genetic. 2009; 41:211-5).

In rheumatoid arthritis (RA), TGF-β is expressed at high levels in RA patients (Lotz M et al, J. Immunol. 144:4189 (1990), Taketazu F et al, Lab. Investig. 70:620 (1994)). TGF-β1 contribute for the inflammation and destruction of joints in rheumatoid arthritis (RA) and osteoarthritis (OA). In a RA animal model, injections of TGF-β into the synovium induced an inflammatory response with accumulation of neutrophils, and exacerbated arthritic responses (Allen J B et al, J Exp Med. 171:231-47 (1990), Fava R A et al, J Exp Med. 173:1121-32 (1991)). TGF-β1 induced or increased the expressions of IL-1β, TNFα, IL-8, MIP-1α and MMP-1, and synergized with other proinflammatory cytokines in RA fibroblast-like synoviocytes (FLS). the pro-inflammatory effects of TGF-β1 were specific to arthritic FLS (Cheon H et al, Clin Exp Immunol 127:547-552 (2002)). In addition, TGF-β induced IL-6 and vascular endothelial growth factor (VEGF) production by RA synovial fibroblasts associated with nuclear factor-kappa B activation. These effects of TGF-β on RA synovial fibroblasts were inhibited by ALK5 kinase inhibitor HTS466284 (Michitomo S etl al, Int Immunol. 19(2):117-26 (2007)).

Overexpression of and/or defects in TGF-β signaling have been linked to many cancers, including lung, pancreatic, colon, prostate, and breast cancer (Eliott R L et al, J clin Oncol. 23:2078-2093 (2005)). Through these studies, it has become clear that TGF-β can function as both a tumor suppressor and a tumor promoter (Akhurst R J et al, Trends Cell Biol. 11(11):44-51 (2011)). In benign epithelia and many early-stage tumors, TGF-β is a potent inducer of growth arrest. However, in advanced tumors, TGF-β signaling pathways are severely dysregulated. Rather than inhibiting carcinogenesis, TGF-β promotes tumor growth and progression at late stages (Akhurst R J et al, Trends Cell Biol. 11(11):S44-51 (2011); Massague J et al, Cell. 134(2): 215-230 (2008); Padua D et al, Cell Res. 19(1):89-102 (2009); Inman G J et al, Curr Opin Genet Dev. 21(1):93-99 (2011); Pasche B et al, J Cell Physio.l 186(2):153-168 (2001); Langenskiold M et al, J Surg Oncol. 97(5):409-415 (2008)). This functional switch is known as the TGF-β paradox. There is also evidence that the tumor suppressor versus oncogenic effects of TGFβ are contextual and/or depend on the temporal stage of cellular transformation. For example, the expression of ALK5 mutant that is unable to bind Smad2/3 results in larger, more proliferative, less differentiated mammary tumors. However, expression of the same mutant in highly malignant mammary cells suppresses their ability to metastasize to the lungs (Tian F et al, Cancer Res. 64:4523-30 (2004)).

The pluripotent nature of TGF-β provides both opportunities and challenges to neutralize its effects. However, many cancers often become refractory to this growth inhibition either due to genetic loss of TGF-β signaling components or, more commonly, because of downstream perturbation by other integrated signaling pathways. During this time, the protumorigenic actions of TGF-β may prevail, including immunomodulatory properties, induction of angiogenesis and/or promotion of the epithelial-to-mesenchymal transition (EMT) facilitating cancer migration and invasion.

TGF-β has an adverse effect on anti-tumor immunity and significantly inhibits host tumor immune surveillance. TGF-β plays a crucial role in the repression of the immune system, as attested by the gross autoimmunity developed in TGF-β1 null mice (Shull M M et al, Nature. 359(6397): 693-699 (1992)). Interestingly, this T-cell-specific blockade of TGF-β signaling allows the generation of tumor-specific cytotoxic T lymphocytes (CTLs) that are capable of eradicating tumors in mice challenged with EL-4 thymoma or B16-F10 melanoma tumor cells (Thomas D A et al, Cancer Cell. 8(5):369-380 (2005)). Oral treatment with selective ALK5 inhibitor, TEW-7197 and LY-2157299 suppressed the progression of melanoma with enhanced cytotoxic T-lymphocyte (CTL) activity. Notably, anti-tumor effect of the ALK5 inhibition mainly depends on CD8+ T cells (Yoon J H et al, EMBO Mol Meld. 5(11):1720-1739 (2013)). TGF-β also has a significant impact on CD4+ T-cell differentiation and function and inhibits NK-cell proliferation and function, which is in part modulated by CD4+CD25+ regulatory T cells that are known to produce high levels of TGF-β (Nakamura et al, J Exp Med. 194(5):629-644 (2001); Ghiringhelli F et al, J Exp Med. 202(8):1075-1085 (2005); Shevach E M et al, Immunity. 30(5):636-645 2009)). Genetic deletion and antibody neutralization studies have demonstrated that TGFβ inhibition enhances T cell and NK cell differentiation and function (Mo et al, Immunity 25(3): 455-471 (2006), Zhong et al, Clin Can Res 16(4):1191-1205 (2010)). TGF-β produced by tumor cells induces immunosuppression via expansion of CD4+CD25+ regulatory T regulatory cells (Tregs) (Bierie et al, Nat Rev Cancer 6(7): 506-20 (2006)). Systemic blockade of ALK5 enhences homeostatic proliferation and induces a population of Tregs cells in in vitro and vivo (Polanczyk et al, J Trnas Med 17(219) (2019)). In the immunotherapy of neuroblastoma, Galunisertib (LY2157299 monohydrate), a small-molecule inhibitor of ALK5 in combination with dinutuximab (anti-GD2 antibody) enhances the anti-neuroblastoma effect of dinutuximab with adoptively transferred activated NK cells (Tran et al, Clin Cancer Res. 23(3):804-813 (2017).

A prior study suggested the roles of TGF-β signaling in angiogenesis. Inhibiting TGF-β signaling through ALK5 results in increased endothelial cell (EC) migration and proliferation, which are further enhanced in the presence of vascular endothelial growth factor (VEGF) (Liu Z et al, J Cell Sci. 122:3294-3302 (2009)). ECs have been reported to express two distinct ALK5 and ALK1. The importance of these two receptors in mediating vessel development by TGF-β is evidenced by the embryonic lethality observed at day E11.5 and E10.5 in mice lacking ALK1 (Oh S P et al, Proc Natl Sci USA. 97:2626-2631 (2000)) or ALK5 (Larsson J et al, EMBO J. 20:1663-1673 (2001)), respectively. The canonical SMAD2/3 pathway is activated by ALK5, inducing the expression of PAI-1 and fibronectin, thereby impeding angiogenesis (Goumans M J et al, Mol Cell. 12:817-828 (2003); Goumans M J et al, EMBO J. 21:1743-1753 (2002); Wu X et al, Microvasc Res. 71:12-19 (2006); Ota T et al, J Cell Physiol. 193:299-318 (2002); Safina A et al, Oncogene 26(17):2407-22 (2007)). Many of the cancer-promoting functions of TGF-β are exerted via the cooperation between TGF-β and transforming oncogenes, such as ErbB2/HER2/Neu, polyomavirus middle T antigen (PyVmT) and Ras. VEGF, a target of the TGF-β-Smad transcriptional regulation significantly was up-regulated in mutant HER2. Thus, Inhibition of TGF-β signaling by LY2109761, a TGF-β receptor inhibitor, blocked cancer cell growth and tumor-induced angiogenesis (Wang et al, Oncogene 29(23):3335-48 (2010)).

TGF-β is known to regulate EMT (Epithelial-to-mesenchymal transition) and stemness of tumor cells. EMT is marked by the loss of E-cadherin and the expression of mesenchymal proteins such as vimentin, fibronectin, and N-cadherin, facilitating the invasion process and worsening prognosis. In cancer cells, the repression of E-cadherin and the induction of vimentin, matrix-metalloproteinases (MMPs), and other pro-EMT factors can be drive by TGF-β (Lee J M et al, J Cell Biol. 172(7):973-981 (2006); Zhao Y et al, Cell Biochem Funct. 26(5):571-577 (2008)). Inhibition of ALK5 attenuates the pro-oncogenic functions of TGF-β including cell migration, invasion, VEGF secretion, and EMT in human cancer cells (Halder et al, Neoplasia 7(5): 509-521 (2005)). CTI-82, a novel ALK5 inhibitor of EMT induced by TGF-β1, inhibits the mRNA and protein levels of various EMT markers (Jeong et al, Biology 9(7):143 (2020). Vactosertib (TEW-7197) reduced metastatic properties of human breast cancer cells via TGF-β- or radiation induced EMT and breast cancer stem cell (Park et al, Eur J Cancer 47(17):2642-53 (2011), Choi et al, Radiol Oncol 56(2):185-197 (2022)).

The extensive knowledge surrounding TGF-β-mediated, ALK5-dependent signaling and Smad2/Smad3 phosphorylation as a proximal event at the heteromeric receptor complex has focused initial drug discovery efforts on the type I receptor kinase as a therapeutic target (Laping N J et al, Curr Opin Pharm. 3:204-208 (2003); Singh J et al, Curr Opin Drug Disc Dev. 7:437-445 (2004)). SB-505124, a competitive inhibitor of the ATP-binding site of ALK5, diminishes growth in KRAS-driven pancreatic cancer cells that lack Rb (Gore et al, J Cli Invest. 124(1):338-352 (2014)). Galunisertib (LY2157299) and Vactosertib, are currently undergoing clinical trials in cancer treatment through clinical pharmacokinetic and pharmacodynamic studies. Galunisertib, an oral small molecule inhibitor of the ALK5 that specifically downregulates the phosphorylation of Smad2, abrogating activation of the canonical pathway. Galunisertib is currently in early clinical trials for the treatment of advanced, metastatic cancers. (Herbertz et al, Drug Des Devel Ther. 10(9):4479-4499 (2015)). Galunisertib is being investigated in either as monotherapy or in combination with standard antitumor regimens (including nivolumab) in patients with cancer with high unmet medical needs such as glioblastoma, pancreatic cancer, and hepatocellular carcinoma (NCT01746004, NCT01965808, NCT01582269, NCT01722825, NCT02008318, NCT01220271, NCT01246986, NCT01373164, NCT01682187). Vactosertib, a small molecule inhibitor of ALK5 for anticancer therapy, suppresses tumor growth in ALK5-overexpressing tumor cell types (Lee ho-jae, J Cancer Prev, 25(4): 213-222(2020)), Non-small cell lung carcinoma, bladder urothelial carcinoma, and malignant solid tumor being investigated in vactosertib clinical trials (NCT04103645, NCT03724851, NCT03732274, NCT03698825, NCT03074006, NCT03143985, NCT03802084, NCT04064190, NCT04515979, NCT04258072).

SUMMARY

This invention provides a compound of formula I, or a pharmaceutically acceptable salt, solvate, polymorph, ester, tautomer or prodrug thereof:

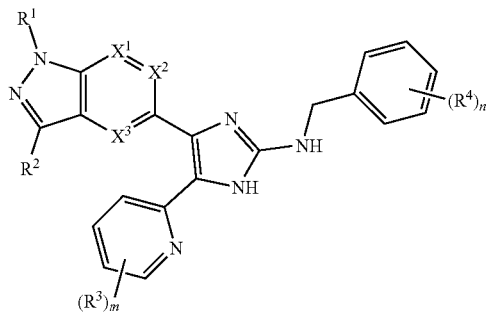

wherein
$R^1$ is H C1-C6 alkyl, $CD_3$, $CHF_2$, $CF_3$, —(C1-C6)hydroxyalkyl, or —$SO_2$alkyl;
$R^2$ is H, Me, $CF_3$, $NO_2$, halogen, acyl, C1-C6alkyl, substituted C1-C6alkyl, C1-C6haloalkyl, C3-C7cycloalkyl, alkylcarboxy, cyano, or alkoxy;
$X^1$, $X^2$ and $X^3$ are each independently CH or N;
each $R^3$ is independently selected from the group consisting of hydrogen, halogen, $CF_3$, acyl, amino, substituted amino, C1-C6alkyl, substituted C1-C6alkyl, C1-C6haloalkyl, C3-C7cycloalkyl, alkylcarboxy, cyano, nitro, or alkoxy;
each $R^4$ is independently selected from the group consisting of hydrogen, halogen, $CF_3$, acyl, amino, substituted amino, C1-C6alkyl, substituted C1-C6alkyl, C1-C6haloalkyl, cyano, nitro, alkoxy, acyloxy, or aryloxy;
m is 1, 2, 3 or 4;
n is 1, 2, 3, 4 or 5;

Compounds of Formula I further include the absolute configuration compounds of Formula II.

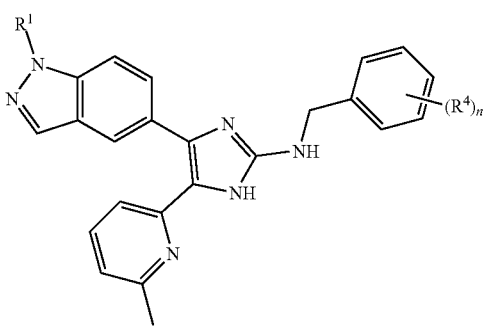

or salt thereof, wherein;
$R^1$ is H C1-C6 alkyl, $CD_3$, $CHF_2$, $CF_3$, —(C1-C6)hydroxyalkyl, or —$SO_2$alkyl;
each $R^4$ is independently selected from the group consisting of hydrogen, halogen, $CF_3$, acyl, amino, substituted amino, C1-C6alkyl, substituted C1-C6alkyl, C1-C6haloalkyl, cyano, nitro, alkoxy, acyloxy, or aryloxy;
n is 1, 2, 3, 4 or 5;

Compounds of present invention are inhibitors of the transforming growth factor-β (TGF-β) type I receptor (ALK5) and/or the activin type I receptor (ALK4) and, consequently, are useful for treating pulmonary fibrosis, obesity, diabetes, NASH (non-alcoholic steatohepatitis), cancers and other inflammation.

In other aspects, the present invention is directed to a pharmaceutical composition comprising an effective amount of a compound of formula I or a pharmaceutically acceptable salt, solvate, polymorph, ester, tautomer or prodrug thereof. In some embodiments, the pharmaceutical composition further comprises a pharmaceutically acceptable carrier, adjuvants and/or excipients. In some embodiments, such a composition may contain at least one of preservatives, agents for delaying absorption, fillers, binders, adsorbents, buffers, disintegrating agents, solubilizing agents, and other carriers, adjuvants and/or excipients as inert ingredients. The composition may be formulated with a method well-known in the art.

In some aspects, the present invention is directed to a method of treating a disease in an individual suffering from said disease comprising administering to said individual a therapeutically effective amount of a composition comprising a compound of formula I or a pharmaceutically acceptable salt, solvate, polymorph, ester, tautomer or prodrug thereof.

In other aspects, the present invention is directed to a method of treating a disorder in a mammal, comprising administering to said mammal a therapeutically effective amount of a compound of formula I or a pharmaceutically acceptable salt, solvate, polymorph, ester, tautomer or prodrug thereof.

In other aspects, the present invention is directed to a method of treating a disorder in a human, comprising administering to said human a therapeutically effective amount of a compound of formula I or a pharmaceutically acceptable salt, solvate, polymorph, ester, tautomer or prodrug thereof.

In other aspects, the present invention is directed to a method of treating an obesity, diabetes, NASH (non-alcoholic steatohepatitis), cancer, liver fibrosis due to all etiologies, renal interstitial fibrosis, pulmonary fibrosis, inflammation, certain infectious diseases, condition, or disorder in a mammal, including a human, comprising administering to said mammal a therapeutically effective amount of a compound of formula I, or a pharmaceutically acceptable salt, ester, prodrug, solvate, such as hydrate, polymorph or tautomer thereof.

In other aspects, the present invention is directed to a method of treating a disorder or condition which is modulated by the transforming growth factor-β (TGF-β) type I receptor (ALK5) and/or the activin type I receptor (ALK4) cascade in a mammal, including a human, comprising administering to said mammal an amount of the compound of formula I, or a pharmaceutically acceptable salt, ester, prodrug, solvate, such as hydrate, polymorph or tautomer thereof, effective to modulate said cascade. The appropriate dosage for a particular patient can be determined, according to known methods, by those skilled in the art.

In other aspects, the present invention is directed to use of compound of formula I or a pharmaceutically acceptable salt, ester, prodrug, solvate, such as hydrate, polymorph or tautomer thereof in the preparation of a pharmaceutical composition. The pharmaceutical composition can be used for treating a disorder or condition which is modulated by the ALK cascade in a mammal, including a human. The pharmaceutical composition is useful for treating pulmonary fibrosis, obesity, diabetes, cancers and other inflammation.

In other aspects, the present invention is directed to a pharmaceutical composition comprising a compound of formula I or a pharmaceutically acceptable salt, solvate, polymorph, ester, tautomer or prodrug thereof. In some embodiments, the pharmaceutical composition is in a form suitable for oral administration. In further or additional embodiments, the pharmaceutical composition is in the form of a tablet, capsule, pill, powder, sustained release formulation, solution and suspension. In some embodiments, the pharmaceutical composition is in a form suitable for parenteral injection, such as a sterile solution, suspension or emulsion; for topical administration as an ointment or cream or for rectal administration as a suppository. In further or additional embodiments, the pharmaceutical composition is in unit dosage forms suitable for single administration of precise dosages. In further or additional embodiments, the amount of compound of formula I is in the range of about 0.001 to about 1000 mg/kg body weight/day. In further or additional embodiments, the amount of compound of formula I is in the range of about 0.5 to about 50 mg/kg body weight/day.

In other aspects, the present invention is directed to a process for preparing a compound of formula I or a pharmaceutically acceptable salt, solvate, polymorph, ester, tautomer or prodrug thereof.

DETAILED DESCRIPTION

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein such embodiments are provided by way of example only. It should be understood that various alternatives to the embodiments of the invention described herein may be employed in practicing the invention. Those ordinary skilled in the art will appreciate that numerous variations, changes, and substitutions are possible without departing from the invention. It is intended that the following claims define the scope of aspects of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context dearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 47$^{TH}$ED." Vols A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art Standard techniques can be used for chemical syntheses, chemical analyses, pharmaceutical preparation, formulation, and delivery, and treatment of patients. Reactions and purification techniques can be performed e.g., using kits of manufacturers specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

Unless otherwise noted, the use of general chemical terms, such as though not limited to "alkyl," "amine," "aryl," are equivalent to their optionally substituted forms. For example, "alkyl," as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis)

configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Techniques for inverting or leaving unchanged a particular stereocenter, and those for resolving mixtures of stereoisomers are well known in the art and it is well within the ability of one of skill in the art to choose an appropriate method for a particular situation. See, for example, Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, Acc. Chem. Res. 1990, 23, 128.

The term "bond" or "single bond" refers to a chemical bond between two atoms, or two moieties when the atoms joined by the bond are considered to be part of larger substructure.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., $CH_2CH_3$), fully substituted (e.g., $CF_2CF_3$), mono-substituted (e.g., $CH_2CH_2F$) or substituted at a level anywhere in-between fully substituted and mono-substituted (e.g., $CH_2CHF_2$, $CF_2CH_3$, $CFHCHF_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, $C_1$-Cn, includes $C_1$-$C_2$, $C_1$-$C_3$, . . . $C_1$-Cn. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, isobutyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The terms "heteroatom" or "hetero" as used herein, alone or in combination, refer to an atom other than carbon and hydrogen. Heteroatoms are independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl).

A non-limiting example of "cycloalkyl" includes azinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo [4.1.0]heptyl, 3H-indolyl and quinolizinyl and the like. The terms also include all ring forms of the carbohydrates, including but not limited to the monosaccharides, the disaccharides and the oligosaccharides.

The term "aromatic" as used herein, refers to a planar, cyclic or polycyclic, ring moiety having a delocalized at-electron system containing 4n+2 electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

Certain Pharmaceutical Terminology

The term "ALK inhibitor" as used herein refers to a compound that exhibits an $IC_{50}$, with respect to ALK activity, of no more than about 100 µM or not more than about 50 µM, as measured in the kinase assay described generally herein. "$IC_{50}$" is that concentration of inhibitor which reduces the activity of an enzyme to half-maximal level. Compounds described herein have been discovered to exhibit inhibition against ALK. Compounds of the present invention preferably exhibit an $IC_{50}$ with respect to ALK of no more than about 10 µM, more preferably, no more than about 5 µM, even more preferably not more than about 1 µM, and most preferably, not more than about 200 nM, as measured in the kinase assay described herein.

The term "selective," "selectively," or "selectivity" as used herein refers to a compound of this invention having a lower $IC_{50}$ value for the enzyme as compared to any other enzymes (e.g., at least 2, 5, 10 or more-fold lower).

The term "subject", "patient" or "individual" as used herein in reference to individuals suffering from a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer," "administering", "administration," and the like, as used herein, refer to the methods that may be used to enable delivery of compounds or compositions to the desired site of biological action. These methods include, but are not limited to, oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed. Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caprylate, chlorobenzoate, chloride, citrate, cyclopentanepropionate, decanoate, digluconate, dihydrogenphosphate, dinitrobenzoate, dodecylsulfate, ehanesulfonate, formate, fumarate, glucoheptanoate, glycerophosphate, glycolate, hemisulfate, heptanoate, hexanoate, hexyne-1,6-dioate, hydroxybenzoate, hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts (See examples at Berge et al., *J. Pharm. Sci.* 1977, 66, 1-19). Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge et al., supra.

The term "solvate" as used herein refers to a combination of a compound of this invention with a solvent molecule formed by solvation. In some situations, the solvate refers to a hydrate, i.e., the solvent molecule is a water molecule, the combination of a compound of this invention and water forms a hydrate.

The term "polymorph" or "polymorphism" as used herein refers to a compound of this invention present in different crystal lattice forms.

The term "ester" as used herein refers to a derivative of a compound of this invention derived from an oxoacid group and a hydroxyl group, either one of which can be present at the compound of this invention.

The term "tautomer" as used herein refers to an isomer readily interconverted from a compound of this invention by e.g., migration of a hydrogen atom or proton.

The term "pharmaceutically acceptable derivative or prodrug" as used herein, refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example *Design of Produgs*, Bundgaard, A. Ed., Elseview, 1985 and *Method in Enzymology*, Widder, K. et al., Ed.; Academic, 1985, vol. 42, p. 309-396; Bundgaard, H. "Design and Application of Prodrugs" in *A Textbook of Drug Design and Development*, Krosgaard-Larsen and H. Bundgaard, Ed., 1991, Chapter 5, p. 113-191; and Bundgaard, H., *Advanced Drug Delivery Review*, 1992, 8, 1-38, each of which is incorporated herein by reference. The prodrugs described herein include, but are not limited to, the following groups and combinations of these groups; amine derived prodrugs: Hydroxy prodrugs include, but are not limited to acyloxyalkyl esters, alkoxycarbonyloxyalkyl esters, alkyl esters, aryl esters and disulfide containing esters.

The terms "enhance" or "enhancing," as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from mixing or combining more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present Thus, in some embodiments, the compounds of the invention and the other agent(s) are administered in a single composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996).

Experimental Part

NMR spectra were recorded in $CDCl_3$, $DMSO-d_6$ or $CD_3OD$ solution in 5-mm o.d. tubes (Norell, Inc. 507-HP) at 30° C. and were collected on Varian VNMRS-400 at 400 MHz for $^1H$. The chemical shifts (δ) are relative to tetramethylsilane (TMS=0.00 ppm) and expressed in ppm. LC/MS was taken on Ion-trap Mass Spectrometer on FINNIGAN Thermo or ISQ EC, Thermo Fisher U3000 RSLC (Column: YMC Hydrosphere (C18, Ø4.6×50 mm, 3 μm, 120 Å, 40° C.) operating in ESI(+) ionization mode; flow rate=1.0 mL/min. Mobile phase=0.01% heptafluorobutyric acid (HFBA) and 1.0% isopropyl alcohol (IPA) in water or $CH_3CN$.

Intermediate 1: 5-bromo-1-(tetrahydro-2H-pyran-2-yl)-1H-indazole

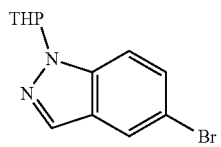

To a solution of 5-bromo-1H-indazole (1.00 g, 5.08 mmol) in DCM (20 mL) was added 3,4-dihydro-2H-pyran (1.35 mL, 14.7 mmol) and p-TsOH—$H_2O$ (0.193 g, 1.02 mmol) at room temperature. The reaction mixture was stirred at temperature for 3 hours and then concentrated in vacuo. The residue was diluted with EtOAc, washed with saturated aq. $NaHCO_3$ and brine, dried over $Na_2SO_4$, filtered, and concentrated in vacuo. The residue was purified by column chromatography on $SiO_2$ (Hexane:EtOAc=9:1) to give 5-bromo-1-(tetrahydro-2H-pyran-2-yl)-1H-indazole (1.30 g, 91%). $^1$H-NMR (400 MHz, DMSO-$d_6$): δ 8.10 (1H, s), 8.02 (1H, d, J=2 Hz), 7.73 (1H, d, J=9.2 Hz), 7.53 (1H, dd, J=9.2, 2.0 Hz), 5.86 (1H, dd, J=2.8, 2.0 Hz), 3.88-3.70 (2H, m), 2.05-1.93 (2H, m), 1.77-1.47 (4H, m).

Intermediate 2: 5-bromo-3-fluoro-1-(tetrahydro-2H-pyran-2-yl)-1H-indazole

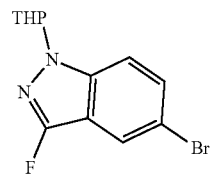

Step A: 5-bromo-3-fluoro-1H-indazole

To a solution of 5-bromo-1H-indazole (500 mg, 2.54 mmol) in MeCN (10 mL) was added dropwise a solution of Selectfluor (899 mg, 2.54 mmol) in MeCN (5.0 mL) at room temperature. The reaction mixture was refluxed for 16 hours and then concentrated in vacuo. The residue was diluted with EtOAc and washed with saturated aq. $NaHCO_3$ and brine, dried over $Na_2SO_4$, filtered and concentrated in vacuo. The residue was purified by column chromatography on $SiO_2$ (Hexane:EtOAc=8:1 to 3:1) to give 5-bromo-3-fluoro-1H-indazole (222 mg, 41%) as a yellow solid. $^1$H-NMR (400 MHz, DMSO-$d_6$): δ 7.97 (1H, d, J=1.6 Hz), 7.57-7.53 (1H, m), 7.49-7.46 (1H, m).

Step B: 5-bromo-3-fluoro-1-(tetrahydro-2H-pyran-2-yl)-1H-indazole

To a mixture solution of 5-bromo-3-fluoro-1H-indazole (222 mg, 1.03 mmol) and p-TsOH·$H_2O$ (39.0 mg, 0.206 mmol) in DCM (60 mL) was added 3,4-dihydro-2H-pyran (0.270 mL, 2.95 mmol) at room temperature. The reaction mixture was stirred at room temperature for 15 hours and then concentrated in vacuo. The residue was diluted with EtOAc, washed with saturated aq. $NaHCO_3$ and brine, dried over $Na_2SO_4$, filtered and concentrated in vacuo. The residue was purified by column chromatography on $SiO_2$ (Hexane:EtOAc=9:1) to give 5-bromo-3-fluoro-1-(tetrahydro-2H-pyran-2-yl)-1H-indazole (255 mg, 83%) as a yellow oil. $^1$H-NMR (400 MHz, $CDCl_3$): δ 7.77 (0l, s), 7.47-7.39 (2H, m), 5.55 (1H, s), 3.97 (1H, s), 3.70 (1H, s), 2.42 (1H, s), 2.07 (2H, d, J=31.6 Hz), 1.70 (3H, s).

Intermediate 3: 5-bromo-3-chloro-1-(tetrahydro-2H-pyran-2-yl)-1H-indazole

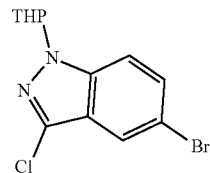

Step A: 5-bromo-3-chloro-1H-indazole

To a solution of 5-bromo-1H-indazole (500 mg, 2.54 mmol) in MeCN (18 mL) was added N-chlorosuccinimide (373 mg, 2.79 mmol) at room temperature. The reaction mixture was heated at 60° C. for 15 hours and then concentrated in vacuo. The residue was diluted with EtOAc, washed with 1 N aq. NaOH solution and brine, dried over $Na_2SO_4$, filtered and concentrated in vacuo to give 5-bromo-3-chloro-1H-indazole (528 mg, 90%) as a pale yellow solid. $^1$H-NMR (400 MHz, DMSO-$d_6$): δ 7.88 (11H, t, J=1.2 Hz), 7.56 (2H, d, J=0.8 Hz).

Step B: 5-bromo-3-chloro-1-(tetrahydro-2H-pyran-2-yl)-1H-indazole

To a solution of 5-bromo-3-chloro-1H-indazole 5-bromo-3-chloro-1H-indazole (592 mg, 2.56 mmol) and p-TsOH·$H_2O$ (97.0 mg, 0.511 mmol) in DCM (10 mL) was added 3,4-dihydro-2H-pyran (0.680 mL, 7.44 mmol) at room temperature. The reaction mixture was stirred at room temperature for 15 hours and then concentrated in vacuo. The residue was diluted with EtOAc, washed with saturated aq. $NaHCO_3$ and brine, dried over $Na_2SO_4$, filtered and concentrated in vacuo. The residue was purified by column chromatography on $SiO_2$ (Hexane:EtOAc=9:1) to give 5-bromo-3-chloro-1-(tetrahydro-2H-pyran-2-yl)-1H-indazole (760 mg, 94%) as a yellow oil. $^1$H-NMR (400 MHz, CDCl$_3$): δ 7.69 (1H, s), 7.39-7.33 (2H, m), 5.53 (1H, dd, J=2.4, 2.4 Hz), 3.90 (1H, d, J=11.6 Hz), 3.66-3.61 (1H, m), 2.44-2.35 (1H, m), 2.06-1.97 (2H, m), 1.70-1.58 (3H, m).

Intermediate 4: 5-bromo-3-nitro-1-(tetrahydro-2H-pyran-2-yl)-1H-indazole

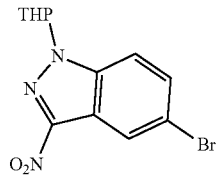

Step A: 5-bromo-3-nitro-1H-indazole

To a stirred suspension of 5-bromo-1H-indazole (500 mg, 2.54 mmol) in conc. $H_2SO_4$ (2.50 mL) was added dropwise a mixture of $HNO_3$ and $H_2SO_4$ (v/v=1:1, 2.5 mL) at 0° C. The reaction mixture was stirred at 0° C. for 30 minutes and poured onto ice-water. The mixture was stirred for further 10 minutes. A precipitated solid was collected by filtration, washed with water and dried under vacuum to give 5-bromo-3-nitro-1H-indazole (577 mg, 94%) as a white solid. $^1$H-NMR (400 MHz, DMSO-$d_6$): δ 8.28 (11H, s), 7.88-7.86 (11H, m), 7.77 (1H, d, J=8.8 Hz).

Step B: 5-bromo-3-nitro-1-(tetrahydro-2H-pyran-2-yl)-1H-indazole

To a solution of 5-bromo-3-nitro-1H-indazole 5-bromo-3-nitro-1H-indazole (577 mg, 2.38 mmol) and p-TsOH·$H_2O$ (91.0 mg, 0.477 mmol) in DCM (9.5 mL) was added 3,4-dihydro-2H-pyran (0.630 mL, 6.88 mmol) at room temperature. The reaction mixture was stirred at room temperature for 15 hours and then concentrated in vacuo. The residue was diluted with EtOAc, washed with saturated aq. $NaHCO_3$ and brine, dried over $Na_2SO_4$, filtered and concentrated in vacuo. The residue was purified by column chromatography on $SiO_2$ (Hexane:EtOAc=9:1) to give 5-bromo-3-nitro-1-(tetrahydro-2H-pyran-2-yl)-1H-indazole (724 mg, 93%) as a yellow oil. $^1$H-NMR (400 MHz, CDCl$_3$): δ 8.32 (1H, s), 8.09 (1H, dd, J=1.2, 0.8 Hz), 7.87 (1H, d, J=8.4 Hz), 6.00 (1H, dd, J=2.8, 2.4 Hz), 4.05-3.74 (2H, m), 2.40-2.31 (1H, m), 2.06-2.01 (2H, m), 1.77-1.56 (3H, m).

Intermediate 5: 3,5-dibromo-1-(tetrahydro-2H-pyran-2-yl)-1H-indazole

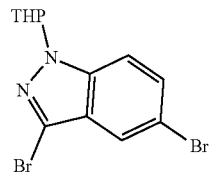

Step A: 3,5-dibromo-1H-indazole

To a solution of 5-bromo-1H-indazole (500 mg, 2.54 mmol) in DCM (25 mL) was added N-bromosuccinimide (465 mg, 2.61 mmol) at room temperature. The reaction mixture was stirred at room temperature for 15 hours and then concentrated in vacuo. The residue was dissolved in EtOAc, washed with saturated aq. $NaHCO_3$ and brine, dried over $Na_2SO_4$, filtered, and concentrated in vacuo to give 3,5-dibromo-1H-indazole (440 mg, 63%) as a pale yellow solid. $^1$H-NMR (400 MHz, CDCl$_3$): δ 7.77 (1H, d, J=2.0 Hz), 7.48 (1H, dd, J=8.8, 1.2 Hz), 7.34 (1H, d, J=9.2 Hz).

Step B: 3,5-dibromo-1-(tetrahydro-2H-pyran-2-yl)-1H-indazole

To a solution of 3,5-dibromo-1H-indazole (440 mg, 1.59 mmol) in DCM (9.0 mL) was added 3,4-dihydro-2H-pyran (0.450 mL, 4.93 mmol) followed by p-TsOH—$H_2O$ (61.0 mg, 0.319 mmol) at room temperature. The reaction mixture was stirred at room temperature for 15 hours and then concentrated in vacuo. The residue was diluted with EtOAc and washed with water and brine, dried over $Na_2SO_4$, filtered, and concentrated in vacuo. The residue was purified by column chromatography on NH—$SiO_2$ (Hexane:EtOAc=5:1 to 1:1) to give 3,5-dibromo-1-(tetrahydro-2H-pyran-2-yl)-1H-indazole (500 mg, 87%) as a viscous yellow oil. $^1$H-NMR (400 MHz, CDCl$_3$): δ 7.76 (1H, dd, J=2.0, 0.80 Hz), 7.52-7.46 (2H, m), 5.65 (1H, dd, J=9.2, 2.8 Hz), 4.00-3.96 (1H, m), 3.75-3.68 (1H, m), 2.55-2.45 (1H, m), 2.17-2.05 (2H, m), 1.79-1.64 (3H, m).

Intermediate 6: 5-bromo-1-methyl-1H-indazole

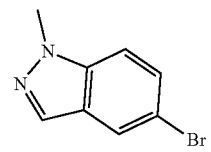

To a solution of 5-bromo-1H-indazole (2.00 g, 10.2 mmol) in DMF (28 mL) was added Cs$_2$CO$_3$ (6.61 g, 20.3 mmol) at room temperature. The mixture was stirred at room temperature for 30 minutes. After addition of MeI (0.740 mL, 11.9 mmol), the reaction mixture was stirred at room temperature for 2 hours. After addition of water, the mixture was extracted with EtOAc twice. The combined organic layers were washed with brine, dried over Na$_2$SO$_4$, filtered and concentrated in vacuo. The mixture was purified by column chromatography on SiO$_2$ (Hexane:EtOAc=4:1) to give 5-bromo-1-methyl-1H-indazole (1.43 g, 66%) as an orange solid. $^1$H-NMR (400 MHz, DMSO-d$_6$): δ 8.02 (1H, d, J=0.8 Hz), 7.99 (1H, d, J=2.0 Hz), 7.64 (1H, d, J=8.8 Hz), 7.50 (1H, dd, J=8.8, 2.0 Hz), 4.04 (3H, s).

Intermediate 7: 5-bromo-1-ethyl-1H-indazole

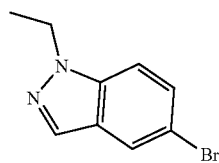

To a solution of 5-bromo-1H-indazole (2.00 g, 10.15 mmol) in THF (60.0 mL, 30 mL/g) was added NaH (60% dispersion in mineral oil, 395 mg, 16.4 mmol) at 0° C. The mixture was stirred at room temperature for 30 minutes. After addition of MeI (1.80 mL, 22.3 mmol) at 0° C., the reaction mixture was stirred at room temperature for 2 hours. After quenched with saturated aq. NH$_4$Cl, the mixture was extracted with EtOAc twice. The combined organic layers were washed with brine, dried over Na$_2$SO$_4$, filtered and concentrated in vacuo. The residue was purified by column chromatography on SiO$_2$ (Hexane:EtOAc=5:1) to give 5-bromo-1-ethyl-1H-indazole (1.09 g, 47%) as a yellow oil. $^1$H-NMR (400 MHz, CDCl$_3$): δ 7.92 (1H, d, J=0.8 Hz), 7.86 (1H, d, J=2.0 Hz), 7.44 (1H, dd, J=9.2, 1.6 Hz), 7.30 (1H, d, J=8.4 Hz), 4.41 (2H, q, J=7.6 Hz), 1.50 (3H, t, J=7.6 Hz).

Intermediate 8:
5-bromo-1-(difluoromethyl)-1H-indazole

To a solution of 5-bromo-1H-indazole (500 mg, 2.54 mmol) in MeCN (19.0 mL) was added KF (295 mg, 5.08 mmol) at room temperature. The mixture was stirred for 30 minutes. After addition of diethyl (bromodifluoromethyl)-phosphonate (0.450 mL, 2.54 mmol), the reaction mixture was stirred at room temperature for 20 hours. After partitioned between EtOAc and water, the aqueous layer was extracted with EtOAc. The combined organic layers were washed with brine, dried over Na$_2$SO$_4$, filtered and concentrated in vacuo. The residue was purified by column chromatography on SiO$_2$ (Hexane:EtOAc=10:1 to 4:1) to give 5-bromo-1-(difluoromethyl)-1H-indazole (496 mg, 79%) as a yellow wax. $^1$H-NMR (400 MHz, DMSO-d$_6$): δ 8.87 (1H, d, J=0.8 Hz), 8.15 (1H, t, J=58.8 Hz), 8.09 (1H, dd, J=2.0, 1.2 Hz), 7.72 (1H, d, J=9.6 Hz), 7.47 (1H, dd, J=9.2, 1.6 Hz).

Intermediate 9:
5-bromo-1-(methylsulfonyl)-1H-indazole

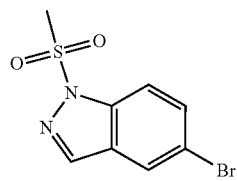

To a solution of 5-bromo-1H-indazole (1.00 g, 5.08 mmol) in DMF (15 mL) was added NaH (60% dispersion in mineral oil, 304 mg, 7.61 mmol) at 0° C. The mixture was stirred at room temperature for 30 minutes. After addition of methanesulfonyl chloride (0.450 mL, 5.81 mmol) at 0° C., the reaction mixture was stirred at room temperature for 2 hours and then quenched with saturated aq. NH$_4$Cl. The mixture was extracted with EtOAc, washed with brine, dried over Na$_2$SO$_4$, filtered and concentrated in vacuo. The residue was purified by column chromatography on SiO$_2$ (Hexane:EtOAc=4:1 to 3:1) to give 5-bromo-1-(methylsulfonyl)-1H-indazole (545 mg, 39%) as a white solid. $^1$H-NMR (400 MHz, DMSO-d$_6$): δ 8.57 (1H, d, J=1.2 Hz), 8.20 (1H, d, J=2.0 Hz), 7.91 (1H, d, J=9.2 Hz), 7.78 (1H, dd, J=9.2, 2.4 Hz), 3.50 (3H, s).

Intermediate 10: 2-(5-bromo-1H-indazol-1-yl)-2-methylpropan-1-ol

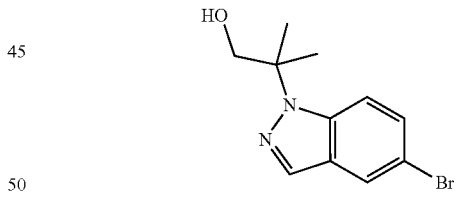

To a solution of 5-bromo-1H-indazole (500 mg, 2.54 mmol) in DMF (7.0 mL) was added NaH (60% dispersion in oil, 152 mg, 3.81 mmol) at 0° C. The mixture was stirred at room temperature for 30 minutes. After addition of 2,2-dimethyloxirane (0.460 mL, 5.10 mmol) at 0° C., the reaction mixture was stirred at room temperature for 21 hours and then quenched with saturated aq. NH$_4$Cl. The mixture was extracted with EtOAc, washed with brine, dried over Na$_2$SO$_4$, filtered and concentrated in vacuo. The residue was purified by column chromatography on SiO$_2$ (Hexane:EtOAc=4:1 to 1:1) to give 2-(5-bromo-1H-indazol-1-yl)-2-methylpropan-1-ol (496 mg, 79%) as a yellow wax. $^1$H-NMR (400 MHz, DMSO-d$_6$): δ 8.00 (1H, d, J=0.8 Hz), 7.91 (1H, d, J=1.6 Hz), 7.59 (1H, d, J=8.8 Hz), 7.47 (1H, dd, J=9.2, 2.0 Hz), 4.35 (2H, s), 1.21 (6H, s).

Intermediate 11: 5-bromo-1-methyl-1H-pyrazolo[3,4-b]pyridine

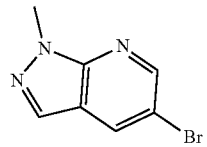

To a solution of 5-bromo-1H-pyrazolo[3,4-b]pyridine (500 mg, 2.52 mmol) in DMF (7.5 mL) was added Cs$_2$CO$_3$ (1.65 g, 5.06 mmol) at room temperature. The mixture was stirred at room temperature for 30 minutes. After addition of MeI (0.200 mL, 3.22 mmol), the reaction mixture was stirred at room temperature for 2 hours and then quenched wither water. The mixture was extracted with EtOAc, washed with brine, dried over Na$_2$SO$_4$, filtered and concentrated in vacuo. The residue was purified by column chromatography on SiO$_2$ (Hexane:EtOAc=4:1) to give 5-bromo-1-methyl-1H-pyrazolo[3,4-b]pyridine (400 mg, 75%) as a yellow solid. $^1$H-NMR (400 MHz, CDCl$_3$): δ 8.55 (1H, d, J=2.0 Hz), 8.18 (1H, d, J=2.0 Hz), 7.95 (1H, s), 4.14 (3H, s).

Intermediate 12: 5-bromo-1-methyl-1H-pyrazolo[4,3-b]pyridine

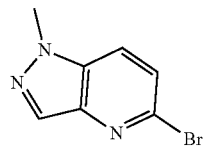

To a solution of 5-bromo-1H-pyrazolo[4,3-b]pyridine (500 mg, 2.52 mmol) in DMF (7.5 mL) was added Cs$_2$CO$_3$ (1.65 g, 5.06 mmol) at room temperature. The mixture was stirred at room temperature for 30 minutes. After addition of MeI (0.200 mL, 3.22 mmol), the reaction mixture was stirred at room temperature for 2 hours and then quenched water. The mixture was extracted with EtOAc, washed with brine, dried over Na$_2$SO$_4$, filtered and concentrated in vacuo. The residue was purified by column chromatography on SiO$_2$ (Hexane:EtOAc=4:1) to give 5-bromo-1-methyl-1H-pyrazolo[4,3-b]pyridine (267 mg, 50%) as a pale yellow solid. $^1$H-NMR (400 MHz, CDCl$_3$): δ 8.09 (1H, s), 7.88 (1H, dd, J=9.2, 0.8 Hz), 7.32 (1H, d, J=9.2 Hz), 4.24 (3H, s).

Intermediate 13: 5-bromo-1-methyl-1H-pyrazolo[3,4-c]pyridine

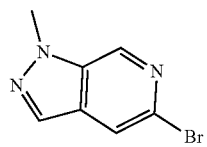

To a solution of 5-bromo-1H-pyrazolo[3,4-c]pyridine (500 mg, 2.52 mmol) in DMF (7.5 mL) was added Cs$_2$CO$_3$ (1.65 g, 5.06 mmol) at room temperature. The mixture was stirred at room temperature for 30 minutes. After addition of MeI (0.200 mL, 3.22 mmol), the reaction mixture was stirred at room temperature for 2 hours and then quenched water. The mixture was extracted with EtOAc, washed with brine, dried over Na$_2$SO$_4$, filtered and concentrated in vacuo. The residue was purified by column chromatography on SiO$_2$ (Hexane:EtOAc=4:1) to give 5-bromo-1-methyl-1H-pyrazolo[3,4-c]pyridine (320 mg, 60%) as a yellow solid. $^1$H-NMR (400 MHz, CDCl$_3$): δ 8.73 (1H, s), 7.98 (1H, s), 7.81 (1H, d, J=1.2 Hz), 4.18 (3H, s).

Intermediate 14: 5-bromo-1-(tetrahydro-2H-pyran-2-yl)-1H-pyrazolo[3,4-b]pyridine

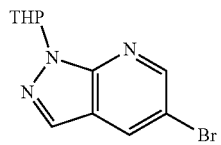

To a solution of 5-bromo-1H-pyrazolo[3,4-b]pyridine (500 mg, 2.52 mmol) in DCM (10 mL) was added p-TsOH·H$_2$O (96.0 mg, 0.505 mmol) and 3,4-dihydro-2H-pyran (0.693 mL, 7.57 mmol) at room temperature. The reaction mixture was stirred at room temperature for 3 hours. After concentration in vacuo, the residue was diluted with EtOAc and washed with saturated aq. NaHCO$_3$ and brine, dried over Na$_2$SO$_4$, filtered and concentrated in vacuo. The residue was purified by column chromatography on NH—SiO$_2$ (Hexane only to Hexane:EtOAc=5:1) to give 5-bromo-1-(tetrahydro-2H-pyran-2-yl)-1H-pyrazolo[3,4-b]pyridine (712 mg) as a colorless oil. $^1$H-NMR (400 MHz, CDCl$_3$): δ 8.56 (1H, d, J=2.0 Hz), 8.18 (1H, d, J=2.4 Hz), 8.01 (1H, s), 6.07 (1H, dd, J=10.2, 2.4 Hz), 3.89-3.72 (2H, m), 1.82-1.75 (2H, m), 1.58-1.49 (4H, m).

Intermediate 15: 5-bromo-1-(methyl-d$_3$)-1H-indazole

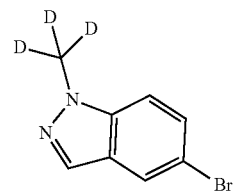 [SMILES: [2H]C([2H])([2H])n1ncc2cc(Br)ccc21]

To a solution of 5-bromoindazole (1.50 g, 7.61 mmol) in DMF (21 mL) was added Cs$_2$CO$_3$ (4.95 g, 15.2 mmol) at room temperature. The mixture was stirred at room temperature for 30 minutes. After addition of CD$_3$I (0.540 mL, 8.68 mmol), the reaction mixture was stirred at room temperature for 2 hours and then quenched water. The mixture was extracted with EtOAc, washed with brine, dried over Na$_2$SO$_4$, filtered and concentrated in vacuo. The residue was purified by column chromatography on SiO$_2$ (Hexane:EtOAc=4:1) to give 5-bromo-1-(methyl-d$_3$)-1H-indazole (857 mg, 53%) as an orange solid. $^1$H-NMR (400 MHz, CDCl$_3$): δ 7.91 (1H, d, J=0.8 Hz), 7.87 (1H, d, J=1.6 Hz), 7.45 (11H, dd, J=8.8, 1.6 Hz), 7.28 (11H, dt, J=8.4, 0.8 Hz).

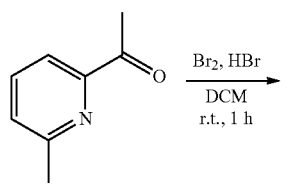

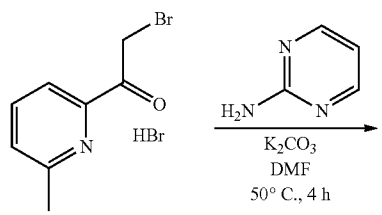

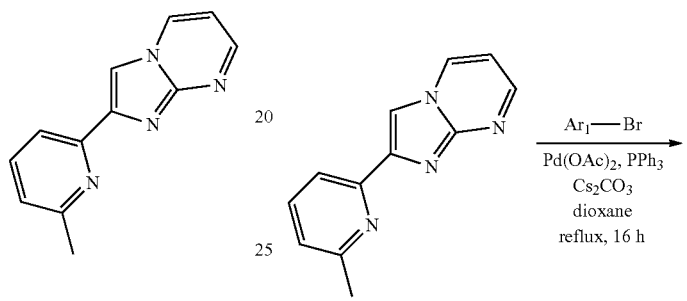

Intermediate 16: 2-(6-methylpyridin-2-yl)imidazo[1,2-a]pyrimidine

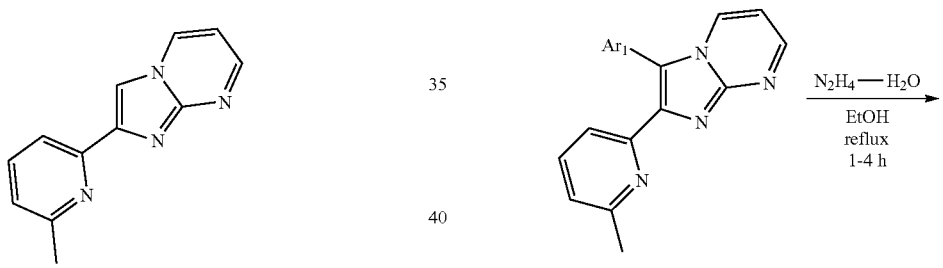

Step A: 2-bromo-1-(6-methylpyridin-2-yl)ethan-1-one hydrobromide

To a solution of 1-(6-methylpyridin-2-yl)ethan-1-one (5.00 g, 37.0 mmol) in DCM (40 mL) was slowly added HBr (33% solution in AcOH, 12.2 mL, 74.0 mmol) followed by Br$_2$ (1.90 mL, 37.0 mmol) at 0° C. The reaction mixture was stirred at room temperature for 1 hour. After diluted with diethyl ether, the mixture was stirred at room temperature for further 30 min. A precipitated solid was collected by filtration, washed with diethyl ether, and dried under vacuum to give 2-bromo-1-(6-methylpyridin-2-yl)ethan-1-one hydrobromide (11.3 g, >99%) as a yellow solid. $^1$H-NMR (400 MHz, CD$_3$OD): δ 8.54 (11H, t, J=8.0 Hz), 8.06 (1H, d, J=7.2 Hz), 7.95 (1H, d, J=8.0 Hz), 3.89 (1H, d, J=11.6 Hz), 3.79 (1H, d, J=11.2 Hz), 2.87 (3H, s).

Step B: 2-(6-methylpyridin-2-yl)imidazo[1,2-a]pyrimidine

To a solution of 2-bromo-1-(6-methylpyridin-2-yl)ethan-1-one hydrobromide (11.3 g, 38.4 mmol) in DMF (91 mL) was added pyrimidin-2-amine (3.65 g, 38.4 mmol) followed by K$_2$CO$_3$ (7.96 g, 57.6 mmol) at room temperature. The reaction mixture heated at 50° C. (internal temperature) for 4 hours and then concentrated in vacuo. The residue was partitioned between DCM and water. The separated aqueous layer was extracted with DCM. The combined organic layers were washed with brine, dried over Na$_2$SO$_4$, filtered, and concentrated in vacuo. The residue was solidified from DCM and diethyl ether to give 2-(6-methylpyridin-2-yl)imidazo[1,2-a]pyrimidine (4.79 g, 62% for 2 steps) as a pale brown solid. $^1$H-NMR (400 MHz, CD$_3$OD): δ 8.90 (1H, dd, J=2.4, 2.0 Hz), 8.58 (1H, dd, J=2.0, 1.6 Hz), 8.37 (11H, s), 7.95 (11H, d, J=7.6 Hz), 7.78 (1H, t, J=7.8 Hz), 7.23 (1H, d, J=7.6 Hz), 7.06 (1H, q, J=4.0 Hz), 2.58 (3H, s).

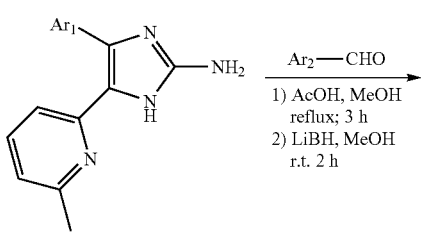

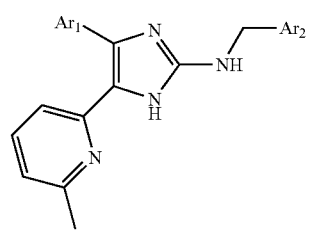

-continued

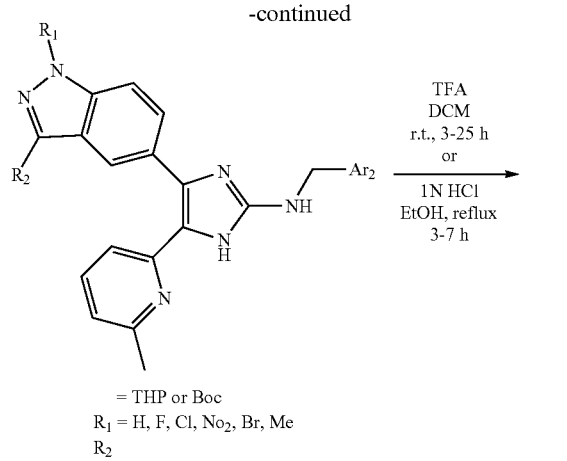

= THP or Boc
R$_1$ = H, F, Cl, No$_2$, Br, Me
R$_2$

Example 1: N-(2-fluorobenzyl)-4-(1H-indazol-5-yl)-5-(6-methylpyridin-2-yl)-1H-imidazol-2-amine

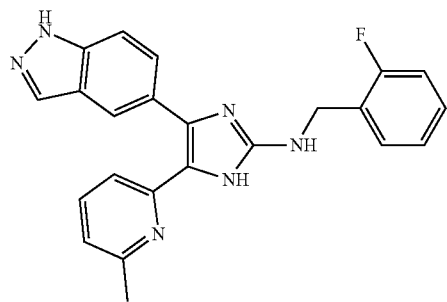 [SMILES: Cc1cccc(-c2[nH]c(NCc3ccccc3F)nc2-c2ccc3[nH]ncc3c2)n1]

Step A: 2-(6-methylpyridin-2-yl)-3-(1-(tetrahydro-2H-pyran-2-yl)-1H-indazol-5-yl)imidazo[1,2-a]pyrimidine A mixture of 2-(6-methylpyridin-2-yl)imidazo[1,2-a]pyrimidine (Intermediate 16, 200 mg, 0.951 mmol), 5-bromo-1-(tetrahydro-2H-pyran-2-yl)-1H-indazole (Intermediate 1, 281 mg, 0.999 mmol), Pd(OAc)$_2$ (8.54 mg, 0.0380 mmol), PPh$_3$ (20.0 mg, 0.0760 mmol) and Cs$_2$CO$_3$ (341 mg, 1.05 mmol) in dioxane (3.2 mL) was degassed by purging and re-filled with Ar in several times. The reaction mixture was refluxed for 4 hours and cooled to room temperature. After dilution with DCM, the mixture was filtered through a Celite pad. The filtrate was partitioned between DCM and water. The separated aqueous layer was extracted with DCM. The combined organic layers were washed with brine, dried over Na$_2$SO$_4$, filtered, and concentrated in vacuo. The residual solid was purified by recrystallization from DCM and diethyl ether to afford 2-(6-methylpyridin-2-yl)-3-(1-(tetrahydro-2H-pyran-2-yl)-1H-indazol-5-yl)imidazo[1,2-a]pyrimidine (346 mg, 89%) as a brown solid. $^1$H-NMR (400 MHz, DMSO-d$_6$): δ 8.62-8.59 (2H, m), 8.20 (1H, s), 8.08 (1H, s), 7.86-7.84 (2H, m), 7.72 (1H, t, J=8.0 Hz), 7.63-7.55 (2H, m), 7.13 (1H, d, J=7.2 Hz), 7.03 (1H, m), 5.93 (1H, d, J=8.8 Hz), 3.94-3.75 (2H, m), 2.22 (3H, s), 2.08-1.99 (2H, m), 1.78-1.61 (3H, m).

Step B: 5-(6-methylpyridin-2-yl)-4-(1-(tetrahydro-2H-pyran-2-yl)-1H-indazol-5-yl)-1H-imidazol-2-amine To a solution of 2-(6-methylpyridin-2-yl)-3-(1-(tetrahydro-2H-pyran-2-yl)-1H-indazol-5-yl)imidazo[1,2-a]pyrimidine (340 mg, 0.828 mmol) in EtOH (2.8 mL) was added hydrazine hydrate (0.201 mL, 0.828 mmol) at room temperature. The reaction mixture was refluxed for 1 hour and cooled to room temperature. After filtered through a Celite pad while washing with MeOH, the filtrate was concentrated in vacuo. The residue was purified by column chromatography on NH—SiO$_2$ (DCM:MeOH=97:3) to afford 5-(6-methylpyridin-2-yl)-4-(1-(tetrahydro-2H-pyran-2-yl)-1H-indazol-5-yl)-1H-imidazol-2-amine (240 mg, 77%) as a white solid. $^1$H-NMR (400 MHz, DMSO-d$_6$): δ 10.5 (11H, brs), 8.11 (11H, brs), 7.92 (1H, s), 7.77-7.64 (1H, m), 7.62-7.54 (1H, m), 7.40 (1H, t, J=7.6 Hz), 7.05 (1H, d, J=7.6 Hz), 6.91 (11H, d, J=7.2 Hz), 5.84 (1H, dd, J=9.6, 2.4 Hz), 5.39 (2H, brs), 3.92-3.72 (2H, m), 2.46 (3H, s), 2.06-1.96 (2H, m), 1.81-1.58 (4H, m).

Step C: N-(2-fluorobenzyl)-5-(6-methylpyridin-2-yl)-4-(1-(tetrahydro-2H-pyran-2-yl)-1H-indazol-5-yl)-1H-imidazol-2-amine To a solution of 5-(6-methylpyridin-2-yl)-4-(1-(tetrahydro-2H-pyran-2-yl)-1H-indazol-5-yl)-1H-imidazol-2-amine (100 mg, 0.267 mmol) in MeOH (0.89 mL) was added 2-fluorobenzaldehyde (0.0840 mL, 0.801 mmol) followed by AcOH (7.64 µL, 0.134 mmol) at room temperature. The mixture was refluxed for 3 hours and cooled to room temperature. After addition of LiBH$_4$ (2 M solution in THF, 0.267 mL, 0.534 mmol) at room temperature, the reaction mixture was stirred at room temperature for 2 hours and quenched with saturated aq. NH$_4$Cl. The mixture was extracted with DCM, washed with brine, dried over Na$_2$SO$_4$, filtered, and concentrated in vacuo. The residue was purified by column chromatography on NH—SiO$_2$ (DCM:MeOH=95:5) to afford N-(2-fluorobenzyl)-5-(6-methylpyridin-2-yl)-4-(1-(tetrahydro-2H-pyran-2-yl)-1H-indazol-5-yl)-1H-imidazol-2-amine (118 mg, 92%). $^1$H-NMR (400 MHz, DMSO-d$_6$): δ 11.06 and 10.84 (1H, brs+brs), 8.10 (1H, brs), 7.93 (1H, s), 7.77-7.62 (1H, m), 7.58-7.40 (3H, m), 7.31-7.28 (1H, m), 7.25-7.15 (2H, m), 7.10-7.00 (1H, m), 7.00-6.90 (1H, m), 6.20-6.13 (1H, m), 5.84 (1H, d, J=9.6 Hz), 4.54 (2H, d, J=6.0 Hz), 3.92-3.71 (2H, m), 2.46-2.31 (3H, m), 2.05-1.58 (4H, m)

Step D: N-(2-fluorobenzyl)-4-(1H-indazol-5-yl)-5-(6-methylpyridin-2-yl)-1H-imidazol-2-amine A mixture of N-(2-fluorobenzyl)-5-(6-methylpyridin-2-yl)-4-(1-(tetrahydro-2H-pyran-2-yl)-1H-indazol-5-yl)-1H-imidazol-2-amine (118 mg, 0.245 mmol) and TFA (0.377 mL, 4.89 mmol) in DCM (2.5 mL) was stirred at room temperature for 3 hours. The reaction mixture was diluted with DCM, washed with saturated aq. NaHCO₃ and brine, dried over Na₂SO₄, filtered, and concentrated in vacuo. The residue was purified by column chromatography on NH—SiO₂ (DCM:MeOH=97:3) to afford N-(2-fluorobenzyl)-4-(1H-indazol-5-yl)-5-(6-methylpyridin-2-yl)-1H-imidazol-2-amine (40.0 mg, 41%). $^1$H-NMR (400 MHz, CD₃OD): δ 8.04 (1H, s), 7.88 (1H, s), 7.55-7.47 (3H, m), 7.39 (1H, brs), 7.33-7.27 (1H, m), 7.18-6.96 (4H, m), 4.61 (2H, s), 2.49 (3H, s). MS: 399.1 [M+H]⁺

Example 2: 4-(3-fluoro-1H-indazol-5-yl)-N-(2-fluorobenzyl)-5-(6-methylpyridin-2-yl)-1H-imidazol-2-amine

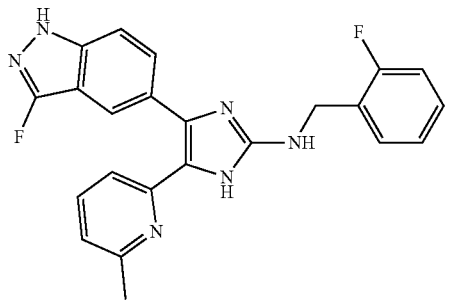

Step A: 3-(3-fluoro-1-(tetrahydro-2H-pyran-2-yl)-1H-indol-5-yl)-2-(6-methylpyridin-2-yl)imidazo-[1,2-a]pyrimidine To a solution of 2-(6-methylpyridin-2-yl)imidazo[1,2-a]pyrimidine (Intermediate 16, 171 mg, 0.812 mmol) and 5-bromo-3-fluoro-1-(tetrahydro-2H-pyran-2-yl)-1H-indazole (Intermediate 2, 255 mg, 0.852 mmol) in 1,4-dioxane (2.7 mL) was added PPh₃ (34.0 mg, 0.130 mmol), Cs₂CO₃ (291 mg, 0.893 mmol) and Pd(OAc)₂ (15.0 mg, 0.065 mmol) at room temperature. After degassed by purging and re-filled with N₂, the reaction mixture was refluxed for 16 hours, cooled to room temperature and then filtered through a Celite pad while washing with DCM. The filtrate was washed with saturated aq. NaHCO₃ and brine, dried over Na₂SO₄, filtered and concentrated in vacuo. The residue was purified by column chromatography on NH—SiO₂ (Hexane:EtOAc=1:1 to EtOAc only) to give 3-(3-fluoro-1-(tetrahydro-2H-pyran-2-yl)-1H-indol-5-yl)-2-(6-methylpyridin-2-yl)imidazo-[1,2-a]pyrimidine (322 mg, 93%) as a yellow solid. $^1$H-NMR (400 MHz, CDCl₃): δ 8.60 (2H, d, J=2.0 Hz), 8.31 (2H, d, J=6.8 Hz), 7.94 (4H, d, J=4.4 Hz), 7.70-7.46 (11H, m), 7.02 (1H, d, J=7.6 Hz), 6.86-6.83 (1H, m), 5.66 (1H, s), 4.04 (1H, s), 3.76 (1H, s), 2.53-2.49 (2H, m), 2.36-2.31 (5H, m), 2.16-2.05 (5H, m), 1.77-1.69 (6H, m).

Step B: 4-(3-fluoro-1-(tetrahydro-2H-pyran-2-yl)-1H-indazol-5-yl)-5-(6-methylpyridin-2-yl)-1H-imidazol-2-amine To a solution of 3-(3-fluoro-1-(tetrahydro-2H-pyran-2-yl)-1H-indol-5-yl)-2-(6-methylpyridin-2-yl)imidazo-[1,2-a]pyrimidine (322 mg, 0.748 mmol) in EtOH (2.8 mL) was added hydrazine monohydrate (20 wt %, 0.201 mL, 0.828 mmol) at room temperature. The reaction mixture was refluxed for 4 hours and cooled to room temperature. After filtered through a Celite pad while washing with MeOH, the filtrate was concentrated in vacuo. The residue was purified by column chromatography on NH—SiO₂ (DCM:MeOH=97:3) to afford 4-(3-fluoro-1-(tetrahydro-2H-pyran-2-yl)-1H-indazol-5-yl)-5-(6-methylpyridin-2-yl)-1H-imidazol-2-amine (162 mg, 55%) as a yellow solid. $^1$H-NMR (400 MHz, DMSO-d₆): δ 10.84 (2H, brs+brs), 7.96 (2H, s), 7.75-7.69 (3H, m), 7.58-7.56 (1H, m), 7.46 (2H, t, J=8.0 Hz), 7.09 (2H, d, J=7.6 Hz), 6.96-6.91 (2H, d, J=7.2 Hz), 5.79-5.77 (2H, m), 5.76 (2H, s), 5.49 (4H, s, 4H), 3.91-3.88 (2H, m), 3.75-3.69 (2H, m), 2.47 (6H, s), 2.35-2.20 (4H, m), 2.03-1.93 (5H, m), 1.78-1.68 (3H, m).

Step C: 4-(3-fluoro-1-(tetrahydro-2H-pyran-2-yl)-1H-indazol-5-yl)-N-(2-fluorobenzyl)-5-(6-methylpyridin-2-yl)-1H-imidazol-2-amine 4-(3-Fluoro-1-(tetrahydro-2H-pyran-2-yl)-1H-indazol-5-yl)-N-(2-fluorobenzyl)-5-(6-methyl-pyridin-2-yl)-1H-imidazol-2-amine (83.0 mg, 65% for 2 steps) as a yellow solid was synthesized from 4-(3-fluoro-1-(tetrahydro-2H-pyran-2-yl)-1H-indazol-5-yl)-5-(6-methylpyridin-2-yl)-1H-imidazol-2-amine (100 mg, 0.255 mmol) and 2-fluorobenzaldehyde (0.081 mL, 0.764 mmol) by following the procedure for Example 1 (Step C). $^1$H-NMR (400 MHz, DMSO-d₆): δ 11.17-10.76 (1H, brs+brs), 8.24-7.96 (1H, brs+brs), 7.89-7.68 (2H, m), 7.60-7.46 (3H, m), 7.29 (1H, t, J=12.8 Hz), 7.21-7.16 (1H, m), 7.09 (1H, d, J=7.6 Hz), 6.97 (1H, d, J=8.0 Hz), 6.29-6.19 (1H, t+t), 5.79-5.77 (1H, m), 4.54 (2H, d, J=6.4 Hz), 3.90-3.88 (1H, m), 3.75-3.69 (1H, m), 2.47 (3H, s), 2.34-2.25 (1H, m), 1.99-1.93 (2H, m), 1.74-1.70 (1H, m), 1.57-1.55 (2H, d, J=3.7 Hz). MS: 501.1 [M+H]⁺

Step D: 4-(3-fluoro-1H-indazol-5-yl)-N-(2-fluorobenzyl)-5-(6-methylpyridin-2-yl)-1H-imidazol-2-amine 4-(3-Fluoro-1H-indazol-5-yl)-N-(2-fluorobenzyl)-5-(6-methylpyridin-2-yl)-1H-imidazol-2-amine (24.0 mg, 35%) as a yellow solid was synthesized from 4-(3-fluoro-1-(tetrahydro-2H-pyran-2-yl)-1H-indazol-5-yl)-5-(6-methylpyridin-2-yl)-1H-imidazol-2-amine (83.0 mg, 0.166 mmol) and TFA (0.260 mL, 3.38 mmol) by following the procedure for Example 1 (Step D). $^1$H-NMR (400 MHz, DMSO-d₆): δ 11.11-10.70 (1H, brs+brs), 8.04 (1H, brs+brs), 7.78-7.38 (4H, m), 7.33-7.28 (1H, m), 7.21-7.16 (2H, m), 7.08 (1H, d, J=8.4 Hz), 6.95 (1H, d, J=7.2 Hz), 6.23-6.16 (1H, m), 4.54 (2H, d, J=6.4 Hz, 2H), 2.46 (s, 3H). MS: 417.1 [M+H]⁺.

Example 3: 4-(3-chloro-1H-indazol-5-yl)-N-(2-fluorobenzyl)-5-(6-methylpyridin-2-yl)-1H-imidazol-2-amine

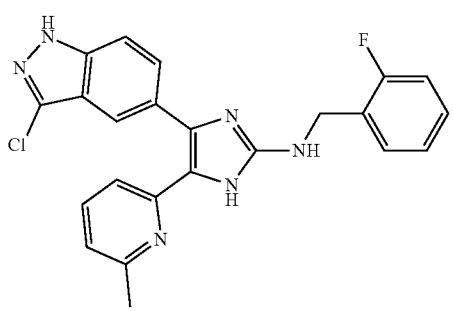 [SMILES: Cc1cccc(-c2[nH]c(NCc3ccccc3F)nc2-c2ccc3[nH]nc(Cl)c3c2)n1]

Step A: 3-(3-chloro-1-(tetrahydro-2H-pyran-2-yl)-1H-indol-5-yl)-2-(6-methylpyridin-2-yl)imi-dazo-[1,2-a]pyrimidine To a solution of 2-(6-methylpyridin-2-yl)imidazo[1,2-a]pyrimidine (Intermediate 16, 200 mg, 0.951 mmol) and 5-bromo-3-chloro-1-(tetrahydro-2H-pyran-2-yl)-1H-indazole (Intermediate 3, 315 mg, 0.999 mmol) in 1,4-dioxane (3.2 mL) was added PPh$_3$ (40.0 mg, 0.152 mmol), Cs$_2$CO$_3$ (341 mg, 1.046 mmol) and Pd(OAc)$_2$ (17.0 mg, 0.076 mmol) at room temperature. After degassed by purging and re-filled with N$_2$, the reaction mixture was refluxed for 16 hours, cooled to room temperature and then filtered through a Celite pad while washing with DCM. The filtrate was washed with saturated aq. NaHCO$_3$ and brine, dried over Na$_2$SO$_4$, filtered and concentrated in vacuo. The residue was purified by column chromatography on NH—SiO$_2$ (Hexane:EtOAc=1:1 to EtOAc only) to give 3-(3-chloro-1-(tetrahydro-2H-pyran-2-yl)-1H-indol-5-yl)-2-(6-methylpyridin-2-yl)imi-dazo-[1,2-a]pyrimidine (285 mg, 67%) as a yellow solid. $^1$H-NMR (400 MHz, CDCl$_3$): δ 8.60 (1H, s), 8.33 (1H, m), 8.00-7.94 (2H, m), 7.69-7.46 (12H, m), 7.26 (5H, s), 7.02 (1H, m), 6.84 (1H, s), 5.74 (1H, m), 4.04 (1H, s), 3.77 (1H, s), 2.59 (1H, s), 2.32 (4H, s), 1.74 (4H, m).

Step B: 4-(3-chloro-1-(tetrahydro-2H-pyran-2-yl)-1H-indazol-5-yl)-5-(6-methylpyridin-2-yl)-1H-imidazol-2-amine To a solution of 3-(3-chloro-1-(tetrahydro-2H-pyran-2-yl)-1H-indol-5-yl)-2-(6-methylpyridin-2-yl)imi-dazo-[1,2-a]pyrimidine (285 mg, 0.638 mmol) in EtOH (2.1 mL) was added hydrazine monohydrate (20 wt %, 0.160 mL, 0.658 mmol) at room temperature. The reaction mixture was refluxed for 2 hours and cooled to room temperature. After filtered through a Celite pad while washing with MeOH, the filtrate was concentrated in vacuo. The residue was purified by column chromatography on NH—SiO$_2$ (DCM:MeOH=97:3) to afford 4-(3-chloro-1-(tetrahydro-2H-pyran-2-yl)-1H-indazol-5-yl)-5-(6-methylpyridin-2-yl)-1H-imidazol-2-amine (173 mg, 66%) as a yellow solid. $^1$H-NMR (400 MHz, DMSO-d$_6$): δ 10.86 (1H, brs+brs), 8.00 (1H, s), 7.78-7.71 (1H, m), 7.64-7.55 (1H, m), 7.48 (1H, t, J=8.0 Hz), 7.11 (1H, d, J=8.0 Hz), 6.99-6.95 (1H, m), 5.84 (1H, dd, J=2.4, 1.6 Hz), 5.50-5.37 (2H, brs+brs), 3.90 (1H, d, J=10.8 Hz), 3.79-3.71 (1H, m), 2.48 (3H, s), 2.42-2.29 (3H, m), 2.04-1.96 (3H, m), 1.79-1.52 (4H, m).

Step C: 4-(3-chloro-1-(tetrahydro-2H-pyran-2-yl)-1H-indazol-5-yl)-N-(2-fluorobenzyl)-5-(6-methylpyridin-2-yl)-1H-imidazol-2-amine 4-(3-Chloro-1-(tetrahydro-2H-pyran-2-yl)-1H-indazol-5-yl)-N-(2-fluorobenzyl)-5-(6-methyl pyridin-2-yl)-1H-imidazol-2-amine (56.0 mg, 44% for 2 steps) as a yellow solid was synthesized from 4-(3-chloro-1-(tetrahydro-2H-pyran-2-yl)-1H-indazol-5-yl)-5-(6-methylpyridin-2-yl)-1H-imidazol-2-amine (100 mg, 0.245 mmol) and 2-fluorobenzaldehyde (0.077 mL, 0.734 mmol) by following the procedure for Example 1 (Step C). $^1$H-NMR (400 MHz, DMSO-d$_6$): δ 11.21-10.80 (1H, brs+brs), 8.32-8.00 (1H, brs+brs), 7.78-7.70 (2H, m), 7.60-7.47 (2H, m), 7.30 (1H, m), 7.21-7.16 (2H, m), 7.11 (1H, m), 6.98 (1H, m), 6.29-6.23 (1H, t+t), 5.86-5.83 (1H, m), 4.56-4.53 (2H, m), 3.90 (1H, m), 3.73 (1H, m), 2.48 (3H, s), 2.37-2.32 (1H, m), 2.04-1.97 (2H, m), 1.73 (1H, m), 1.58 (2H, m). MS: 517.1 [M+H]$^+$

Step D: 4-(3-chloro-1H-indazol-5-yl)-N-(2-fluorobenzyl)-5-(6-methylpyridin-2-yl)-1H-imidazol-2-amine 4-(3-Chloro-1H-indazol-5-yl)-N-(2-fluorobenzyl)-5-(6-methylpyridin-2-yl)-1H-imidazol-2-amine (13.0 mg, 28%) as a yellow solid was synthesized from 4-(3-chloro-1-(tetrahydro-2H-pyran-2-yl)-1H-indazol-5-yl)-N-(2-fluorobenzyl)-5-(6-methylpyridin-2-yl)-1H-imidazol-2-amine (56.0 mg, 0.108 mmol) and TFA (0.170 mL, 2.20 mmol) by following the procedure for Example 1 (Step D). $^1$H-NMR (400 MHz, DMSO-d$_6$): δ 11.14-10.73 (1H, brs+brs), 8.26-7.96 (1H, brs+brs), 7.69-7.47 (4H, m), 7.31-6.96 (5H, m), 6.21-6.18 (1H, s), 4.55 (2H, d, J=5.6 Hz), 2.48 (3H, s). MS: 433.0 [M+H]$^+$.

Example 4: N-(2-fluorobenzyl)-5-(6-methylpyridin-2-yl)-4-(3-nitro-1H-indazol-5-yl)-1H-imidazol-2-amine

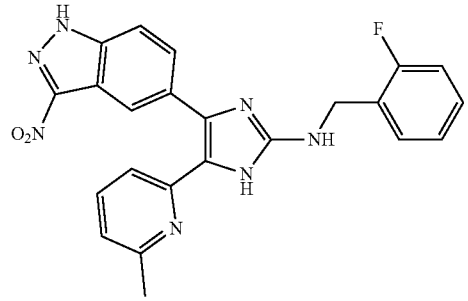 [SMILES: Cc1cccc(-c2[nH]c(NCc3ccccc3F)nc2-c2ccc3[nH]nc([N+](=O)[O-])c3c2)n1]

Step A: 2-(6-methylpyridin-2-yl)-3-(3-nitro-1-(tetrahydro-2H-pyran-2-yl)-1H-indol-5-yl)imi-dazo-[1,2-a]pyrimidine To a solution of 2-(6-methylpyridin-2-yl)imidazo[1,2-a]pyrimidine (Intermediate 16, 200 mg, 0.951 mmol) and 5-bromo-3-chloro-1-(tetrahydro-2H-pyran-2-yl)-1H-indazole (Intermediate 4, 326 mg, 0.999 mmol) in 1,4-dioxane (3.20 mL) was added PPh$_3$ (40.0 mg, 0.152 mmol), Cs$_2$CO$_3$ (341 mg, 1.046 mmol) and Pd(OAc)$_2$ (17.0 mg, 0.076 mmol) at room temperature. After degassed by purging and re-filled with N$_2$, the reaction mixture was refluxed for 16 hours, cooled to room temperature and then filtered through a Celite pad while washing with DCM. The filtrate was washed with saturated aq. NaHCO$_3$ and brine, dried over Na$_2$SO$_4$, filtered and concentrated in vacuo. The residue was purified by column chromatography on NH—SiO$_2$ (Hexane:EtOAc=1:1) to give 2-(6-methylpyridin-2-yl)-3-(3-nitro-1-(tetrahydro-2H-pyran-2-yl)-1H-indol-5-yl)imidazo-[1,2-a]pyrimidine (408 mg, 94%) as a brown solid. $^1$H-NMR (400 MHz, CDCl$_3$): δ 8.56 (1H, d, J=6.4 Hz), 8.51 (1H, d, J=2.4 Hz), 8.13-8.00 (3H, m), 7.66 (4H, m), 7.53-7.39 (7H, m), 6.86-6.80 (2H, m), 5.87 (1H, t, J=7.2 Hz), 4.00-3.97 (1H, m), 3.79-3.74 (1H, m), 2.56 (1H, m), 2.16 (2H, m), 1.99 (3H, m), 1.80-1.67 (3H, m).

Step B: 5-(6-methylpyridin-2-yl)-4-(3-nitro-1-(tetrahydro-2H-pyran-2-yl)-1H-indazol-5-yl)-1H-imidazol-2-amine To a solution of 2-(6-methylpyridin-2-yl)-3-(3-nitro-1-(tetrahydro-2H-pyran-2-yl)-1H-indol-5-yl)imidazo-[1,2-a]

pyrimidine (408 mg, 0.892 mmol) in EtOH (3.0 mL) was added hydrazine monohydrate (20 wt %, 0.220 mL, 0.908 mmol) at room temperature. The reaction mixture was refluxed for 2 hours and cooled to room temperature. After filtered through a Celite pad while washing with MeOH, the filtrate was concentrated in vacuo. The residue was purified by column chromatography on NH—SiO$_2$ (DCM: MeOH=97:3) to afford 5-(6-methylpyridin-2-yl)-4-(3-nitro-1-(tetrahydro-2H-pyran-2-yl)-1H-indazol-5-yl)-1H-imidazol-2-amine (160 mg, 43%) as a yellow solid. $^1$H-NMR (400 MHz, CDCl$_3$): δ 8.36 (1H, s), 7.86 (1H, d, J=8.0 Hz), 7.58 (1H, d, J=8.8 Hz), 7.28 (6H, m), 6.84 (1H, d, J=7.6 Hz), 6.74 (1H, s), 5.81 (1H, d, J=8.4 Hz), 4.03 (1H, m), 3.79 (1H, m), 2.52 (5H, m), 2.16 (2H, m), 1.79 (3H, m).

Step C: N-(2-fluorobenzyl)-5-(6-methylpyridin-2-yl)-4-(3-nitro-1-(tetrahydro-2H-pyran-2-yl)-1H-indazol-5-yl)-1H-imidazol-2-amine N-(2-Fluorobenzyl)-5-(6-methylpyridin-2-yl)-4-(3-nitro-1-(tetrahydro-2H-pyran-2-yl)-1H-indazol-5-yl)-1H-imidazol-2-amine (28 mg, 28% for 2 steps) as a brown solid was synthesized from 5-(6-methylpyridin-2-yl)-4-(3-nitro-1-(tetrahydro-2H-pyran-2-yl)-1H-indazol-5-yl)-1H-imidazol-2-amine (80.0 mg, 0.191 mmol) and 2-fluorobenzaldehyde (0.060 mL, 0.572 mmol) by following the procedure for Example 1 (Step C). $^1$H-NMR (400 MHz, DMSO-d$_6$): δ 11.31-10.98 (1H, brs+brs), 8.34 (1H, brs+brs), 8.07 (1H, d, J=8.0 Hz), 7.58-7.51 (2H, m), 7.50-7.42 (1H, m), 7.33-7.28 (1H, m), 7.22-7.15 (2H, m), 6.91 (2H, t, J=7.6 Hz), 6.53-6.30 (1H, t+t), 6.01-5.98 (1H, m), 4.53-4.47 (2H, m), 3.92-3.75 (2H, m), 2.37-2.31 (3H, m), 2.09-2.02 (2H, m), 1.64-1.57 (2H, m). MS: 528.1 [M+H]$^+$ Step D: N-(2-fluorobenzyl)-5-(6-methylpyridin-2-yl)-4-(3-nitro-1H-indazol-5-yl)-1H-imidazol-2-amine To a solution of N-(2-fluorobenzyl)-5-(6-methylpyridin-2-yl)-4-(3-nitro-1-(tetrahydro-2H-pyran-2-yl)-1H-indazol-5-yl)-1H-imidazol-2-amine (53.0 mg, 0.100 mmol) in EtOH (0.59 mL) was added HCl (1M solution in EtOAc, 0.200 mL, 0.200 mmol). The reaction mixture was refluxed for 7 hours and concentrated in vacuo. The residue was basified with saturated aq. NaHCO$_3$ until pH 8. The mixture was extracted with DCM, washed with brine, dried over Na$_2$SO$_4$, filtered and concentrated in vacuo. The residue was purified by column chromatography on NH—SiO$_2$ (DCM: MeOH=97:3 to 95:5) to give N-(2-fluorobenzyl)-5-(6-methylpyridin-2-yl)-4-(3-nitro-1H-indazol-5-yl)-1H-imidazol-2-amine (3.00 mg, 6.7%) as a yellow solid. $^1$H-NMR (400 MHz, DMSO-d$_6$): δ 10.95 (1H, m), 8.30 (1H, m), 7.86 (1H, m), 7.55-7.39 (3H, m), 7.34-7.28 (1H, m), 7.20-7.15 (2H, m), 6.92-6.82 (2H, m), 6.49-6.25 (1H, m), 4.52-4.47 (2H, m), 2.33 (s, 3H). MS: 444.1 [M+H]$^+$.

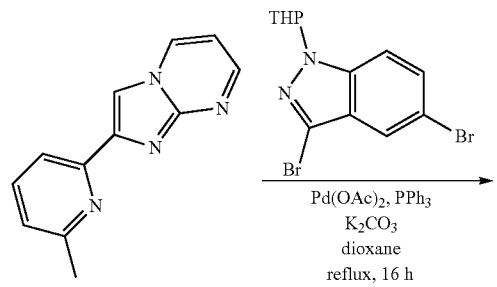

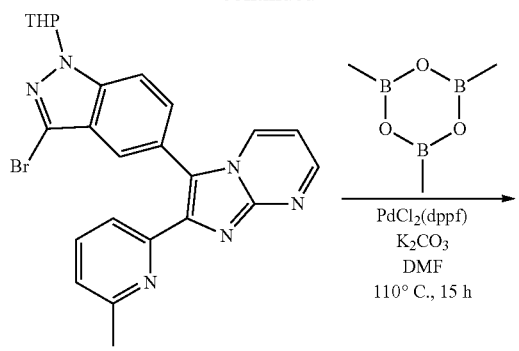

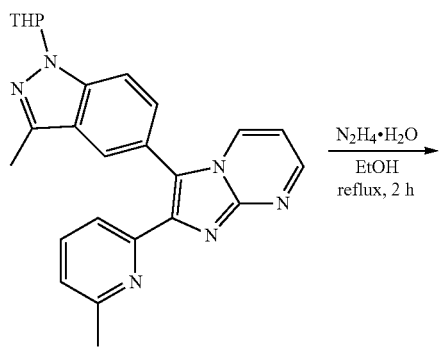

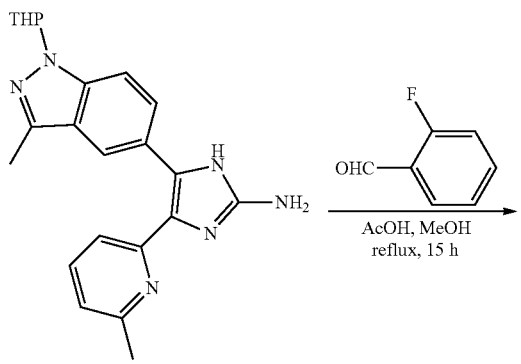

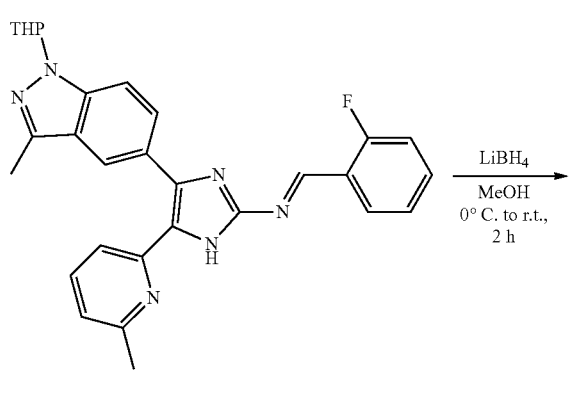

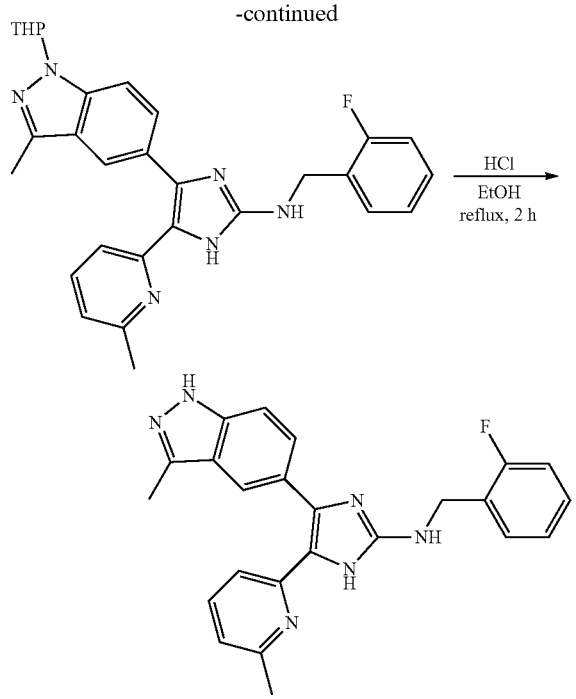

Example 5: N-(2-fluorobenzyl)-4-(3-methyl-1H-indazol-5-yl)-5-(6-methylpyridin-2-yl)-1H-imidazol-2-amine

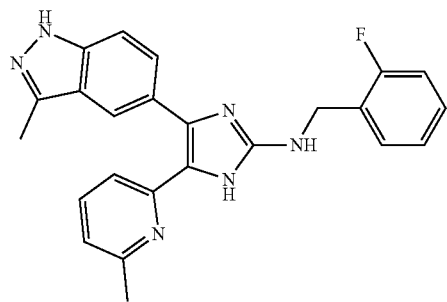 [SMILES: Cc1cccc(-c2[nH]c(NCc3ccccc3F)nc2-c2ccc3[nH]nc(C)c3c2)n1]

Step A: 3-(3-bromo-1-(tetrahydro-2H-pyran-2-yl)-1H-indazol-5-yl)-2-(6-methylpyridin-2-yl)imidazo[1,2-a]pyrimidine A mixture of 2-(6-methylpyridin-2-yl)imidazo[1,2-a]pyrimidine (Intermediate 16, 292 mg, 1.38 mmol), 5-dibromo-1-(tetrahydro-2H-pyran-2-yl)-1H-indazole (Intermediate 5, 500 mg, 1.38 mmol), PPh$_3$ (58.0 mg, 0.222 mmol), Pd(OAc)$_2$ (25.0 mg, 0.111 mmol) and Cs$_2$CO$_3$ (498 mg, 1.52 mmol) in dioxane (4.5 mL) was degassed by purging and re-filled with N$_2$ in several times. The reaction mixture was refluxed for 16 hours and cooled to room temperature. After diluted with DCM, the mixture was filtered through a Celite pad. The filtrate was partitioned between DCM and water. The separated aqueous layer was extracted with DCM. The combined organic layers were washed with brine, dried over Na$_2$SO$_4$, filtered, and concentrated in vacuo. The residue was purified by column chromatography on NH—SiO$_2$ (Hexanes:EtOAc=1:1 to EtOAc only) to give 3-(3-bromo-1-(tetrahydro-2H-pyran-2-yl)-1H-indazol-5-yl)-2-(6-methylpyridin-2-yl)imidazo-[1,2-a]pyrimidine (315 mg, 46%) as a yellow foam. $^1$H-NMR (400 MHz, CDCl$_3$): δ 8.60 (1H, dd, J=4.0, 2.4 Hz), 8.33 (1H, dd, J=6.8, 2.4 Hz), 7.96-7.94 (2H, m), 7.70-7.68 (1H, m), 7.60-7.57 (2H, m), 7.01 (1H, d, J=8.0 Hz), 6.85 (1H, dd, J=6.8, 4.0 Hz), 5.75 (1H, dd, J=9.2, 2.8 Hz), 4.07-4.04 (1H, m), 3.80-3.74 (1H, m), 2.61-2.34 (1H, m), 2.32 (3H, s), 2.20-2.12 (2H, m), 1.82-1.68 (3H, m), MS: 490 [M+H]$^+$ Step B: 3-(3-methyl-1-(tetrahydro-2H-pyran-2-yl)-1H-indazol-5-yl)-2-(6-methylpyridin-2-yl)imidazo[1,2-a]pyrimidine A mixture solution of 3-(3-bromo-1-(tetrahydro-2H-pyran-2-yl)-1H-indazol-5-yl)-2-(6-methylpyridin-2-yl)imidazo[1,2-a]pyrimidine (315 mg, 0.644 mmol), PdCl$_2$(dppf) (47.1 mg, 0.0640 mmol), trimethylboroxine (0.400 mL, 2.86 mmol) and K$_2$CO$_3$ (445 mg, 3.22 mmol) in DMF (6.2 mL) was degassed by purging and re-filled with N$_2$ in several times. The reaction mixture was heated at 110° C. for 15 hours in a sealed-tube and cooled to room temperature. After dilution with water, the mixture was extracted with DCM twice. The combined organic layers were washed with brine, dried over Na$_2$SO$_4$, filtered, and concentrated in vacuo. The residue was purified by column chromatography on NH—SiO$_2$ (Hexanes:EtOAc=1:1 to EtOAc only) to afford 3-(3-methyl-1-(tetrahydro-2H-pyran-2-yl)-1H-indazol-5-yl)-2-(6-methylpyridin-2-yl)imidazo[1,2-a]pyrimidine (230 mg, 84%) as a pale brown foam. $^1$H-NMR (400 MHz, CDCl$_3$): δ 8.58 (1H, dd, J=4.0, 2.4 Hz), 8.29 (1H, dd, J=6.8, 1.6 Hz), 7.92 (1H, s), 7.82 (1H, d, J=6.8 Hz), 7.69-7.67 (1H, m), 7.60-7.54 (2H, m), 6.99 (1H, d, J=7.6 Hz), 6.80 (1H, dd, J=6.8, 4.0 Hz), 5.68 (1H, dd, J=10, 2.0 Hz), 4.12-4.09 (1H, m), 3.81-3.75 (1H, m), 2.61-2.34 (1H, m), 2.57 (3H, s), 2.33 (3H, s), 2.17-2.10 (2H, m), 1.84-1.70 (3H, m). MS: 425.2 [M+H]$^+$ Step C: 5-(3-methyl-1-(tetrahydro-2H-pyran-2-yl)-1H-indazol-5-yl)-4-(6-methylpyridin-2-yl)-1H-imidazol-2-amine To a solution of 3-(3-methyl-1-(tetrahydro-2H-pyran-2-yl)-1H-indazol-5-yl)-2-(6-methyl-pyridin-2-yl)imidazo[1,2-a]pyrimidine (230 mg, 0.542 mmol) in EtOH (2.5 mL) was added hydrazine monohydrate (20 wt %, 0.130 mL, 0.542 mmol) at room temperature. The reaction mixture was refluxed for 2 hours and cooled to room temperature. After filtered through a Celite pad while washing with MeOH, the filtrate was concentrated in vacuo. The residual solid was purified by recrystallization from MeOH and diethyl ether to give 5-(3-methyl-1-(tetrahydro-2H-pyran-2-yl)-1H-indazol-5-yl)-4-(6-methylpyridin-2-yl)-1H-imidazol-2-amine (210 mg, >99%) as a brown solid. MS: 389.2 [M+H]$^+$ Step D: (E)-1-(2-fluorophenyl)-N-(4-(3-methyl-1-(tetrahydro-2H-pyran-2-yl)-1H-indazol-5-yl)-5-(6-methylpyridin-2-yl)-1H-imidazol-2-yl)methanimine To a mixture of 5-(3-methyl-1-(tetrahydro-2H-pyran-2-yl)-1H-indazol-5-yl)-4-(6-methyl-pyridin-2-yl)-1H-imidazol-2-amine (210 mg, 0.541 mmol) and 2-fluorobenzaldehyde (0.200 mL, 1.90 mmol) in MeOH (4.0 mL) was added AcOH (0.100 mL, 1.75 mmol) at room temperature. The reaction mixture was refluxed for 15 hours and then concentrated in vacuo to give (E)-1-(2-fluorophenyl)-N-(4-(3- methyl-1-(tetrahydro-2H-pyran-2-yl)-1H-indazol-5-yl)-5-(6-methyl pyridin-2-yl)-1H-imidazol-2-yl)methanimine as a crude brown oil, which was used next reaction without further purification. MS: 495.2 [M+H]$^+$.

Step E: N-(2-fluorobenzyl)-4-(3-methyl-1-(tetrahydro-2H-pyran-2-yl)-1H-indazol-5-yl)-5-(6-methylpyridin-2-yl)-1H-imidazol-2-amine To a solution of crude (E)-1-(2-fluorophenyl)-N-(4-(3-methyl-1-(tetrahydro-2H-pyran-2-yl)-1H-indazol-5-yl)-5-(6-methylpyridin-2-yl)-1H-imidazol-2-yl)methanimine (260 mg, 0.526 mmol) in MeOH (5.2 mL) was added LiBH$_4$ (2.0 M in THF, 0.530 mL, 1.06 mmol) at 0° C. The reaction mixture was stirred at room temperature for 2 hours and quenched with water. The mixture was extracted with EtOAc twice, washed with brine, dried over Na$_2$SO$_4$, filtered, and concentrated in vacuo. The residue was purified by column chromatography on NH—SiO$_2$ (Hexanes: EtOAc=1:1 to EtOAc only) to give N-(2-fluorobenzyl)-4-(3-methyl-1-(tetrahydro-2H-pyran-2-yl)-1H-indazol-5-yl)-5-(6-methylpyridin-2-yl)-1H-imidazol-2-amine (113 mg, 43%) as a yellow oil. MS: 497.2 [M+H]$^+$ Step F: N-(2-fluorobenzyl)-4-(3-methyl-1H-indazol-5-yl)-5-(6-methylpyridin-2-yl)-1H-imidazol-2-amine To a solution of N-(2-fluorobenzyl)-4-(3-methyl-1-(tetrahydro-2H-pyran-2-yl)-1H-indazol-5-yl)-5-(6-methylpyridin-2-yl)-1H-imidazol-2-amine (113 mg, 0.228 mmol) in EtOH (2.0 mL) was added HCl (1 M solution in EtOAc, 0.460 mL, 0.460 mmol) at room temperature. The reaction mixture was refluxed for 3 hours and then concentrated in vacuo. The residue was neutralized with saturated aq. NaHCO$_3$ and then extracted with DCM twice. The combined organic layers were washed with brine, dried over Na$_2$SO$_4$, filtered, and concentrated in vacuo. The residue was purified by solidification from hexanes and DCM to give N-(2-fluorobenzyl)-4-(3-methyl-1H-indazol-5-yl)-5-(6-methylpyridin-2-yl)-1H-imidazol-2-amine (18 mg, 19%) as a yellow solid. $^1$H-NMR (400 MHz, DMSO-d$_6$): δ 11.01-10.58 (1H, m), 8.20-7.88 (1H, m), 7.63-7.28 (5H, m), 7.20-7.16 (2H, m), 7.04 (1H, d, J=8.0 Hz), 6.91 (1H, d, J=7.6 Hz), 6.13 (1H, t, J=6.4 Hz), 4.54 (2H, d, J=6.0 Hz), 2.45 (3H, s). MS: 413.1 [M+H]$^+$ Example 6: N-(3-fluorobenzyl)-4-(1H-indazol-5-yl)-5-(6-methylpyridin-2-yl)-1H-imidazol-2-amine

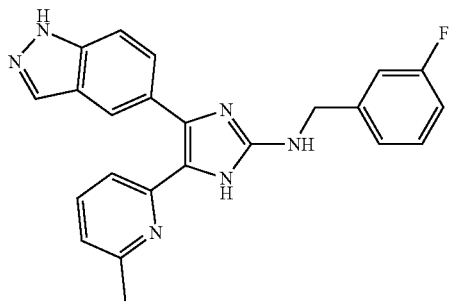 [SMILES: Cc1cccc(-c2[nH]c(NCc3cccc(F)c3)nc2-c2ccc3[nH]ncc3c2)n1]

Step A: N-(3-fluorobenzyl)-5-(6-methylpyridin-2-yl)-4-(1-(tetrahydro-2H-pyran-2-yl)-1H-indazol-5-yl)-1H-imidazol-2-amine N-(3-Fluorobenzyl)-5-(6-methylpyridin-2-yl)-4-(1-(tetrahydro-2H-pyran-2-yl)-1H-indazol-5-yl)-1H-imidazol-2-amine (115 mg, 44% for 2 steps) as a yellow solid was synthesized from 5-(6-methylpyridin-2-yl)-4-(1-(tetrahydro-2H-pyran-2-yl)-1H-indazol-5-yl)-1H-imidazol-2-amine (200 mg, 0.534 mmol) and 3-fluoro-benzaldehyde (0.170 mL, 1.60 mmol) by following the procedure for Example 1 (Step C). $^1$H-NMR (400 MHz, DMSO-d$_6$): δ 11.29-10.65 (1H, brs+brs), 8.10-8.09 (1H, m), 7.93 (1H, s), 7.77-7.56 (3H, m), 7.44-7.35 (2H, m), 7.24-7.23 (1H, m), 7.08-7.04 (2H, m), 6.97-6.92 (1H, m), 6.37-6.26 (1H, t+t), 5.84 (1H, d, J=10.4 Hz), 4.51 (2H, d, J=6.8 Hz), 3.91-3.73 (2H, m), 2.47-2.31 (3H, brs+brs), 2.05-1.96 (2H, m), 1.80-1.58 (4H, m). MS: 483.1 [M+H]$^+$ Step B: N-(3-fluorobenzyl)-4-(1H-indazol-5-yl)-5-(6-methylpyridin-2-yl)-1H-imidazol-2-amine N-(3-Fluorobenzyl)-4-(1H-indazol-5-yl)-5-(6-methylpyridin-2-yl)-1H-imidazol-2-amine (74.0 mg, 78%) as a pale yellow solid was synthesized from N-(3-fluorobenzyl)-5-(6-methylpyridin-2-yl)-4-(1-(tetrahydro-2H-pyran-2-yl)-1H-indazol-5-yl)-1H-imidazol-2-amine (115 mg, 0.238 mmol) by following the procedure for Example 7 (Step D). $^1$H-NMR (400 MHz, DMSO-d$_6$): δ 11.07-10.61 (1H, brs+brs), 8.06-8.04 (1H, m), 8.06-7.90 (1H, brs+brs), 7.67-7.04 (1H, d+d), 7.57-7.35 (4H, m), 7.24-7.19 (2H, m), 7.08-7.05 (1H, m), 6.94-6.91 (1H, d+d), 6.32-6.23 (1H, t+t), 4.51-4.47 (2H, d+d), 2.46-2.28 (3H, brs+brs). MS: 399.1 [M+H]$^+$ Example 7: N-(3,4-dichlorobenzyl)-4-(1H-indazol-5-yl)-5-(6-methylpyridin-2-yl)-1H-imidazol-2-amine

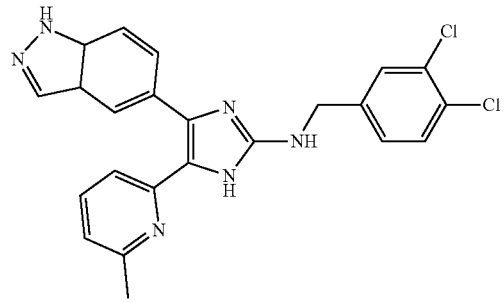 [SMILES: Cc1cccc(-c2[nH]c(NCc3ccc(Cl)c(Cl)c3)nc2C2=CC3C=NNC3C=C2)n1]

Step A: N-(3,4-dichlorobenzyl)-5-(6-methylpyridin-2-yl)-4-(1-(tetrahydro-2H-pyran-2-yl)-1H-indazol-5-yl)-1H-imidazol-2-amine N-(3,4-Dichlorobenzyl)-5-(6-methylpyridin-2-yl)-4-(1-(tetrahydro-2H-pyran-2-yl)-1H-indazol-5-yl)-1H-imidazol-2-amine (115 mg, 44% for 2 steps) as a yellow solid was synthesized from 5-(6-methylpyridin-2-yl)-4-(1-(tetrahydro-2H-pyran-2-yl)-1H-indazol-5-yl)-1H-imidazol-2-amine (200 mg, 0.534 mmol) and 3,4-dichloro-benzaldehyde (280 mg, 1.60 mmol) by following the procedure for Example 1 (Step C). $^1$H-NMR (400 MHz, DMSO-d$_6$): δ 11.16-10.71 (1H, brs+brs), 8.10-8.08 (1H, m), 7.92 (1H, s), 7.70-7.55 (4H, m), 7.43-7.38 (2H, m), 7.05 (1H, d, J=8.0

Hz), 6.95-6.92 (1H, m), 6.44-6.32 (1H, t+t), 5.83 (1H, dd, J=9.6, 2.0 Hz), 4.49-4.44 (2H, m), 3.91-3.73 (2H, m), 2.47-2.30 (3H, brs+brs), 2.06-1.95 (2H, m), 1.77-1.57 (4H, m). MS: 533 [M+H]$^+$.

Step B: N-(3,4-dichlorobenzyl)-4-(1H-indazol-5-yl)-5-(6-methylpyridin-2-yl)-1H-imidazol-2-amine N-(3,4-Dichlorobenzyl)-4-(1H-indazol-5-yl)-5-(6-methylpyridin-2-yl)-1H-imidazol-2-amine (82.7 mg, 61%) as a yellow solid was synthesized from N-(3,4-dichlorobenzyl)-5-(6-methylpyridin-2-yl)-4-(1-(tetrahydro-2H-pyran-2-yl)-1H-indazol-5-yl)-1H-imidazol-2-amine (160 mg, 0.300 mmol) by following the procedure for Example 7 (Step D). $^1$H-NMR (400 MHz, DMSO-d$_6$): δ 11.12-10.66 (1H, brs+brs), 8.06-8.04 (1H, m), 8.06-7.90 (1H, brs+brs), 7.69-7.04 (1H, d+d), 7.68-7.66 (1H, m), 7.60-7.58 (1H, m), 7.55-7.38 (4H, m), 6.94-6.92 (1H, d+d), 6.40-6.29 (1H, t+t), 4.48-4.44 (2H, d+d), 2.46-2.28 (3H, brs+brs). MS: 449.1 [M+H]$^+$.

Example 8: N-(2,3-difluorobenzyl)-5-yl)-5-(6-methylpyridin-2-yl)-1H-imidazol-2-amine

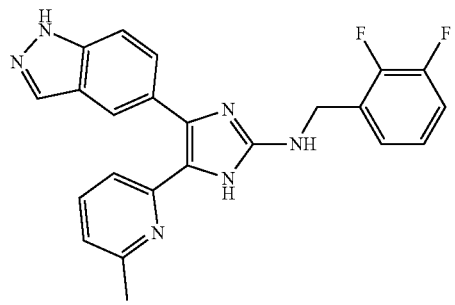 [SMILES: Cc1cccc(-c2[nH]c(NCc3cccc(F)c3F)nc2-c2ccc3[nH]ncc3c2)n1]

Step A: N-(2,3-difluorobenzyl)-5-(6-methylpyridin-2-yl)-4-(1-(tetrahydro-2H-pyran-2-yl)-1H-indazol-5-yl)-1H-imidazol-2-amine N-(2,3-Difluorobenzyl)-5-(6-methylpyridin-2-yl)-4-(1-(tetrahydro-2H-pyran-2-yl)-1H-indazol-5-yl)-1H-imidazol-2-amine (153 mg, 57% for 2 steps) as a yellow solid was synthesized from 5-(6-methylpyridin-2-yl)-4-(1-(tetrahydro-2H-pyran-2-yl)-1H-indazol-5-yl)-1H-imidazol-2-amine (200 mg, 0.534 mmol) and 2,3-difluoro-benzaldehyde (0.180 mL, 1.64 mmol) by following the procedure for Example 1 (Step C). $^1$H-NMR (400 MHz, DMSO-d$_6$): δ 11.10-10.67 (1H, brs+brs), 8.10-8.09 (1H, m), 7.92 (1H, s), 7.69-7.55 (2H, m), 7.42 (1H, t, J=8.0 Hz), 7.34-7.28 (2H, m), 7.21-7.16 (1H, m), 7.05 (1H, t, J=8.4 Hz), 6.96-6.93 (1H, d+d), 6.31-6.24 (1H, t+t), 5.83 (1H, dd, J=9.6, 2.0 Hz), 4.95-4.55 (2H, m), 3.91-3.71 (2H, m), 2.46-2.30 (3H, brs+brs), 2.06-1.95 (2H, m), 1.80-1.58 (4H, m). MS: 501.1 [M+H]$^+$.

Step B: N-(2,3-difluorobenzyl)-4-(1H-indazol-5-yl)-5-(6-methylpyridin-2-yl)-1H-imidazol-2-amine N-(2,3-Difluorobenzyl)-4-(1H-indazol-5-yl)-5-(6-methylpyridin-2-yl)-1H-imidazol-2-amine was synthesized (108 mg, 85%) as a yellow solid from N-(2,3-difluorobenzyl)-5-(6-methylpyridin-2-yl)-4-(1-(tetrahydro-2H-pyran-2-yl)-1H-indazol-5-yl)-1H-imidazol-2-amine (138 mg, 0.276 mmol) by following the procedure for Example 7 (Step D). $^1$H-NMR (400 MHz, DMSO-d$_6$): δ 11.09-10.64 (1H, brs+brs), 8.06-8.04 (1H, m), 8.06-7.90 (1H, brs+brs), 7.67-7.04 (1H, d+d), 7.58-7.28 (5H, m), 7.21-7.16 (1H, m), 6.94-6.92 (1H, d+d), 6.30-6.22 (1H, t+t), 4.59-4.55 (2H, m), 2.46-2.28 (3H, brs+brs). MS: 417.1 [M+H]$^+$.

Example 9: N-(2,4-difluorobenzyl)-4-(1H-indazol-5-yl)-5-(6-methylpyridin-2-yl)-1H-imidazol-2-amine

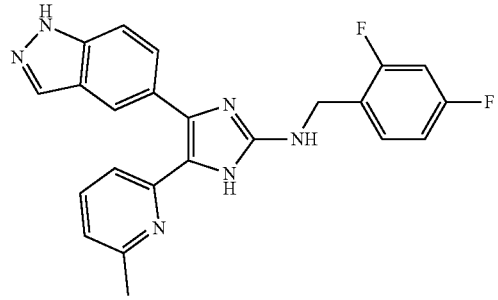 [SMILES: Cc1cccc(-c2[nH]c(NCc3ccc(F)cc3F)nc2-c2ccc3[nH]ncc3c2)n1]

Step A: N-(2,4-difluorobenzyl)-5-(6-methylpyridin-2-yl)-4-(1-(tetrahydro-2H-pyran-2-yl)-1H-indazol-5-yl)-1H-imidazol-2-amine N-(2,4-Difluorobenzyl)-5-(6-methylpyridin-2-yl)-4-(1-(tetrahydro-2H-pyran-2-yl)-1H-indazol-5-yl)-1H-imidazol-2-amine (138 mg, 51% for 2 steps) as a yellow solid was synthesized from 5-(6-methylpyridin-2-yl)-4-(1-(tetrahydro-2H-pyran-2-yl)-1H-indazol-5-yl)-1H-imidazol-2-amine (200 mg, 0.534 mmol) and 2,4-difluoro-benzaldehyde (0.180 mL, 1.64 mmol) by following the procedure for Example 1 (Step C). $^1$H-NMR (400 MHz, DMSO-d$_6$): δ 11.10-10.64 (1H, brs+brs), 8.10-8.09 (1H, m), 7.93 (1H, s), 7.69-7.50 (3H, m), 7.42 (1H, t, J=8.0 Hz), 7.25-7.19 (1H, m), 7.09-7.04 (2H, m), 6.97-6.92 (1H, m), 6.25-6.16 (1H, t+t), 5.83 (1H, dd, J=9.6, 2.0 Hz), 4.50-4.47 (2H, m), 3.91-3.71 (2H, m), 2.46-2.31 (3H, brs+brs), 2.06-1.95 (2H, m), 1.80-1.58 (4H, m). MS: 501.1 [M+H]$^+$.

Step B: N-(2,4-difluorobenzyl)-4-(1H-indazol-5-yl)-5-(6-methylpyridin-2-yl)-1H-imidazol-2-amine N-(2,4-Difluorobenzyl)-4-(1H-indazol-5-yl)-5-(6-methylpyridin-2-yl)-1H-imidazol-2-amine (90 mg, 78%) as a yellow solid was synthesized from N-(2,4-difluorobenzyl)-5-(6-methylpyridin-2-yl)-4-(1-(tetrahydro-2H-pyran-2-yl)-1H-indazol-5-yl)-1H-imidazol-2-amine (138 mg, 0.276 mmol) by following the procedure for Example 7 (Step D). $^1$H-NMR (400 MHz, DMSO-d$_6$): δ 11.08-10.61 (1H, brs+brs), 8.07-8.05 (1H, brs+brs), 8.05-7.90 (1H, brs+brs), 7.67-7.04 (1H, d+d), 7.58-7.38 (4H, m), 7.25-7.19 (1H, m), 7.09-7.07 (1H, m), 6.95-6.91 (1H, d+d), 6.22-6.15 (1H, t+t), 4.50-4.47 (2H, m), 2.46-2.29 (3H, brs+brs). MS: 417.1 [M+H]$^+$.

Example 10: N-(4-chloro-2-fluorobenzyl)-4-(1H-indazol-5-yl)-5-(6-methylpyridin-2-yl)-1H-imidazol-2-amine

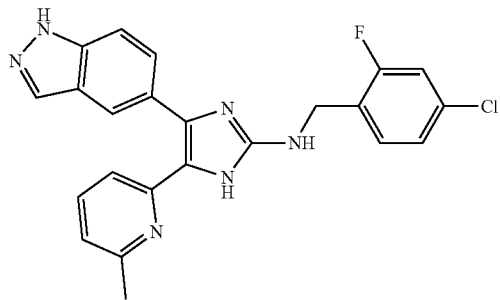 [SMILES: Cc1cccc(-c2[nH]c(NCc3ccc(Cl)cc3F)nc2-c2ccc3[nH]ncc3c2)n1]

Step A: N-(4-chloro-2-fluorobenzyl)-5-(6-methylpyridin-2-yl)-4-(1-(tetrahydro-2H-pyran-2-yl)-1H-indazol-5-yl)-1H-imidazol-2-amine N-(4-Chloro-2-fluorobenzyl)-5-(6-methylpyridin-2-yl)-4-(1-(tetrahydro-2H-pyran-2-yl)-1H-indazol-5-yl)-1H-imidazol-2-amine (170 mg, 61% for 2 steps) as a yellow solid was synthesized from 5-(6-methylpyridin-2-yl)-4-(1-(tetrahydro-2H-pyran-2-yl)-1H-indazol-5-yl)-1H-imidazol-2-amine (200 mg, 0.534 mmol) and 4-chloro-2-fluoro-benzaldehyde (254 mg, 1.60 mmol) by following the procedure for Example 1 (Step C). $^1$H-NMR (400 MHz, DMSO-d$_6$): δ 11.10-10.67 (1H, brs+brs), 8.10-8.09 (1H, m), 7.92 (1H, s), 7.69-7.48 (3H, m), 7.44-7.39 (2H, m), 7.28 (1H, dd, J=8.4, 2.0 Hz), 7.05 (1H, d, J=8.4 Hz), 6.96-6.93 (1H, d+d), 6.28-6.20 (1H, t+t), 5.84 (1H, dd, J=9.6, 2.4 Hz), 4.52-4.48 (2H, m), 3.92-3.71 (2H, m), 2.46-2.30 (3H, brs+brs), 2.06-1.96 (2H, m), 1.80-1.57 (4H, m). MS: 517.0 [M+H]$^+$ Step B: N-(4-chloro-2-fluorobenzyl)-4-(1H-indazol-5-yl)-5-(6-methylpyridin-2-yl)-1H-imidazol-2-amine N-(4-Chloro-2-fluorobenzyl)-4-(1H-indazol-5-yl)-5-(6-methylpyridin-2-yl)-1H-imidazol-2-amine (122 mg, 86%) as a yellow solid was synthesized from N-(4-chloro-2-fluorobenzyl)-5-(6-methylpyridin-2-yl)-4-(1-(tetrahydro-2H-pyran-2-yl)-1H-indazol-5-yl)-1H-imidazol-2-amine (170 mg, 0.329 mmol) by following the procedure for Example 7 (Step D). $^1$H-NMR (400 MHz, DMSO-d$_6$): δ 11.08-10.64 (1H, brs+brs), 8.06-8.04 (1H, brs+brs), 8.04-7.89 (1H, brs+brs), 7.67-7.04 (1H, d+d), 7.57-7.38 (5H, m), 7.30-7.27 (1H, m), 6.94-6.91 (1H, d+d), 6.26-6.18 (1H, t+t), 4.52-4.48 (2H, m), 2.46-2.28 (3H, brs+brs). MS: 433.0 [M+H]$^+$.

Example 11: N-(3-chloro-2-fluorobenzyl)-4-(1H-indazol-5-yl)-5-(6-methylpyridin-2-yl)-1H-imidazol-2-amine

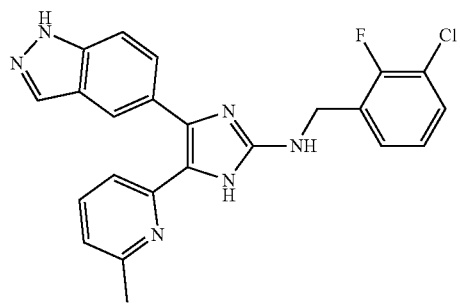 [SMILES: Cc1cccc(-c2[nH]c(NCc3cccc(Cl)c3F)nc2-c2ccc3[nH]ncc3c2)n1]

Step A: N-(3-chloro-2-fluorobenzyl)-5-(6-methylpyridin-2-yl)-4-(1-(tetrahydro-2H-pyran-2-yl)-1H-indazol-5-yl)-1H-imidazol-2-amine N-(3-Chloro-2-fluorobenzyl)-5-(6-methylpyridin-2-yl)-4-(1-(tetrahydro-2H-pyran-2-yl)-1H-indazol-5-yl)-1H-imidazol-2-amine (174 mg, 63% for 2 steps) as a yellow solid was synthesized from 5-(6-methylpyridin-2-yl)-4-(1-(tetrahydro-2H-pyran-2-yl)-1H-indazol-5-yl)-1H-imidazol-2-amine (200 mg, 0.534 mmol) and 3-chloro-2-fluoro-benzaldehyde (0.190 mL, 1.61 mmol) by following the procedure for Example 1 (Step C). $^1$H-NMR (400 MHz, DMSO-d$_6$): δ 11.14-10.69 (1H, brs+brs), 8.10-8.08 (1H, m), 7.92 (1H, s), 7.68-7.40 (5H, m), 7.21 (1H, t, J=8.0 Hz), 7.05 (1H, d, J=8.4 Hz), 6.96-6.93 (1H, d+d), 6.37-6.27 (1H, t+t), 5.83 (1H, dd, J=9.6, 2.0 Hz), 4.58-4.54 (2H, m), 3.91-3.71 (2H, m), 2.46-2.30 (3H, brs+brs), 2.06-1.95 (2H, m), 1.80-1.57 (4H, m). MS: 517.1 [M+H]$^+$.

Step B: N-(3-chloro-2-fluorobenzyl)-4-(1H-indazol-5-yl)-5-(6-methylpyridin-2-yl)-1H-imidazol-2-amine N-(3-Chloro-2-fluorobenzyl)-4-(1H-indazol-5-yl)-5-(6-methylpyridin-2-yl)-1H-imidazol-2-amine (115 mg, 79%) as a yellow solid was synthesized from N-(3-chloro-2-fluorobenzyl)-5-(6-methylpyridin-2-yl)-4-(1-(tetrahydro-2H-pyran-2-yl)-1H-indazol-5-yl)-1H-imidazol-2-amine (174 mg, 0.337 mmol) by following the procedure for Example 7 (Step D). $^1$H-NMR (400 MHz, DMSO-d$_6$): δ 11.10-10.65 (1H, brs+brs), 8.06-8.04 (1H, m), 8.04-7.89 (1H, brs+brs), 7.67-7.04 (1H, d+d), 7.54-7.38 (5H, m), 7.21 (1H, t, J=8.0 Hz), 7.04 (1H, d, J=7.6 Hz), 6.94-6.92 (1H, d+d), 6.34-6.24 (1H, t+t), 4.58-4.54 (2H, m), 2.46-2.28 (3H, brs+brs). MS: 433.0 [M+H]$^+$.

Example 12: N-(3,4-difluorobenzyl)-4-(1H-indazol-5-yl)-5-(6-methylpyridin-2-yl)-1H-imidazol-2-amine

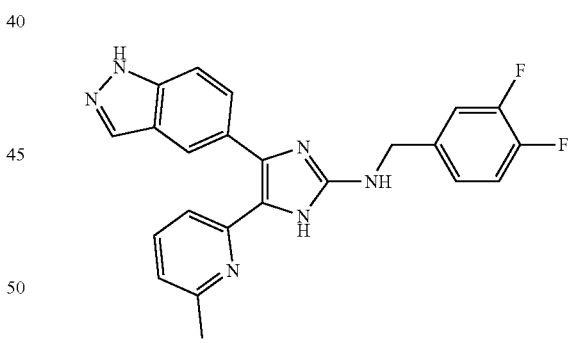

Step A: N-(3,4-difluorobenzyl)-4-(1H-indazol-5-yl)-5-(6-methylpyridin-2-yl)-1H-imidazol-2-amine N-(3,4-Difluorobenzyl)-4-(1H-indazol-5-yl)-5-(6-methylpyridin-2-yl)-1H-imidazol-2-amine (167 mg, 62% for 2 steps) as a yellow solid was synthesized from 5-(6-methylpyridin-2-yl)-4-(1-(tetrahydro-2H-pyran-2-yl)-1H-indazol-5-yl)-1H-imidazol-2-amine (200 mg, 0.534 mmol) and 3,4-difluoro-benzaldehyde (0.180 mL, 1.63 mmol) by following the procedure for Example 1 (Step C). $^1$H-NMR (400 MHz, DMSO-d$_6$): δ 11.09-10.66 (1H, brs+brs), 8.10-8.09 (1H, m), 7.93 (1H, s), 7.68 (1H, d, J=8.8 Hz), 7.56 (1H, dd, J=8.8, 1.6 Hz), 7.47-7.37 (3H, m), 7.28-7.28 (1H, m), 7.05

(1H, d, J=8.4 Hz), 6.96-6.93 (1H, d+d), 6.34-6.25 (1H, t+t), 5.83 (1H, dd, J=10.4, 2.4 Hz), 4.47-4.44 (2H, d+d), 3.92-3.71 (2H, m), 2.47-2.06 (3H, brs+brs), 2.06-1.94 (2H, m), 1.79-1.56 (4H, m). MS: 501.1 [M+H]$^+$ Step B: N-(3,4-difluorobenzyl)-4-(1H-indazol-5-yl)-5-(6-methylpyridin-2-yl)-1H-imidazol-2-amine N-(3,4-Difluorobenzyl)-4-(1H-indazol-5-yl)-5-(6-methylpyridin-2-yl)-1H-imidazol-2-amine (113 mg, 81%) as a yellow solid was synthesized from N-(3,4-difluorobenzyl)-4-(1H-indazol-5-yl)-5-(6-methylpyridin-2-yl)-1H-imidazol-2-amine (167 mg, 0.334 mmol) by following the procedure for Example 7 (Step D). $^1$H-NMR (400 MHz, DMSO-d$_6$): δ 11.04-10.61 (1H, brs+brs), 8.06-8.04 (1H, brs+brs), 8.04-7.90 (1H, brs+brs), 7.67-7.04 (1H, d+d), 7.58-7.35 (5H, m), 7.29-7.23 (1H, m), 6.95-6.91 (1H, d+d), 6.30-6.22 (1H, t+t), 4.47-4.43 (2H, d+d), 2.46-2.28 (3H, brs+brs). MS: 417.1 [M+H]$^+$.

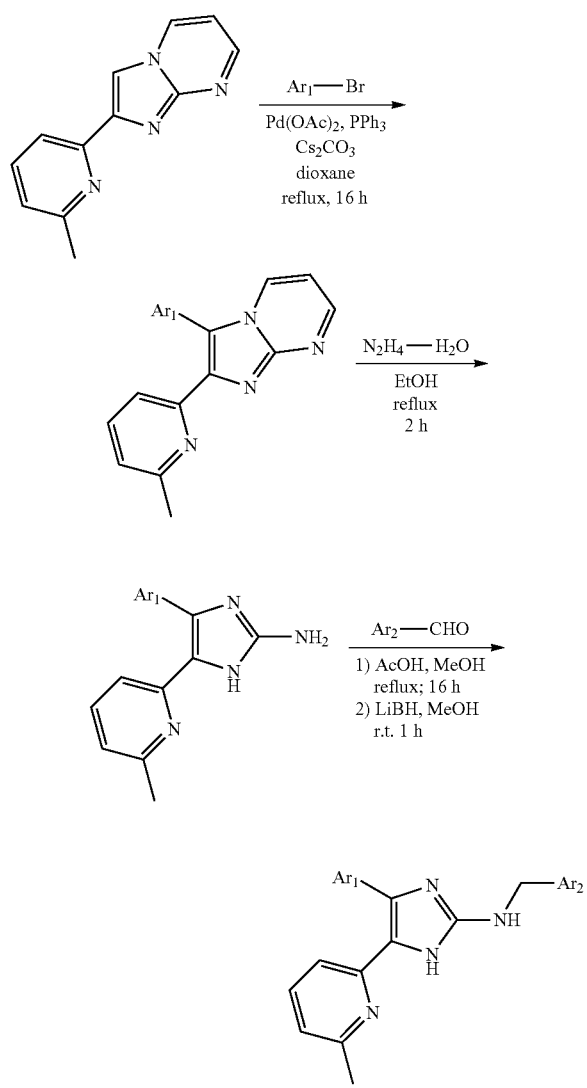

Example 13: N-(3-fluorobenzyl)-4-(1-methyl-1H-indazol-5-yl)-5-(6-methylpyridin-2-yl)-1H-imidazol-2-amine

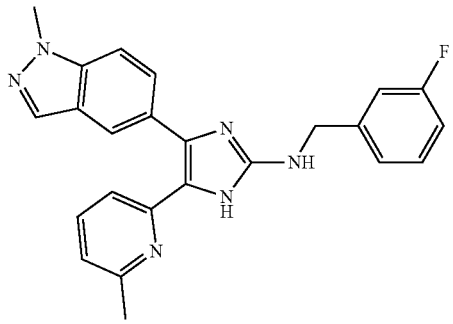

Step A: 3-(1-methyl-1H-indazol-5-yl)-2-(6-methylpyridin-2-yl)imidazo[1,2-a]pyrimidine A mixture of 2-(6-methylpyridin-2-yl)imidazo[1,2-a]pyrimidine (Intermediate 16, 1.42 g, 6.78 mmol), 5-bromo-1-methyl-1H-indazole (Intermediate 6, 1.43 g, 6.78 mmol), Pd(OAc)$_2$ (122 mg, 0.542 mmol), PPh$_3$ (284 mg, 1.08 mmol) and Cs$_2$CO$_3$ (2.42 g, 7.45 mmol) in dioxane (24 mL) was degassed by purging and re-filled with Ar in several times. The reaction mixture was refluxed for 4 hours and cooled to room temperature. After dilution with DCM, the mixture was filtered through a Celite pad. The filtrate was partitioned between DCM and water. The separated aqueous layer was extracted with DCM. The combined organic layers were washed with brine, dried over Na$_2$SO$_4$, filtered, and concentrated in vacuo. The residual solid was purified by recrystallization from DCM and diethyl ether to afford 3-(1-methyl-1H-indazol-5-yl)-2-(6-methylpyridin-2-yl)imidazo[1,2-a]pyrimidine (2.30 g, crude) as a pale brown solid. MS: 341.1 [M+H]$^+$.

Step B: 4(1-methyl-1H-indazol-5-yl)-5-(6-methylpyridin-2-yl)-1H-imidazol-2-amine To a solution of 3-(1-methyl-1H-indazol-5-yl)-2-(6-methylpyridin-2-yl)imidazo[1,2-a]pyrimidine (2.30 g, crude) in EtOH (28 mL) was added hydrazine monohydrate (20 wt %, 1.70 mL, 7.01 mmol) at room temperature. The reaction mixture was refluxed for 1 hour and cooled to room temperature. After filtered through a Celite pad while washing with MeOH, the filtrate was concentrated in vacuo. The residue was purified by crystallization from Et$_2$O and MeOH to give 4-(1-methyl-1H-indazol-5-yl)-5-(6-methylpyridin-2-yl)-1H-imidazol-2-amine (1.06 g, 51% for 2 steps) as a yellow solid. $^1$H-NMR (400 MHz, DMSO-d$_6$): δ 10.51 (1H, brs), 8.01 (1H, s), 7.92 (1H, s), 7.58 (2H, s), 7.41 (1H, s), 7.07 (1H, brs), 6.90 (1H, d, J=7.6 Hz), 5.42 (2H, brs), 4.04 (3H, s), 2.43 (3H, s). MS: 305.1 [M+H]$^+$ Step C: N-(3-fluorobenzyl)-4-(1-methyl-1H-indazol-5-yl)-5-(6-methylpyridin-2-yl)-1H-imidazol-2-amine A mixture of 4-(1-methyl-1H-indazol-5-yl)-5-(6-methylpyridin-2-yl)-1H-imidazol-2-amine (200 mg, 0.657 mmol), 3-fluoro-benzaldehyde (0.210 mL, 1.98 mmol) and acetic acid (0.0200 mL, 0.349 mmol) in MeOH (4.0 mL)

was refluxed for 3 hours and cooled to room temperature. After addition of LiBH$_4$ (2 M solution in THF, 0.660 mL, 1.32 mmol) at room temperature, the reaction mixture was stirred at room temperature for 1 hour and quenched with saturated aq. NH$_4$Cl. The mixture was extracted with DCM, washed with brine, dried over Na$_2$SO$_4$, filtered, and concentrated in vacuo. The residue was purified by column chromatography on NH—SiO$_2$ (DCM:MeOH=95:5) to afford N-(3-fluorobenzyl)-4-(1-methyl-1H-indazol-5-yl)-5-(6-methylpyridin-2-yl)-1H-imidazol-2-amine (134 mg, 49% for 2 steps) as a yellow solid. $^1$H-NMR (400 MHz, DMSO-d$_6$): δ 11.06-10.62 (1H, brs+brs), 8.06-8.02 (1H, brs+brs), 8.03-7.90 (1H, brs+brs), 7.73-7.07 (1H, d+d), 7.60-7.20 (6H, m), 7.04-7.02 (1H, m), 6.95-6.92 (1H, d+d), 6.31-6.23 (1H, t+t), 4.51-4.47 (2H, d+d), 4.04 (3H, s), 2.46-2.29 (3H, brs+brs). MS: 413.1 [M+H]$^+$.

Example 14: N-(4-fluorobenzyl)-4-(1-methyl-1H-indazol-5-yl)-5-(6-methylpyridin-2-yl)-1H-imidazol-2-amine

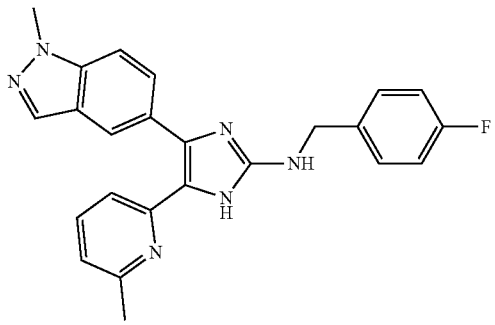 [SMILES: Cc1cccc(-c2[nH]c(NCc3ccc(F)cc3)nc2-c2ccc3c(cnn3C)c2)n1]

Step A: N-(4-fluorobenzyl)-4-(1-methyl-1H-indazol-5-yl)-5-(6-methylpyridin-2-yl)-1H-imidazol-2-amine N-(4-Fluorobenzyl)-4-(1-methyl-1H-indazol-5-yl)-5-(6-methylpyridin-2-yl)-1H-imidazol-2-amine (116 mg, 57% for two steps) as a yellow solid was synthesized from 4-(1-methyl-1H-indazol-5-yl)-5-(6-methylpyridin-2-yl)-1H-imidazol-2-amine (150 mg, 0.493 mmol) and 4-fluoro-benzaldehyde (0.160 mL, 1.52 mmol) by following the procedure for Example 13 (Step C). $^1$H-NMR (400 MHz, DMSO-d$_6$): δ 11.05-10.58 (1H, brs+brs), 8.06-8.02 (1H, brs+brs), 8.03-7.90 (1H, brs+brs), 7.73-7.03 (1H, d+d), 7.60-7.38 (5H, m), 7.17-7.13 (2H, d+d), 6.95-6.91 (1H, d+d), 6.27-6.16 (1H, t+t), 4.46-4.43 (2H, d+d), 4.04-4.03 (3H, brs+brs), 2.46-2.29 (3H, brs+brs). MS: 413.1 [M+H]$^+$.

Example 15: N-(4-chloro-3-fluorobenzyl)-4-(1-methyl-1H-indazol-5-yl)-5-(6-methylpyridin-2-yl)-1H-imidazol-2-amine

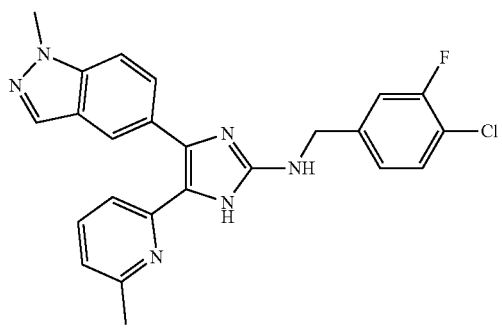 [SMILES: Cc1cccc(-c2[nH]c(NCc3ccc(Cl)c(F)c3)nc2-c2ccc3c(cnn3C)c2)n1]

N-(4-Chloro-3-fluorobenzyl)-4-(1-methyl-1H-indazol-5-yl)-5-(6-methyl-pyridin-2-yl)-1H-imidazol-2-amine (111 mg, 60% for two steps) as a yellow solid was synthesized from 4-(1-methyl-1H-indazol-5-yl)-5-(6-methylpyridin-2-yl)-1H-imidazol-2-amine (180 mg, 0.405 mmol) and 4-fluoro-benzaldehyde (0.160 mL, 1.52 mmol) by following the procedure for Example 13 (Step C). $^1$H-NMR (400 MHz, DMSO-d$_6$): δ 11.09-10.67 (1H, brs+brs), 8.06-8.02 (1H, brs+brs), 8.03-7.89 (1H, brs+brs), 7.73-7.03 (1H, d+d), 7.59-7.38 (5H, m), 7.31-7.25 (1H, m), 6.95-6.92 (1H, d+d), 6.36-6.28 (1H, t+t), 4.49-4.46 (2H, d+d), 4.04-4.03 (3H, brs+brs), 2.46-2.29 (3H, brs+brs). MS: 447.1 [M+H]$^+$.

Example 16: 4-(1-ethyl-1H-indazol-5-yl)-N-(3-fluorobenzyl)-5-(6-methylpyridin-2-yl)-1H-imidazol-2-amine

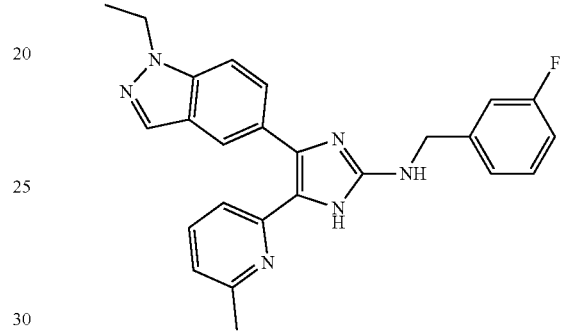

Step A: 3-(1-ethyl-1H-indazol-5-yl)-2-(6-methylpyridin-2-yl)imidazo[1,2-a]pyrimidine A mixture of 2-(6-methylpyridin-2-yl)imidazo[1,2-a]pyrimidine (Intermediate 16, 467 mg, 2.22 mmol), 5-bromo-1-ethyl-1H-indazole (Intermediate 7, 1.43 g, 6.78 mmol), Pd(OAc)$_2$ (40.0 mg, 0.178 mmol), PPh$_3$ (93.0 mg, 0.355 mmol) and Cs$_2$CO$_3$ (796 mg, 2.44 mmol) in dioxane (24.0 mL) was degassed by purging and re-filled with Ar in several times. The reaction mixture was refluxed for 4 hours and cooled to room temperature. After dilution with DCM, the mixture was filtered through a Celite pad. The filtrate was partitioned between DCM and water. The separated aqueous layer was extracted with DCM. The combined organic layers were washed with brine, dried over Na$_2$SO$_4$, filtered, and concentrated in vacuo. The residual solid was purified by recrystallization from DCM and diethyl ether to afford 3-(1-ethyl-1H-indazol-5-yl)-2-(6-methylpyridin-2-yl)imidazo[1,2-a]pyrimidine (795 mg) as a pale brown solid. MS: 355.1 [M+H]$^+$.

Step B: 4-(1-ethyl-1H-indazol-5-yl)-5-(6-methylpyridin-2-yl)-1H-imidazol-2-amine 4-(1-Ethyl-1H-indazol-5-yl)-5-(6-methylpyridin-2-yl)-1H-imidazol-2-amine (470 mg, 67% for 2 steps) as a yellow solid was synthesized from 3-(1-ethyl-1H-indazol-5-yl)-2-(6-methylpyridin-2-yl)imidazo[1,2-a]pyrimidine (787 mg, 2.22 mmol) by following the procedure for Example 13 (Step B). $^1$H-NMR (400 MHz, DMSO-d$_6$): δ 10.93-10.49 (1H, brs+brs), 8.03-7.89 (1H, brs+brs), 7.89-7.64 (1H, brs+brs), 7.75-7.05 (1H, d+d), 7.63 (1H, d, J=8.4 Hz), 7.54 (1H, d, J=8.8 Hz), 7.41 (1H, t, J=7.6 Hz), 7.37-7.06 (1H, m), 6.90 (1H, d, J=8.0 Hz), 5.46-5.28 (2H, brs+brs), 4.43 (2H, q, J=7.2 Hz), 2.49-2.29 (3H, brs+brs), 1.41 (3H, t, J=7.2 Hz). MS: 319.1 [M+H]$^+$ Step C: 4-(1-ethyl-1H-indazol-5-yl)-N-(3-fluorobenzyl)-5-(6-methylpyridin-2-yl)-1H-imidazol-2-amine 4-(1-Ethyl-1H-indazol-5-yl)-N-(3-fluorobenzyl)-5-(6-methylpyridin-2-yl)-1H-imidazol-2-amine (84 mg, 42% for 2 steps) as a yellow solid was synthesized from 4-(1-ethyl-1H-indazol-5-yl)-5-(6-methylpyridin-2-yl)-1H-imidazol-2-amine (150 mg, 0.471 mmol) and 3-fluorobenzaldehyde (0.150 mL, 1.413 mmol) by following the procedure for Example 13 (Step C). $^1$H-NMR (400 MHz, DMSO-$d_6$): δ 11.04-10.61 (1H, brs+brs), 8.08-8.03 (1H, brs+brs), 8.04-7.90 (1H, brs+brs), 7.72-7.04 (1H, brs+brs), 7.63-7.34 (4H, m), 7.27-7.20 (2H, m), 7.07-7.05 (1H, m), 6.96-6.91 (1H, d+d), 6.31-6.23 (1H, t+t), 4.50-4.47 (2H, d+d), 4.46-4.40 (2H, m), 2.46-2.30 (3H, brs+brs), 1.42-1.37 (3H, m). MS: 427.1 [M+H]$^+$.

Example 17: N-(2-fluoro-3-methylbenzyl)-4-(1-methyl-1H-indazol-5-yl)-5-(6-methylpyridin-2-yl)-1H-imidazol-2-amine

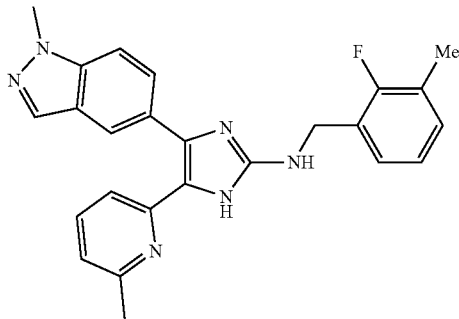 [SMILES: Cc1cccc(-c2[nH]c(NCc3cccc(C)c3F)nc2-c2ccc3c(cnn3C)c2)n1]

N-(2-Fluoro-3-methylbenzyl)-4-(1-methyl-1H-indazol-5-yl)-5-(6-methylpyridin-2-yl)-1H-imidazol-2-amine (108 mg, 51% for two steps) as a yellow solid was synthesized from 4-(1-methyl-1H-indazol-5-yl)-5-(6-methylpyridin-2-yl)-1H-imidazol-2-amine (150 mg 0.493 mmol) and 2-fluoro-3-methyl-benzaldehyde (0.180 mL, 1.48 mmol) by following the procedure for Example 13 (Step C). $^1$H-NMR (400 MHz, DMSO-$d_6$): δ 11.03-10.58 (1H, brs+brs), 8.06-8.02 (1H, brs+brs), 8.03-7.89 (1H, brs+brs), 7.73-7.03 (1H, d+d), 7.60-7.38 (3H, m), 7.34-7.26 (1H, m), 7.18-7.15 (1H, m), 7.07-7.05 (1H, m), 6.94-6.91 (1H, d+d), 6.14-6.11 (1H, t+t), 4.52-4.50 (2H, m), 4.04-4.03 (3H, brs+brs), 2.46-2.30 (3H, brs+brs), 2.24 (3H, s). MS: 427.1 [M+H]$^+$ Example 18: N-(2-fluoro-4-methylbenzyl)-4-(1-methyl-1H-indazol-5-yl)-5-(6-methylpyridin-2-yl)-1H-imidazol-2-amine

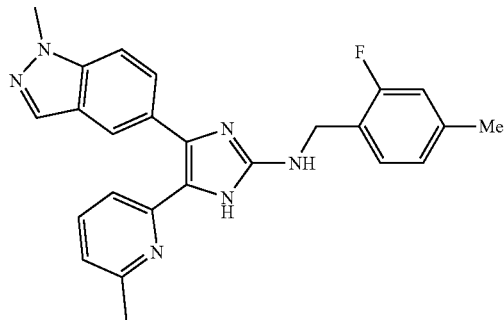 [SMILES: Cc1ccc(CNc2nc(-c3ccc4c(cnn4C)c3)c(-c3cccc(C)n3)[nH]2)c(F)c1]

N-(2-Fluoro-4-methylbenzyl)-4-(1-methyl-1H-indazol-5-yl)-5-(6-methylpyridin-2-yl)-1H-imidazol-2-amine (125 mg, 59% for two steps) as a yellow solid was synthesized from 4-(1-methyl-1H-indazol-5-yl)-5-(6-methylpyridin-2-yl)-1H-imidazol-2-amine (150 mg 0.493 mmol) and 2-fluoro-4-methyl-benzaldehyde (0.145 mL, 1.48 mmol) by following the procedure for Example 13 (Step C). $^1$H-NMR (400 MHz, DMSO-$d_6$): δ 11.04-10.57 (1H, brs+brs), 8.06-8.02 (1H, brs+brs), 8.03-7.90 (1H, brs+brs), 7.73-7.03 (1H, d+d), 7.60-7.33 (4H, m), 7.02-6.90 (3H, m), 6.12-6.07 (1H, t+t), 4.48-4.45 (2H, m), 4.05-4.03 (3H, brs+brs), 2.46-2.30 (3H, brs+brs), 2.28 (3H, s). MS: 427.1 [M+H]$^+$ Example 19: N-(3-fluoro-4-methylbenzyl)-4-(1-methyl-1H-indazol-5-yl)-5-(6-methyl-pyridine-2-yl)-1H-imidazol-2-amine

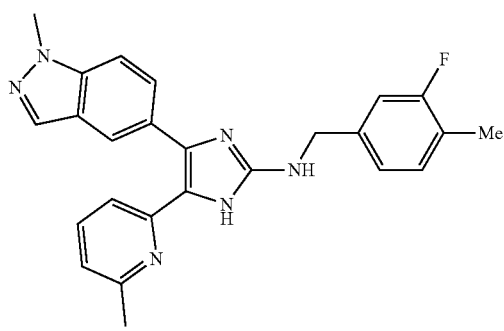 [SMILES: Cc1cccc(-c2[nH]c(NCc3ccc(C)c(F)c3)nc2-c2ccc3c(cnn3C)c2)n1]

N-(3-Fluoro-4-methylbenzyl)-4-(1-methyl-1H-indazol-5-yl)-5-(6-methylpyridin-2-yl)-1H-imidazol-2-amine (123 mg, 58% for two steps) as a yellow solid was synthesized from 4-(1-methyl-1H-indazol-5-yl)-5-(6-methylpyridin-2-yl)-1H-imidazol-2-amine (150 mg 0.493 mmol) and 3-fluoro-4-methyl-benzaldehyde (0.180 mL, 1.48 mmol) by following the procedure for Example 13 (Step C). $^1$H-NMR (400 MHz, DMSO-$d_6$): δ 11.04-10.59 (1H, brs+brs), 8.05-8.02 (1H, brs+brs), 8.03-7.90 (1H, brs+brs), 7.73-7.03 (1H, d+d), 7.60-7.38 (3H, m), 7.25-7.11 (2H, m), 6.93-6.92 (1H, d+d), 6.27-6.18 (1H, t+t), 4.45-4.42 (2H, m), 4.04-4.03 (3H, brs+brs), 2.46-2.29 (3H, brs+brs), 2.19 (3H, s). MS: 427.1 [M+H]$^+$ Example 20: 4-(1-methyl-1H-indazol-5-yl)-5-(6-methylpyridin-2-yl)-N-(2,3,4-trifluoro-benzyl)-1H-imidazol-2-amine

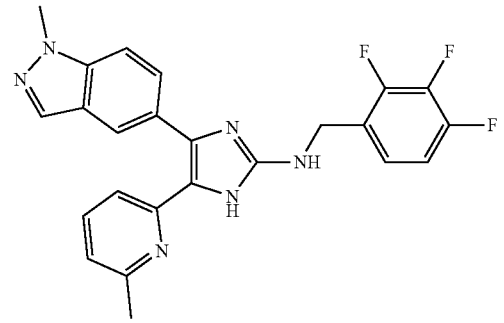 [SMILES: Cc1cccc(-c2[nH]c(NCc3ccc(F)c(F)c3F)nc2-c2ccc3c(cnn3C)c2)n1]

4-(1-Methyl-1H-indazol-5-yl)-5-(6-methylpyridin-2-yl)-N-(2,3,4-trifluorobenzyl)-1H-imidazol-2-amine (130 mg, 58% for two steps) as a yellow solid was synthesized from 4-(1-methyl-1H-indazol-5-yl)-5-(6-methylpyridin-2-yl)-1H-imidazol-2-amine (150 mg 0.493 mmol) and 2,3,4-trifluoro-benzaldehyde (0.170 mL, 1.50 mmol) by following the procedure for Example 13 (Step C). ¹H-NMR (400 MHz, DMSO-d₆): δ 11.13-10.69 (1H, brs+brs), 8.06-8.02 (1H, brs+brs), 8.03-7.89 (1H, brs+brs), 7.73-7.03 (1H, d+d), 7.60-7.26 (5H, m), 7.25-7.11 (2H, m), 6.95-6.93 (1H, d+d), 6.34-6.25 (1H, t+t), 4.45-4.41 (2H, m), 4.04-4.03 (3H, brs+brs), 2.46-2.29 (3H, brs+brs). MS: 449.1 [M+H]⁺

Example 21: N-(3,4-difluorobenzyl)-4-(1-methyl-1H-indazol-5-yl)-5-(6-methylpyridin-2-yl)-1H-imidazol-2-amine

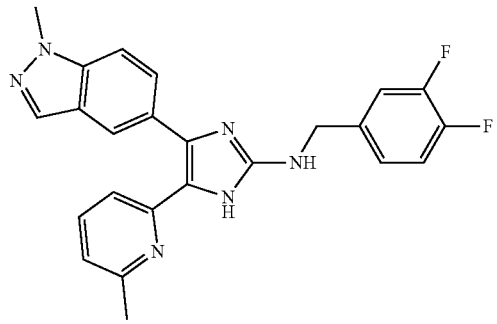 [SMILES: Cc1cccc(-c2[nH]c(NCc3ccc(F)c(F)c3)nc2-c2ccc3c(cnn3C)c2)n1]

N-(3,4-Difluorobenzyl)-4-(1-methyl-1H-indazol-5-yl)-5-(6-methylpyridin-2-yl)-1H-imidazol-2-amine (86.0 mg, 40% for two steps) as a yellow solid was synthesized from 4-(1-methyl-1H-indazol-5-yl)-5-(6-methylpyridin-2-yl)-1H-imidazol-2-amine (150 mg 0.493 mmol) and 3,4-difluoro-benzaldehyde (0.170 mL, 1.54 mmol) by following the procedure for Example 13 (Step C). ¹H-NMR (400 MHz, DMSO-d₆): δ 11.08-10.65 (1H, brs+brs), 8.06-8.02 (1H, brs+brs), 8.03-7.90 (1H, brs+brs), 7.73-7.03 (1H, d+d), 7.60-7.23 (6H, m), 6.95-6.92 (1H, d+d), 6.33-6.24 (1H, t+t), 4.47-4.43 (2H, m), 4.04 (3H, s), 2.46-2.29 (3H, brs+brs). MS: 431.1 [M+H]⁺.

Example 22: N-(3-fluorobenzyl)-5-(6-methylpyridin-2-yl)-4-(1-(methylsulfonyl)-1H-indazol-5-yl)-1H-imidazol-2-amine

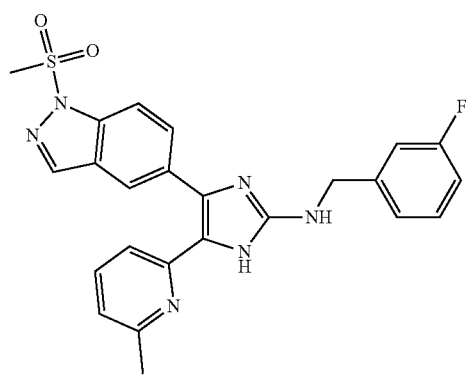 [SMILES: Cc1cccc(-c2[nH]c(NCc3cccc(F)c3)nc2-c2ccc3c(cnn3S(C)(=O)=O)c2)n1]

Step A: 2-(6-methylpyridin-2-yl)-3-(1-(methylsulfonyl)-1H-indazol-5-yl)imidazo[1,2-a]pyrimidine A mixture of 2-(6-methylpyridin-2-yl)imidazo[1,2-a]pyrimidine (Intermediate 16, 416 mg, 1.98 mmol), 5-bromo-1-(methylsulfonyl)-1H-indazole (Intermediate 9, 545 mg, 1.98 mmol), Pd(OAc)₂ (36.0 mg, 0.158 mmol), PPh₃ (83.0 mg, 0.317 mmol) and Cs₂CO₃ (710 mg, 2.18 mmol) in dioxane (10.0 mL) was degassed by purging and re-filled with Ar in several times. The reaction mixture was refluxed for 4 hours and cooled to room temperature. After dilution with DCM, the mixture was filtered through a Celite pad. The filtrate was partitioned between DCM and water. The separated aqueous layer was extracted with DCM. The combined organic layers were washed with brine, dried over Na₂SO₄, filtered, and concentrated in vacuo. The residual solid was purified by recrystallization from DCM and diethyl ether to afford 2-(6-methylpyridin-2-yl)-3-(1-(methylsulfonyl)-1H-indazol-5-yl)imidazo[1,2-a]pyrimidine (800 mg) as a pale brown solid, which was be used for the next reaction without further purification. MS: 405.1 [M+H]⁺.

Step B: 5-(6-methylpyridin-2-yl)-4-(1-(methylsulfonyl)-1H-indazol-5-yl)-1H-imidazol-2-amine 5-(6-Methylpyridin-2-yl)-4-(1-(methylsulfonyl)-1H-indazol-5-yl)-1H-imidazol-2-amine (310 mg, 42% for two steps) as a yellow solid was synthesized from 2-(6-methylpyridin-2-yl)-3-(1-(methylsulfonyl)-1H-indazol-5-yl)imidazo-[1,2-a]pyrimidine (800 mg, 1.97 mmol) by following the procedure for Example 13 (Step B). ¹H-NMR (400 MHz, DMSO-d₆): δ 11.06-10.66 (1H, brs+brs), 8.60 (1H, s), 8.14 (1H, s), 7.90-7.85 (2H, m), 7.51-7.47 (1H, m), 7.26-7.10 (1H, m), 6.97-6.92 (1H, m), 5.51 (2H, brs), 3.48 (3H, s), 2.46-2.18 (3H, brs+brs). MS: 369.1 [M+H]⁺.

Step C: N-(3-fluorobenzyl)-5-(6-methylpyridin-2-yl)-4-(1-(methylsulfonyl)-1H-indazol-5-yl)-1H-imidazol-2-amine N-(3-Fluorobenzyl)-5-(6-methylpyridin-2-yl)-4-(1-(methylsulfonyl)-1H-indazol-5-yl)-1H-imidazol-2-amine (57.0 mg, 30% for two steps) as a yellow solid was synthesized from 5-(6-methylpyridin-2-yl)-4-(1-(methylsulfonyl)-1H-indazol-5-yl)-1H-imidazol-2-amine (150 mg, 0.407 mmol) and 3-fluoro-benzaldehyde (0.130 mL, 1.22 mmol) by following the procedure for Example 13 (Step C). ¹H-NMR (400 MHz, DMSO-d₆): δ 11.19-10.80 (1H, brs+brs), 8.63-8.59 (1H, brs+brs), 8.30-8.14 (1H, brs+brs), 7.99-7.12 (1H, d+d), 7.91-7.47 (3H, m), 7.40-7.35 (1H, m), 7.28-7.20 (2H, m), 7.08-7.03 (1H, m), 6.99-6.97 (1H, m), 6.44-6.31 (1H, t+t), 4.52-4.48 (2H, m), 3.46 (3H, s), 2.47-2.30 (3H, brs+brs). MS: 477.1 [M+H]⁺.

Example 23: N-(3-chloro-2-fluorobenzyl)-4-(1-methyl-1H-indazol-5-yl)-5-(6-methylpyridin-2-yl)-1H-imidazol-2-amine

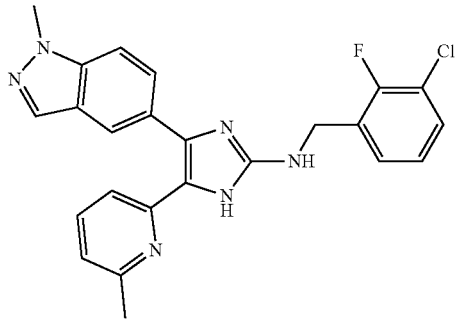 [SMILES: Cc1cccc(-c2[nH]c(NCc3cccc(Cl)c3F)nc2-c2ccc3c(cnn3C)c2)n1]

N-(3-Chloro-2-fluorobenzyl)-4-(1-methyl-1H-indazol-5-yl)-5-(6-methylpyridin-2-yl)-1H-imidazol-2-amine (133 mg, 61% for two steps) as a yellow solid was synthesized from 4-(1-methyl-1H-indazol-5-yl)-5-(6-methylpyridin-2-yl)-1H-imidazol-2-amine (150 mg 0.493 mmol) and 3-chloro-2-fluoro-benzaldehyde (0.170 mL, 1.46 mmol) by following the procedure for Example 13 (Step C). $^1$H-NMR (400 MHz, DMSO-$d_6$): δ 11.11-10.67 (1H, brs+brs), 8.06-8.02 (1H, brs+brs), 8.03-7.89 (1H, brs+brs), 7.73-7.03 (1H, d+d), 7.60-7.38 (5H, m), 7.23-7.19 (1H, m), 6.95-6.92 (1H, d+d), 6.34-6.25 (1H, t+t), 4.58-4.54 (2H, m), 4.04-4.03 (3H, m), 2.46-2.29 (3H, brs+brs). MS: 447.1 [M+H]$^+$.

Example 24: N-(3,4-dichlorobenzyl)-4-(1-methyl-1H-indazol-5-yl)-5-(6-methylpyridin-2-yl)-1H-imidazol-2-amine

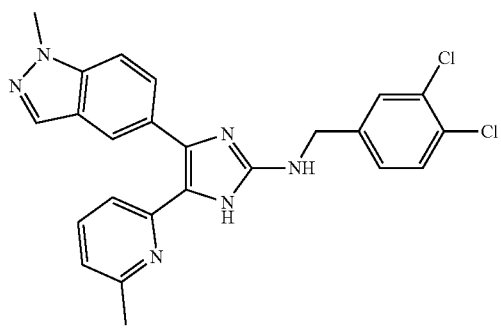 [SMILES: Cc1cccc(-c2[nH]c(NCc3ccc(Cl)c(Cl)c3)nc2-c2ccc3c(cnn3C)c2)n1]

N-(3,4-Dichlorobenzyl)-4-(1-methyl-1H-indazol-5-yl)-5-(6-methylpyridin-2-yl)-1H-imidazol-2-amine (107 mg, 66%) as a yellow solid was synthesized from 4-(1-methyl-1H-indazol-5-yl)-5-(6-methylpyridin-2-yl)-1H-imidazol-2-amine (150 mg 0.493 mmol) and 3,4-dichloro-benzaldehyde (259 mg, 1.48 mmol) by following the procedure for Example 13 (Step C). $^1$H-NMR (400 MHz, DMSO-$d_6$): δ 11.11-10.68 (1H, brs+brs), 8.06-8.02 (1H, brs+brs), 8.03-7.89 (1H, brs+brs), 7.73-7.03 (1H, d+d), 7.70-7.38 (6H, m), 6.95-6.92 (1H, d+d), 6.39-6.30 (1H, t+t), 4.48-4.44 (2H, d+d), 4.04-4.03 (3H, m), 2.46-2.29 (3H, brs+brs). MS: 463.0 [M+H]$^+$.

Example 25: 4-(1-(difluoromethyl)-1H-indazol-5-yl)-N-(3-fluorobenzyl)-5-(6-methyl-pyridin-2-yl)-1H-imidazol-2-amine

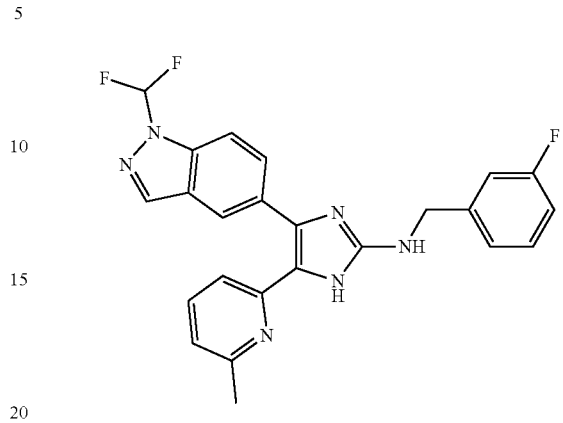

Step A: 3-(1-(difluoromethyl)-1H-indazol-5-yl)-2-(6-methylpyridin-2-yl)-imidazo[1,2-a]pyrimidine A mixture of 2-(6-methylpyridin-2-yl)imidazo[1,2-a]pyrimidine (Intermediate 16, 422 mg, 2.00 mmol), 5-bromo-1-(difluoromethyl)-1H-indazole (Intermediate 8, 496 mg, 2.00 mmol), Pd(OAc)$_2$ (36.0 mg, 0.158 mmol), PPh$_3$ (83.0 mg, 0.317 mmol), and Cs$_2$CO$_3$ (710 mg, 2.18 mmol) in dioxane (10 mL) was degassed by purging and re-filled with Ar in several times. The reaction mixture was refluxed for 4 hours and cooled to room temperature. After dilution with DCM, the mixture was filtered through a Celite pad. The filtrate was partitioned between DCM and water. The separated aqueous layer was extracted with DCM. The combined organic layers were washed with brine, dried over Na$_2$SO$_4$, filtered, and concentrated in vacuo. The residual solid was purified by recrystallization from DCM and diethyl ether to afford 3-(1-(difluoromethyl)-1H-indazol-5-yl)-2-(6-methylpyridin-2-yl)imidazo[1,2-a]pyrimidine (756 mg) as a pale brown solid. MS: 377.1 [M+H]$^+$

Step B: 4-(1-(difluoromethyl)-1H-indazol-5-yl)-5-(6-methylpyridin-2-yl)-1H-imidazol-2-amine 4-(1-(Difluoromethyl)-1H-indazol-5-yl)-5-(6-methylpyridin-2-yl)-1H-imidazol-2-amine (1.06 g, 51% for two steps) as a yellow solid was synthesized from 3-(1-(difluoromethyl)-1H-indazol-5-yl)-2-(6-methylpyridin-2-yl)imidazo[1,2-a]pyrimidine (756 mg, 2.00 mmol) by following the procedure for Example 13 (Step B). $^1$H-NMR (400 MHz, DMSO-$d_6$): δ 11.02-10.60 (1H, brs+brs), 8.83 (1H, s), 8.27-7.96 (2H, m), 7.67-7.65 (1H, m), 7.56-7.54 (1H, m), 7.47-7.41 (1H, m), 7.12-7.10 (1H, m), 6.94-6.92 (1H, m), 5.48-5.46 (2H, m), 3.48 (3H, s), 2.46-2.31 (3H, brs+brs). MS: 341.1 [M+H]$^+$

Step C: 4-(1-(difluoromethyl)-1H-indazol-5-yl)-N-(3-fluorobenzyl)-5-(6-methylpyridin-2-yl)-1H-imidazol-2-amine 4-(1-(Difluoromethyl)-1H-indazol-5-yl)-N-(3-fluorobenzyl)-5-(6-methylpyridin-2-yl)-1H-imidazol-2-amine (111 mg, 56.1% for two steps) as a yellow solid was synthesized from 4-(1-(difluoromethyl)-1H-indazol-5-yl)-5-(6-methylpyridin-2-yl)-1H-imidazol-2-amine (150 mg, 0.441 mmol) and 3-fluoro-benzaldehyde (0.140 mL, 1.32 mmol) by following the procedure for Example 13 (Step C). $^1$H-NMR (400 MHz, DMSO-d$_6$): δ 11.14-10.73 (1H, brs+brs), 8.88-8.83 (1H, brs+brs), 8.27-7.97 (2H, m), 7.66-7.64 (1H, m), 7.59-7.47 (1H, t+t), 7.58-7.12 (1H, d+d), 7.55-7.52 (1H, m), 7.40-7.35 (1H, m), 7.27-7.20 (2H, m), 7.08-7.03 (1H, m), 6.98-6.95 (1H, m), 6.42-6.28 (1H, t+t), 4.51-4.48 (2H, d+d), 2.47-2.30 (3H, brs+brs). MS: 449.1 [M+H]$^+$.

Example 26: 2-(5-(2-((3-fluorobenzyl)amino)-5-(6-methylpyridin-2-yl)-1H-imidazol-4-yl)-1H-indazol-1-yl)-2-methylpropan-1-ol

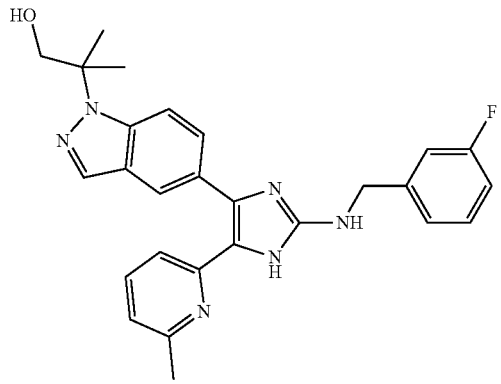 [SMILES: Cc1cccc(-c2[nH]c(NCc3cccc(F)c3)nc2-c2ccc3c(cnn3C(C)(C)CO)c2)n1]

Step A: 2-methyl-2-(5-(2-(6-methylpyridin-2-yl)imidazo[1,2-a]pyrimidin-3-yl)-1H-indazol-1-yl)propan-1-ol A mixture of 2-(6-methylpyridin-2-yl)imidazo[1,2-a]pyrimidine (Intermediate 16, 352 mg, 1.67 mmol), 2-(5-bromo-1H-indazol-1-yl)-2-methylpropan-1-ol (Intermediate 10, 450 mg, 1.67 mmol), Pd(OAc)$_2$ (30.0 mg, 0.134 mmol), PPh$_3$ (70.0 mg, 0.268 mmol) and Cs$_2$CO$_3$ (600 mg, 1.84 mmol) in dioxane (8.30 mL) was degassed by purging and re-filled with Ar in several times. The reaction mixture was refluxed for 4 hours and cooled to room temperature. After dilution with DCM, the mixture was filtered through a Celite pad. The filtrate was partitioned between DCM and water. The separated aqueous layer was extracted with DCM. The combined organic layers were washed with brine, dried over Na$_2$SO$_4$, filtered, and concentrated in vacuo. The residual solid was purified by recrystallization from DCM and diethyl ether to afford 2-methyl-2-(5-(2-(6-methylpyridin-2-yl)imidazo[1,2-a]pyrimidin-3-yl)-1H-indazol-1-yl)propan-1-ol (666 mg) as a pale brown solid. MS: 399.1 [M+H]$^+$ Step B: 2-(5-(2-amino-5-(6-methylpyridin-2-yl)-1H-imidazol-4-yl)-1H-indazol-1-yl)-2-methylpropan-1-ol 4-(1-(Difluoromethyl)-1H-indazol-5-yl)-5-(6-methylpyridin-2-yl)-1H-imidazol-2-amine) (347 mg, 57% for two steps) as a yellow solid was synthesized from 2-methyl-2-(5-(2-(6-methylpyridin-2-yl)imidazo[1,2-a]pyrimidin-3-yl)-1H-indazol-1-yl)propan-1-ol (666 mg, 1.67 mmol) by following the procedure for Example 13 (Step B). $^1$H-NMR (400 MHz, DMSO-d$_6$): δ 10.51 (1H, brs), 8.01 (1H, s), 7.92 (1H, s), 7.58 (2H, s), 7.41 (1H, s), 7.07 (1H, brs), 6.90 (1H, d, J=7.6 Hz), 5.42 (2H, brs), 4.04 (3H, s), 2.43 (3H, s). MS: 363.1 [M+H]$^+$.

Step C: 2-(5-(2-((3-fluorobenzyl)amino)-5-(6-methylpyridin-2-yl)-1H-imidazol-4-yl)-1H-indazol-1-yl)-2-methylpropan-1-ol 2-(5-(2-((3-Fluorobenzyl)amino)-5-(6-methylpyridin-2-yl)-1H-imidazol-4-yl)-1H-indazol-1-yl)-2-methylpropan-1-ol (107 mg, 55% for two steps) as a yellow solid was synthesized from 2-(5-(2-amino-5-(6-methylpyridin-2-yl)-1H-imidazol-4-yl)-1H-indazol-1-yl)-2-methylpropan-1-ol (150 mg, 0.414 mmol) and 3-fluoro-benzaldehyde (0.140 mL, 1.32 mmol) by following the procedure for Example 13 (Step C). $^1$H-NMR (400 MHz, DMSO-d$_6$): δ 11.04-10.61 (1H, brs+brs), 8.08-8.03 (1H, brs+brs), 8.05-7.89 (1H, brs+brs), 7.71-7.64 (1H, m), 7.61-7.04 (1H, d+d), 7.58-7.34 (3H, m), 7.28-7.20 (2H, m), 7.10-7.08 (1H, m), 6.95-6.91 (1H, m), 6.32-6.24 (1H, t+t), 4.69 (1H, s), 4.51-4.47 (2H, m), 4.30 (2H, s), 2.48-2.29 (3H, brs+brs), 1.13 (6H, s). MS: 471.1 [M+H]$^+$.

Example 27: N-(3-chloro-2-fluorobenzyl)-4-(1-(difluoromethyl)-1H-indazol-5-yl)-5-(6-ethyl-pyridin-2-yl)-1H-imidazol-2-amine

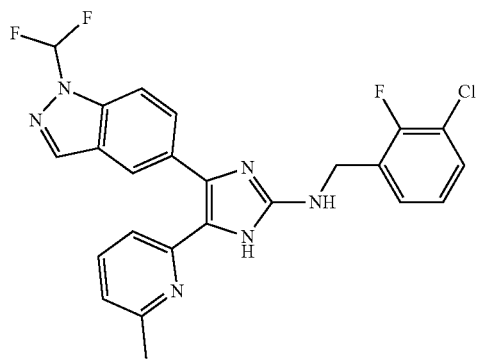

N-(3-Chloro-2-fluorobenzyl)-4-(1-(difluoromethyl)-1H-indazol-5-yl)-5-(6-methylpyridin-2-yl)-1H-imidazol-2-amine (90.0 mg, 64% for two steps) as a yellow solid was synthesized from 4-(1-(difluoromethyl)-1H-indazol-5-yl)-5-(6-methylpyridin-2-yl)-1H-imidazol-2-amine (100 mg, 0.294 mmol) and 3-chloro-2-fluoro-benzaldehyde (0.100 mL, 0.858 mmol) by following the procedure for Example 25 (Step C). $^1$H-NMR (400 MHz, DMSO-d$_6$): δ 11.24-10.80 (1H, brs+brs), 8.87-8.83 (1H, brs+brs), 8.27-7.97 (2H, m), 7.66-7.63 (1H, m), 7.59-7.11 (1H, d+d), 7.58-7.43 (4H, m), 7.23-7.19 (1H, m), 6.98-6.95 (1H, m), 6.48-6.32 (1H, t+t), 4.58-4.54 (2H, m), 2.46-2.29 (3H, brs+brs). MS: 483.1 [M+H]$^+$.

Example 28: N-(3,4-dichlorobenzyl)-4-(1-(difluoromethyl)-1H-indazol-5-yl)-5-(6-methyl-pyridin-2-yl)-1H-imidazol-2-amine

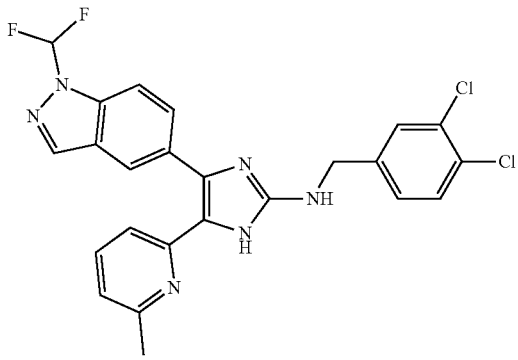 [SMILES: Cc1cccc(-c2[nH]c(NCc3ccc(Cl)c(Cl)c3)nc2-c2ccc3c(cnn3C(F)F)c2)n1]

N-(3,4-Dichlorobenzyl)-4-(1-(difluoromethyl)-1H-indazol-5-yl)-5-(6-methylpyridin-2-yl)-1H-imidazol-2-amine (93.0 mg, 63% for two steps) as a yellow solid was synthesized from 4-(1-(difluoromethyl)-1H-indazol-5-yl)-5-(6-methylpyridin-2-yl)-1H-imidazol-2-amine (100 mg, 0.294 mmol) and 3,4-dichloro-benzaldehyde (154 mg, 0.881 mmol) by following the procedure for Example 25 (Step C). $^1$H-NMR (400 MHz, DMSO-$d_6$): δ 11.21-10.80 (1H, brs+brs), 8.88-8.83 (1H, brs+brs), 8.27-7.96 (2H, m), 7.69-7.59 (3H, m), 7.59-7.47 (1H, t+t), 7.57-7.11 (1H, d+d), 7.54-7.51 (1H, m), 7.43-7.38 (1H, m), 6.98-6.95 (1H, m), 6.51-6.35 (1H, t+t), 4.48-4.45 (2H, d+d), 2.47-2.29 (3H, brs+brs). MS: 499 [M+H]$^+$.

Example 29: N-(3,4-difluorobenzyl)-4-(1-(difluoromethyl)-1H-indazol-5-yl)-5-(6-methyl-pyridin-2-yl)-1H-imidazol-2-amine

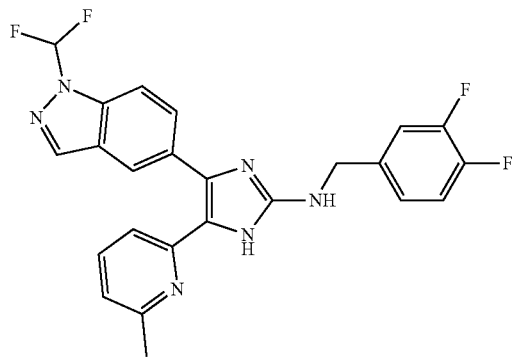 [SMILES: Cc1cccc(-c2[nH]c(NCc3ccc(F)c(F)c3)nc2-c2ccc3c(cnn3C(F)F)c2)n1]

N-(3,4-Difluorobenzyl)-4-(1-(difluoromethyl)-1H-indazol-5-yl)-5-(6-methylpyridin-2-yl)-1H-imidazol-2-amine (65.0 mg, 48% for two steps) as a yellow solid was synthesized from 4-(1-(difluoromethyl)-1H-indazol-5-yl)-5-(6-methylpyridin-2-yl)-1H-imidazol-2-amine (100 mg, 0.294 mmol) and 3,4-difluoro-benzaldehyde (0.100 mL, 0.906 mmol) by following the procedure for Example 25 (Step C). $^1$H-NMR (400 MHz, DMSO-$d_6$): δ 11.19-10.77 (1H, brs+brs), 8.88-8.83 (1H, brs+brs), 8.27-7.97 (2H, m), 7.66-7.64 (1H, m), 7.58-7.11 (1H, d+d), 7.57-7.36 (4H, m), 7.28-7.23 (1H, m), 6.98-6.95 (1H, m), 6.45-6.30 (1H, t+t), 4.47-4.44 (2H, d+d), 2.46-2.29 (3H, brs+brs). MS: 467.1 [M+H]$^+$.

Example 30: 3-(((4-(1-methyl-1H-indazol-5-yl)-5-(6-methylpyridin-2-yl)-1H-imidazol-2-yl)-amino)methyl)benzonitrile

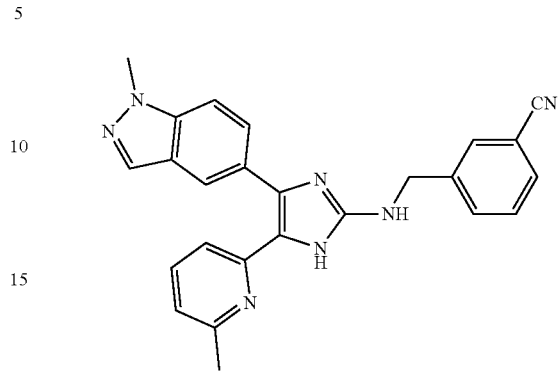

3-(((4-(1-Methyl-1H-indazol-5-yl)-5-(6-methylpyridin-2-yl)-1H-imidazol-2-yl)amino)methyl)-benzonitrile (147 mg, 71% for two steps) as a yellow solid was synthesized from 4-(1-methyl-1H-indazol-5-yl)-5-(6-methylpyridin-2-yl)-1H-imidazol-2-amine (150 mg 0.493 mmol) and 3-cyano-benzaldehyde (194 mg, 1.479 mmol) by following the procedure for Example 13 (Step C). $^1$H-NMR (400 MHz, DMSO-$d_6$): δ 11.14-10.70 (1H, brs+brs), 8.05-8.01 (1H, brs+brs), 8.03-7.89 (1H, brs+brs), 7.87-7.84 (1H, brs+brs), 7.78-7.03 (1H, d+d), 7.76-7.70 (2H, m), 7.60-7.39 (4H, m), 6.95-6.92 (1H, d+d), 6.43-6.32 (1H, t+t), 4.54-4.50 (2H, d+d), 4.04-4.03 (3H, m), 2.46-2.29 (3H, brs+brs). MS: 420.1 [M+H]$^+$.

Example 31: N-(3-fluorobenzyl)-4-(1-methyl-1H-pyrazolo[3,4-b]pyridin-5-yl)-5-(6-methyl-pyridin-2-yl)-1H-imidazol-2-amine

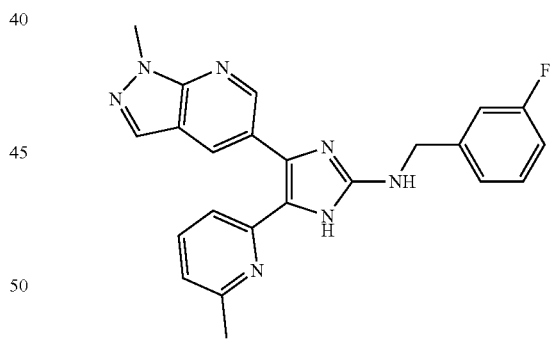

Step A: 1-methyl-5-(2-(6-methylpyridin-2-yl)-imidazo[1,2-a]pyrimidin-3-yl)-1H-pyrazolo[3,4-b]pyridine A mixture of 2-(6-methylpyridin-2-yl)imidazo[1,2-a]pyrimidine (Intermediate 16, 446 mg, 2.12 mmol), 5-bromo-1-methyl-1H-pyrazolo[3,4-b]pyridine (Intermediate 11, 450 mg, 2.12 mmol), Pd(OAc)$_2$ (38.0 mg, 0.170 mmol), PPh$_3$ (89.0 mg, 0.340 mmol) and Cs$_2$CO$_3$ (761 mg, 2.33 mmol) in dioxane (7.5 mL) was degassed by purging and re-filled with Ar in several times. The reaction mixture was refluxed for 4 hours and cooled to room temperature. After dilution with DCM, the mixture was filtered through a Celite pad. The filtrate was partitioned between DCM and water. The separated aqueous layer was extracted with DCM. The combined organic layers were washed with brine, dried over $Na_2SO_4$, filtered, and concentrated in vacuo. The residual solid was purified by recrystallization from DCM and diethyl ether to afford 1-methyl-5-(2-(6-methylpyridin-2-yl)-imidazo[1,2-a]pyrimidin-3-yl)-1H-pyrazolo[3,4-b]pyridine (724 mg) as a pale brown solid. MS: 342.0 [M+H]$^+$ Step B: 4-(1-methyl-1H-pyrazolo[3,4-b]pyridin-5-yl)-5-(6-methylpyridin-2-yl)-1H-imidazol-2-amine 4-(1-Methyl-1H-pyrazolo[3,4-b]pyridin-5-yl)-5-(6-methylpyridin-2-yl)-1H-imidazol-2-amine (500 mg, 77% for two steps) as a yellow solid was synthesized from 1-methyl-5-(2-(6-methylpyridin-2-yl)imidazo[1,2-a]pyrimidin-3-yl)-1H-pyrazolo[3,4-b]pyridine (724 mg, 2.12 mmol) by following the procedure for Example 13 (Step B). $^1$H-NMR (400 MHz, DMSO-$d_6$): δ 8.65 (1H, s), 8.32 (1H, s), 8.08 (1H, s), 7.50-7.27 (3H, m), 7.12-6.99 (2H, m) 4.12 (3H, s), 2.46 (3H, s). MS: 306.0 [M+H]$^+$ Step C: N-(3-fluorobenzyl)-4-(1-methyl-1H-pyrazolo[3,4-b]pyridin-5-yl)-5-(6-methylpyridin-2-yl)-1H-imidazol-2-amine N-(3-Fluorobenzyl)-4-(1-methyl-1H-pyrazolo[3,4-b]pyridin-5-yl)-5-(6-methylpyridin-2-yl)-1H-imidazol-2-amine (65 mg, 41% for two steps) as a yellow solid was synthesized from 4-(1-methyl-1H-pyrazolo[3,4-b]pyridin-5-yl)-5-(6-methylpyridin-2-yl)-1H-imidazol-2-amine (120 mg, 0.393 mmol) and 3-fluoro-benzaldehyde (0.130 mL, 1.22 mmol) by following the procedure for Example 13 (Step C). $^1$H-NMR (400 MHz, DMSO-$d_6$): δ 11.29-10.92 (1H, brs+brs), 8.83-8.72 (1H, d+d), 8.46-8.40 (1H, d+d), 8.16-8.13 (1H, brs+brs), 7.59-7.04 (1H, d+d), 7.50-7.08 (1H, t+t), 7.40-7.35 (1H, m), 7.28-7.20 (2H, m), 7.08-7.07 (1H, m), 6.98-6.96 (1H, m), 6.58-6.41 (1H, t+t), 4.51-4.47 (2H, d+d), 4.06 (3H, s), 2.44-2.24 (3H, brs+brs). MS: 414 [M+H]$^+$.

Example 32: N-(3-fluorobenzyl)-4-(1-methyl-1H-pyrazolo[4,3-b]pyridin-5-yl)-5-(6-methyl-pyridin-2-yl)-1H-imidazol-2-amine

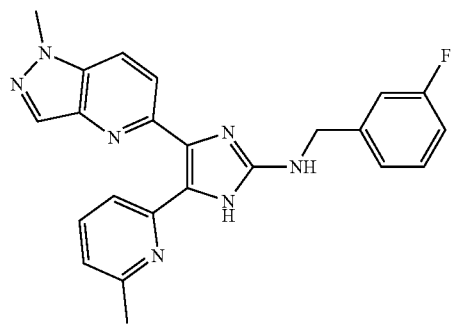 [SMILES: Cc1cccc(-c2[nH]c(NCc3cccc(F)c3)nc2-c2ccc3c(cnn3C)n2)n1]

Step A: 1-methyl-5-(2-(6-methylpyridin-2-yl)imidazo[1,2-a]pyrimidin-3-yl)-1H-pyrazolo[4,3-b]pyridine A mixture of 2-(6-methylpyridin-2-yl)imidazo[1,2-a]pyrimidine (Intermediate 16, 317 mg, 1.50 mmol), 5-bromo-1-methyl-1H-pyrazolo[4,3-b]pyridine (Intermediate 12, 320 mg, 1.50 mmol), Pd(OAc)$_2$ (27.0 mg, 0.121 mmol), PPh$_3$ (63.0 mg, 0.241 mmol) and Cs$_2$CO$_3$ (541 mg, 1.66 mmol) in dioxane (7.0 mL) was degassed by purging and re-filled with Ar in several times. The reaction mixture was refluxed for 4 hours and cooled to room temperature. After dilution with DCM, the mixture was filtered through a Celite pad. The filtrate was partitioned between DCM and water. The separated aqueous layer was extracted with DCM. The combined organic layers were washed with brine, dried over Na$_2$SO$_4$, filtered, and concentrated in vacuo. The residual solid was purified by recrystallization from DCM and diethyl ether to afford 1-methyl-5-(2-(6-methylpyridin-2-yl)imidazo[1,2-a]pyrimidin-3-yl)-1H-pyrazolo[4,3-b]pyridine (515 mg) as a pale brown solid. MS: 342 [M+H]$^+$ Step B: 4-(1-methyl-1H-pyrazolo[4,3-b]pyridin-5-yl)-5-(6-methylpyridin-2-yl)-1H-imidazol-2-amine 4-(1-Methyl-1H-pyrazolo[4,3-b]pyridin-5-yl)-5-(6-methylpyridin-2-yl)-1H-imidazol-2-amine (363 mg, 79% for two steps) as a yellow solid was synthesized from 1-methyl-5-(2-(6-methylpyridin-2-yl)imidazo[1,2-a]pyrimidin-3-yl)-1H-pyrazolo[4,3-b]pyridine (515 mg) by following the procedure for Example 13 (Step B). $^1$H-NMR (400 MHz, DMSO-$d_6$): δ 8.11 (1H, s), 7.96 (1H, brs), 7.74 (1H, d, J=8.1 Hz), 7.61 (1H, brs), 7.50 (1H, d, J=7.6 Hz), 7.12 (1H, brs), 4.10 (3H, s), 2.52 (3H, s). MS: 306 [M+H]$^+$.

Step C: N-(3-fluorobenzyl)-4-(1-methyl-1H-pyrazolo[4,3-b]pyridin-5-yl)-5-(6-methyl-pyridin-2-yl)-1H-imidazol-2-amine N-(3-Fluorobenzyl)-4-(1-methyl-1H-pyrazolo[4,3-b]pyridin-5-yl)-5-(6-methylpyridin-2-yl)-1H-imidazol-2-amine (33.8 mg, 21% for two steps) as a yellow solid was synthesized from 4-(1-methyl-1H-pyrazolo[4,3-b]pyridin-5-yl)-5-(6-methylpyridin-2-yl)-1H-imidazol-2-amine (120 mg, 0.393 mmol) and 3-fluoro-benzaldehyde (0.130 mL, 1.22 mmol) by following the procedure for Example 13 (Step C). $^1$H-NMR (400 MHz, DMSO-$d_6$): δ 11.07-10.76 (1H, brs+brs), 8.76-8.13 (1H, d+d), 8.48-8.04 (1H, d+d), 8.19 (1H, d, J=7.2 Hz), 7.94-7.01 (1H, d+d), 7.69-7.68 (1H, m), 7.57-7.11 (1H, t+t), 7.40-7.35 (1H, m), 7.27-7.21 (2H, m), 7.09-7.04 (1H, m), 6.32-6.26 (1H, t+t), 4.54 (2H, t, J=6.0 Hz), 4.08-4.06 (3H, m), 2.47 (3H, s). MS: 414.1 [M+H]$^+$.

Example 33: N-(3-fluorobenzyl)-4-(1-methyl-1H-pyrazolo[3,4-c]pyridin-5-yl)-5-(6-methyl-pyridin-2-yl)-1H-imidazol-2-amine

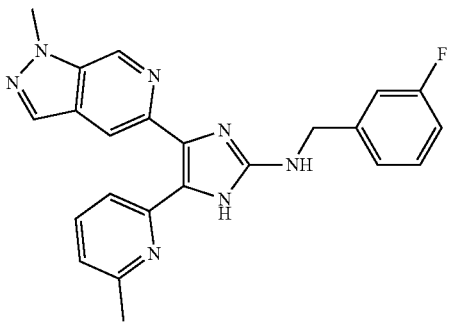

Step A: 1-methyl-5-(2-(6-methylpyridin-2-yl)imidazo[1,2-a]pyrimidin-3-yl)-1H-pyrazolo[3,4-c]pyridine A mixture of 2-(6-methylpyridin-2-yl)imidazo[1,2-a]pyrimidine (Intermediate 16, 317 mg, 1.50 mmol), 5-bromo-1-methyl-1H-pyrazolo[3,4-c]pyridine (Intermediate 13, 320 mg, 1.50 mmol), Pd(OAc)$_2$ (27.0 mg, 0.121 mmol), PPh$_3$ (63.0 mg, 0.241 mmol) and Cs$_2$CO$_3$ (541 mg, 1.66 mmol) in dioxane (7.0 mL) was degassed by purging and re-filled with Ar in several times. The reaction mixture was refluxed for 4 hours and cooled to room temperature. After dilution with DCM, the mixture was filtered through a Celite pad. The filtrate was partitioned between DCM and water. The separated aqueous layer was extracted with DCM. The combined organic layers were washed with brine, dried over Na$_2$SO$_4$, filtered, and concentrated in vacuo. The residual solid was purified by recrystallization from DCM and diethyl ether to afford 1-methyl-5-(2-(6-methylpyridin-2-yl)imidazo[1,2-a]pyrimidin-3-yl)-1H-pyrazolo[3,4-c]pyridine (515 mg) as a pale brown solid. MS: 342 [M+H]$^+$.

Step B: 4-(1-methyl-1H-pyrazolo[3,4-c]pyridin-5-yl)-5-(6-methylpyridin-2-yl)-1H-imidazol-2-amine 4-(1-Methyl-1H-pyrazolo[3,4-c]pyridin-5-yl)-5-(6-methylpyridin-2-yl)-1H-imidazol-2-amine (305 mg, 66% for two steps) as a yellow solid was synthesized from 1-methyl-5-(2-(6-methylpyridin-2-yl)imidazo[1,2-a]pyrimidin-3-yl)-1H-pyrazolo[3,4-c]pyridine (515 mg, crude) by following the procedure for Example 13 (Step B). $^1$H-NMR (400 MHz, DMSO-d$_6$): δ 10.81-10.57 (1H, brs+brs), 9.25-9.13 (1H, brs+brs), 8.27-6.89 (4H, m), 5.50-5.38 (2H, brs+brs), 4.21-4.18 (3H, brs+brs), 2.52-2.41 (3H, brs+brs). MS: 306 [M+H]$^+$.

Step C: N-(3-fluorobenzyl)-4-(1-methyl-1H-pyrazolo[3,4-c]pyridin-5-yl)-5-(6-methyl-pyridin-2-yl)-1H-imidazol-2-amine N-(3-Fluorobenzyl)-4-(1-methyl-1H-pyrazolo[3,4-c]pyridin-5-yl)-5-(6-methylpyridin-2-yl)-1H-imidazol-2-amine (38 mg, 23% for two steps) as a brown solid was synthesized from 4-(1-methyl-1H-pyrazolo[3,4-c]pyridin-5-yl)-5-(6-methylpyridin-2-yl)-1H-imidazol-2-amine (120 mg, 0.393 mmol) and 3-fluoro-benzaldehyde (0.130 mL, 1.22 mmol) by following the procedure for Example 13 (Step C). $^1$H-NMR (400 MHz, DMSO-d$_6$): δ 10.98-10.62 (1H, brs+brs), 9.52-9.13 (1H, brs+brs), 8.19-8.11 (2H, m), 7.73-6.97 (7H, m), 6.28-6.17 (1H, t+t), 4.54 (2H, t, J=7.6 Hz), 4.18 (3H, s), 2.53 (3H, s). MS: 414.1 [M+H]$^+$.

Example 34: N-(2-fluorobenzyl)-4-(1-methyl-1H-indazol-5-yl)-5-(6-methylpyridin-2-yl)-1H-imidazol-2-amine

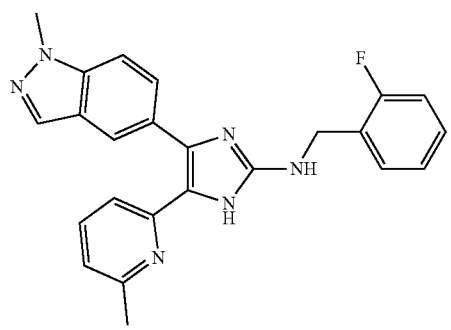 [SMILES: Cc1cccc(-c2[nH]c(NCc3ccccc3F)nc2-c2ccc3c(cnn3C)c2)n1]

N-(2-Fluorobenzyl)-4-(1-methyl-1H-indazol-5-yl)-5-(6-methylpyridin-2-yl)-1H-imidazol-2-amine (98.0 mg, 48% for two steps) as a yellow solid was synthesized from 4-(1-methyl-1H-indazol-5-yl)-5-(6-methylpyridin-2-yl)-1H-imidazol-2-amine (150 mg, 0.493 mmol) and 2-fluoro-benzaldehyde (0.160 mL, 1.52 mmol) by following the procedure for Example 13 (Step C). $^1$H-NMR (400 MHz, DMSO-d$_6$): δ 11.03-10.59 (1H, brs+brs), 8.07-8.02 (1H, brs+brs), 8.03-7.90 (1H, brs+brs), 7.74-7.03 (1H, d+d), 7.60-7.38 (4H, m), 7.33-7.27 (1H, m), 7.20-7.16 (2H, m), 6.94-6.92 (1H, d+d), 6.16-6.13 (1H, t+t), 4.55-4.51 (2H, m), 4.04-4.03 (3H, m), 2.46-2.30 (3H, brs+brs). MS: 413.1 [M+H]$^+$.

Example 35: N-(2,3-difluorobenzyl)-4-(1-methyl-1H-indazol-5-yl)-5-(6-methylpyridin-2-yl)-1H-imidazol-2-amine

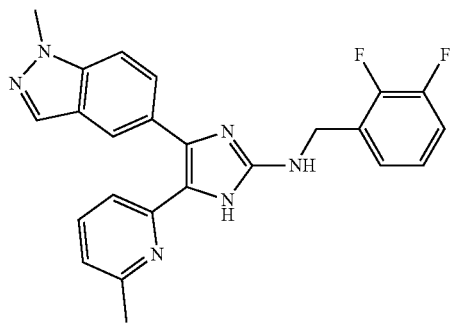 [SMILES: Cc1cccc(-c2[nH]c(NCc3cccc(F)c3F)nc2-c2ccc3c(cnn3C)c2)n1]

N-(2,3-Difluorobenzyl)-4-(1-methyl-1H-indazol-5-yl)-5-(6-methylpyridin-2-yl)-1H-imidazol-2-amine (140 mg, 66% for two steps) as a yellow solid was synthesized from 4-(1-methyl-1H-indazol-5-yl)-5-(6-methylpyridin-2-yl)-1H-imidazol-2-amine (150 mg, 0.493 mmol) and 2,3-difluoro-benzaldehyde (0.160 mL, 1.46 mmol) by following the procedure for Example 13 (Step C). $^1$H-NMR (400 MHz, DMSO-d$_6$): δ 11.09-10.65 (1H, brs+brs), 8.07-8.01 (1H, brs+brs), 8.03-7.90 (1H, brs+brs), 8.07-7.93 (3H, m), 7.74-7.03 (1H, d+d), 7.60-7.38 (3H, m), 7.36-7.16 (3H, m), 6.95-6.92 (1H, d+d), 6.29-6.22 (1H, t+t), 4.59-4.55 (2H, m), 4.04-4.03 (3H, m), 2.46-2.29 (3H, brs+brs). MS: 431 [M+H]$^+$.

Example 36: N-(2,4-difluorobenzyl)-4-(1-methyl-1H-indazol-5-yl)-5-(6-methylpyridin-2-yl)-1H-imidazol-2-amine

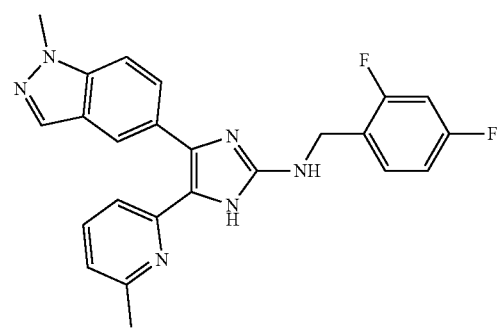

N-(2,4-Difluorobenzyl)-4-(1-methyl-1H-indazol-5-yl)-5-(6-methylpyridin-2-yl)-1H-imidazol-2-amine (141 mg, 67% for two steps) as a yellow solid was synthesized from 4-(1-methyl-1H-indazol-5-yl)-5-(6-methylpyridin-2-yl)-1H-imidazol-2-amine (150 mg, 0.493 mmol) and 2,4-difluoro-benzaldehyde (0.160 mL, 1.46 mmol) by following the procedure for Example 13 (Step C). $^1$H-NMR (400 MHz, DMSO-$d_6$): δ 11.05-10.61 (1H, brs+brs), 8.07-8.02 (1H, brs+brs), 8.03-7.90 (1H, brs+brs), 7.74-7.03 (1H, d+d), 7.60-7.38 (4H, m), 7.25-7.18 (1H, m), 7.09-7.05 (1H, m), 6.95-6.92 (1H, d+d), 6.19-6.14 (1H, t+t), 4.51-4.47 (2H, m), 4.05-4.03 (3H, m), 2.46-2.30 (3H, brs+brs). MS: 431.1 [M+H]$^+$.

Example 37: N-(4-chloro-2-fluorobenzyl)-4-(1-methyl-1H-indazol-5-yl)-5-(6-methylpyridin-2-yl)-1H-imidazol-2-amine

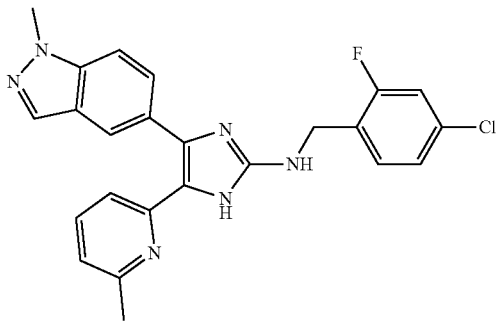 [SMILES: Cc1cccc(-c2[nH]c(NCc3ccc(Cl)cc3F)nc2-c2ccc3c(cnn3C)c2)n1]

N-(4-Chloro-2-fluorobenzyl)-4-(1-methyl-1H-indazol-5-yl)-5-(6-methylpyridin-2-yl)-1H-imidazol-2-amine (129 mg, 73% for two steps) as a yellow solid was synthesized from 4-(1-methyl-1H-indazol-5-yl)-5-(6-methylpyridin-2-yl)-1H-imidazol-2-amine (150 mg, 0.493 mmol) and 4-chloro-2-fluoro-benzaldehyde (0.190 mg, 1.19 mmol) by following the procedure for Example 13 (Step C). $^1$H-NMR (400 MHz, DMSO-$d_6$): δ 11.09-10.65 (1H, brs+brs), 8.07-8.02 (1H, brs+brs), 8.03-7.89 (1H, brs+brs), 8.07-7.93 (3H, m), 7.74-7.03 (1H, d+d), 7.60-7.38 (5H, m), 7.30-7.27 (1H, m), 6.95-6.92 (1H, d+d), 6.25-6.19 (1H, t+t), 4.52-4.48 (2H, m), 4.04-4.03 (3H, m), 2.46-2.29 (3H, brs+brs). MS: 447 [M+H]$^+$.

Example 38: N-(3-fluorobenzyl)-5-(6-methylpyridin-2-yl)-4-(1H-pyrazolo[3,4-b]pyridin-5-yl)-1H-imidazol-2-amine

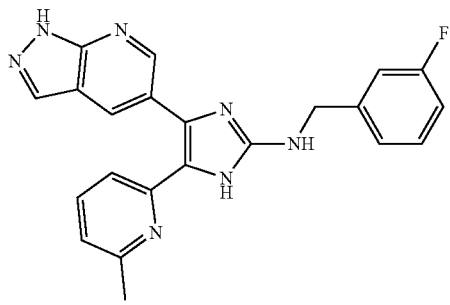 [SMILES: Cc1cccc(-c2[nH]c(NCc3cccc(F)c3)nc2-c2cnc3[nH]ncc3c2)n1]

Step A: 5-(2-(6-methylpyridin-2-yl)imidazo[1,2-a]pyrimidin-3-yl)-1-(tetrahydro-2H-pyran-2-yl)-1H-pyrazolo[3,4-b]pyridine A mixture of 2-(6-methylpyridin-2-yl)imidazo[1,2-a]pyrimidine (Intermediate 16, 531 mg, 2.52 mmol), 5-bromo-1-(tetrahydro-2H-pyran-2-yl)-1H-indazole (Intermediate 14, 712 mg, 2.52 mmol), Pd(OAc)$_2$ (45.0 mg, 0.202 mmol), PPh$_3$ (106 mg, 0.404 mmol) and Cs$_2$CO$_3$ (904 mg, 2.78 mmol) in dioxane (17 mL) was degassed by purging and re-filled with Ar in several times. The reaction mixture was refluxed for 4 hours and cooled to room temperature. After dilution with DCM, the mixture was filtered through a Celite pad. The filtrate was partitioned between DCM and water. The separated aqueous layer was extracted with DCM. The combined organic layers were washed with brine, dried over Na$_2$SO$_4$, filtered, and concentrated in vacuo. The residual solid was purified by recrystallization from DCM and diethyl ether to afford 5-(2-(6-methylpyridin-2-yl)imidazo[1,2-a]pyrimidin-3-yl)-1-(tetrahydro-2H-pyran-2-yl)-1H-pyrazolo[3,4-b]pyridine (1.47 g) as a yellow oil.

Step B: 5-(6-methylpyridin-2-yl)-4-(1-(tetrahydro-2H-pyran-2-yl)-1H-indazol-5-yl)-1H-imidazol-2-amine To a solution of 5-(2-(6-methylpyridin-2-yl)imidazo[1,2-a]pyrimidin-3-yl)-1-(tetrahydro-2H-pyran-2-yl)-1H-pyrazolo[3,4-b]pyridine (1.04 g, 2.52 mmol) in EtOH (13 mL) was added hydrazine hydrate (0.620 mL, 10.2 mmol) at room temperature. The reaction mixture was refluxed for 1 hour and concentration in vacuo. The residue was purified by crystallization from diethyl ether and MeOH to give 4-(6-methylpyridin-2-yl)-5-(1-(tetrahydro-2H-pyran-2-yl)-1H-pyrazolo[3,4-b]pyridin-5-yl)-1H-imidazol-2-amine (60 mg, 6% for three steps) as a yellow oil. $^1$H-NMR (400 MHz, DMSO-$d_6$): δ 11.09-10.76 (1H, s+s), 10.88-10.52 (1H, s+s), 8.85-8.75 (1H, d+d, J=1.6 Hz), 8.54-8.43 (1H, d+d, J=2.0 Hz), 8.22-8.20 (1H, s+s), 7.58-7.54 (3H, m), 7.46 (2H, dt, J=20.0, 8.0 Hz), 7.36-7.24 (3H, m), 7.10 (1H, d, J=8.0 Hz), 7.06 (1H, d, J=7.6 Hz), 6.96 (2H, d, J=8.0 Hz), 6.92 (1H, d, J=7.2 Hz), 6.04 (1H, dd, J=10.2, 2.0 Hz), 5.54 (2H, s), 5.45 (2H, s), 3.96 (1H, d, J=10.8 Hz), 3.74-3.68 (1H, m), 2.46-2.45 (6H, d), 2.33 (1H, s), 2.27 (1H, s), 2.05 (2H, d, J=7.8 Hz), 1.94-1.91 (1H, m), 1.81-1.79 (1H, m), 1.65-1.59 (3H, m).

Step C: N-(3-fluorobenzyl)-5-(6-methylpyridin-2-yl)-4-(1-(tetrahydro-2H-pyran-2-yl)-1H-pyrazolo[3,4-b]pyridin-5-yl)-1H-imidazol-2-amine N-(3-Fluorobenzyl)-5-(6-methylpyridin-2-yl)-4-(1-(tetrahydro-2H-pyran-2-yl)-1H-pyrazolo[3,4-b]pyridin-5-yl)-1H-imidazol-2-amine (65 mg, crude) as a yellow solid was synthesized from 5-(6-methylpyridin-2-yl)-4-(1-(tetrahydro-2H-pyran-2-yl)-1H-pyrazolo[3,4-b]pyridin-5-yl)-1H-imidazol-2-amine (60 mg, 0.160 mmol) and 3-fluorobenzaldehyde (0.050 mL, 0.479 mmol) by following the procedure for Example 1 (Step C).

Step D: N-(3-fluorobenzyl)-5-(6-methylpyridin-2-yl)-4-(1H-pyrazolo[3,4-b]pyridin-5-yl)-1H-imidazol-2-amine N-(3-Fluorobenzyl)-5-(6-methylpyridin-2-yl)-4-(1H-pyrazolo[3,4-b]pyridin-5-yl)-1H-imidazol-2-amine (4.9 mg, 7% for 3 steps) as a yellow solid was synthesized from N-(3-fluorobenzyl)-5-(6-methylpyridin-2-yl)-4-(1-(tetrahydro-2H-pyran-2-yl)-1H-pyrazolo[3,4-b]pyridin-5-yl)-1H-imidazol-2-amine (65.0 mg, 0.134 mmol) by following the procedure for Example 4 (Step D). $^1$H NMR (400 MHz, DMSO-$d_6$): δ 11.16-10.82 (1H, s+s), 8.80-8.68 (1H, d+d, J=2.0 Hz), 8.45-8.38 (1H, d+d, J=2.0 Hz), 8.15-8.12 (1H, s+s), 7.60-7.47 (1H, m), 7.38 (1H, m), 7.29-7.21 (2H, m), 7.08-7.03 (2H, m), 6.97 (1H, d, J=8.0 Hz), 6.40 (1H, t+t, J=6.4 Hz), 4.50 (2H, d+d, J=6.4 Hz), 2.44 (3H, s). MS: 400.1 [M+H]$^+$.

Example 39: N-(3-fluorobenzyl)-4-(1-(methyl-d3)-1H-indazol-5-yl)-5-(6-methylpyridin-2-yl)-1H-imidazol-2-amine

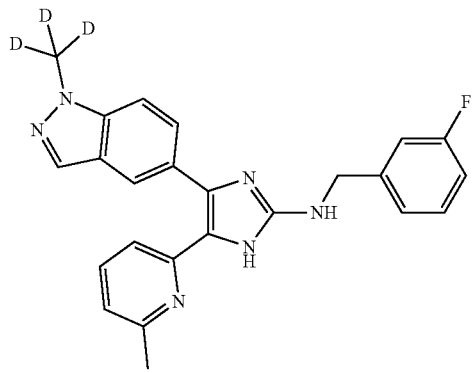 [SMILES: [2H]C([2H])([2H])n1ncc2cc(-c3nc(NCc4cccc(F)c4)[nH]c3-c3cccc(C)n3)ccc21]

Step A: 3-(1-(methyl-da)-1H-indazol-5-yl)-2-(6-methylpyridin-2-yl)imidazo [1,2-a]pyrimidine A mixture of 2-(6-methylpyridin-2-yl)imidazo[1,2-a]pyrimidine (Intermediate 16, 842 mg, 4.00 mmol), 5-bromo-1-methyl-1H-indazole (Intermediate 15, 857 mg, 4.00 mmol), Pd(OAc)$_2$ (72.0 mg, 0.320 mmol), PPh$_3$ (168 mg, 0.641 mmol) and Cs$_2$CO$_3$ (1.43 g, 4.40 mmol) in dioxane (15 mL) was degassed by purging and re-filled with Ar in several times. The reaction mixture was refluxed for 4 hours and cooled to room temperature. After dilution with DCM, the mixture was filtered through a Celite pad. The filtrate was partitioned between DCM and water. The separated aqueous layer was extracted with DCM. The combined organic layers were washed with brine, dried over Na$_2$SO$_4$, filtered, and concentrated in vacuo. The residual solid was purified by recrystallization from DCM and diethyl ether to afford 3-(1-(methyl-d$_3$)-1H-indazol-5-yl)-2-(6-methylpyridin-2-yl)-imidazo[1,2-a]pyrimidine (1.37 g) as a pale brown solid. MS: 344.1 [M+H]$^+$.

Step B: 4-(1-(methyl-d3)-1H-indazol-5-yl)-5-(6-methylpyridin-2-yl)-1H-imidazol-2-amine To a solution of 3-(1-(methyl-d3)-1H-indazol-5-yl)-2-(6-methylpyridin-2-yl) imidazo[1,2-a]-pyrimidine (1.37 g, 6.76 mmol) in EtOH (16 mL) was added hydrazine monohydrate (20 wt %, 1.00 mL, 4.12 mmol) at room temperature. The reaction mixture was refluxed for 2 hours and cooled to room temperature. After filtered through a Celite pad while washing with MeOH, the filtrate was concentrated in vacuo. The residue was purified by crystallization from Et$_2$O and MeOH to give 4-(1-(methyl-d$_3$)-1H-indazol-5-yl)-5-(6-methylpyridin-2-yl)-1H-imidazol-2-amine (538 mg, 43% for two steps) as a yellow solid. $^1$H-NMR (400 MHz, DMSO-$d_6$): δ 10.56 (1H, brs), 8.02 (1H, s), 7.92 (1H, s), 7.59 (2H, s), 7.42 (1H, t, J=7.6 Hz), 7.11 (1H, brs), 6.91 (1H, d, J=7.2 Hz), 5.46 (2H, brs), 2.43 (3H, s). MS: 308.1 [M+H]$^+$.

Step C: N-(3-fluorobenzyl)-4-(1-(methyl-d3)-1H-indazol-5-yl)-5-(6-methylpyridin-2-yl)-1H-imidazol-2-amine N-(3-Fluorobenzyl)-4-(1-(methyl-d3)-1H-indazol-5-yl)-5-(6-methylpyridin-2-yl)-1H-imidazol-2-amine (131 mg, 49% for two steps) as a yellow solid was synthesized from 4-(1-(methyl-d3)-1H-indazol-5-yl)-5-(6-methylpyridin-2-yl)-1H-imidazol-2-amine (200 mg, 0.651 mmol) and 3-fluoro-benzaldehyde (0.210 mL, 1.98 mmol) by following the procedure for Example 13 (Step C). $^1$H-NMR (400 MHz, DMSO-$d_6$): δ 11.05-10.62 (1H, brs+brs), 8.06-8.02 (1H, brs+brs), 8.04-7.89 (1H, brs+brs), 7.73-7.06 (1H, d+d), 7.60-7.35 (4H, m), 7.27-7.20 (2H, m), 7.04-7.02 (1H, m), 6.31-6.23 (1H, t+t), 4.51-4.47 (2H, d+d), 2.46-2.29 (3H, brs+brs). MS: 416.1 [M+H]$^+$.

Biological Activity
Cell Culture

Human cancer cell lines Hs578T (ATCC® HTB-22™) cells were grown in DMEM (Dulbecco's modified Eagle's medium) supplemented with 10% fetal bovine serum and 1% mixture of penicillin and streptomycin (Gibco). Cells were maintained at 37° C. in a humidified 5% CO$_2$_ atmosphere.

ALK5 Kinase Assay

Recombinant ALK5 proteins, ATP and ALK5 substrate (Promega, Madison, USA) at final concentrations of 25 ng, 50 μM and 0.2 ug/ul, respectively, were aliquoted in 50 ul kinase buffer supplemented with 50 uM DTT into 96-well plates, in combination with inhibitor compounds diluted at varying concentrations in kinase buffer in triplicate. Positive control samples lacking inhibitor compounds and negative controls lacking recombinant kinase were also measured in triplicate. The mixture was reacted at RT for 120 min. 50 ul ADP-Glo reagent (Promega) was added and incubate at RT for 40 min. and then 100 ul of kinase detection reagent was added and incubate at RT for 30 min. Kinase activities were measured by Varioskan LUX multimode microplate reader (Thermo Fisher Scientific, Waltham, USA). SigmaPlot (Systat software) was used for graphing and regression analysis by sigmoidal dose-response with variable Hill coefficient.

Cell-Based Luciferase Reporter Assay for ALK5 Activity

Biological activity of the compounds of BSC-1200 was determined by selectively inhibit with Smad 2/3-responsive promoter in response to TGF-β1 stimulation at cellular level. Cells were seeded at 3×10$^4$/well in 24-well plates were transiently transfected with 500 ng of (CAGA)-12-luciferase reporter construct and 5 ng of pRL-TK Renilla luciferase vector (Promega, Madison, WI), an internal control for transfection efficiency, using Lipofectamine 3000 reagent (Thermo Fisher Scientific, Waltham, USA). After 24 h transfection, the cells were pre-treated with ALK5 inhibitor in dose-dependent manner. And then, Cells stimulated with 2 ng/ml recombinant TGF-β1 for 12 hours. After the stimulation, the firefly and Renilla luciferase activities were measured by Dual-Luciferase Reporter Assay (Promega).

Phospho-Smad 2/3 Immunoblotting

Biological activity of the compounds of BSC-1200 was determined by measuring their ability to inhibit TGF-β induced phosphor-Smad 2/3 levels in Hs578T cells. Cells were pretreated with ALK5 inhibitors (10, 20, 50, 100 nM)

for 1 h and treated with human recombinant 2 ng/ml TGF-β1 for 1 h under serum free. Cells were lysed in a buffer containing 25 mM HEPES, pH 7.6, 150 mM NaCl, 1% NP40, 1% sodium deoxycholate, 0.1% SDS, and protease inhibitor mixture (Bimake, Houston, USA). Extracts were separated by SDS-PAGE followed by electro-transfer to polyvinylidene difloride (PVDF) membranes and probed with an anti-phospho-Smad2 Ab, anti-phospho-Smad3 Ab, anti-Smad 2/3 Ab and α-tubulin, followed by horseradish peroxidase-conjugated anti-rabbit, anti-mouse IgG and revealed with Super Signal® West dura kit (Pierce). The membranes are placed in an image analyzer (Imagequant LAS 500; GE Heathcare), connected to a computer which allows the image generation (Software Image Reader LAS 500).

Relative luciferase activity: $IC_{50}$ value (nM)

A: below 10 nM, B: 10-100 nM, C: above 100 nM

| Example | Structure | Assay |
|---|---|---|
| 1 | 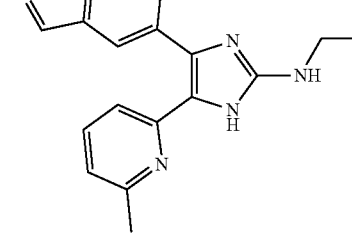 | A |
| 2 | 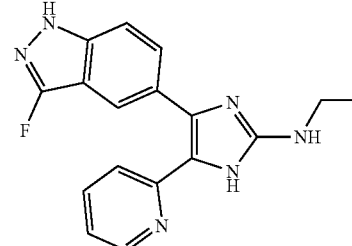 | B |
| 3 | 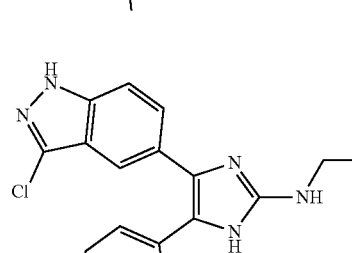 | B |
| 4 | 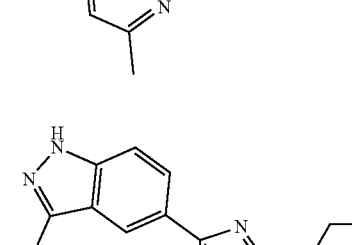 | B |

-continued
| Example | Structure | Assay |
|---|---|---|
| 5 | 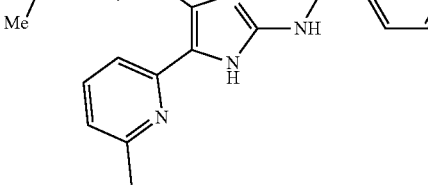 | B |
| 6 | 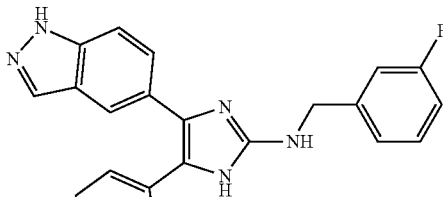 | A |
| 7 | 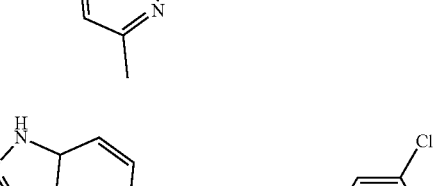 | B |
| 8 | 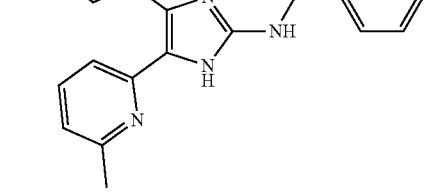 | A |
| 9 | 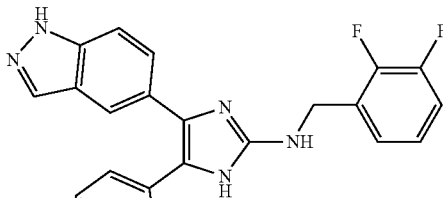 | A |

| Example | Structure | Assay |
|---|---|---|
| 10 | 4-(1H-indazol-5-yl)-N-(4-chloro-2-fluorobenzyl)-5-(6-methylpyridin-2-yl)-1H-imidazol-2-amine | A |
| 11 | 4-(1H-indazol-5-yl)-N-(3-chloro-2-fluorobenzyl)-5-(6-methylpyridin-2-yl)-1H-imidazol-2-amine | A |
| 12 | 4-(1H-indazol-5-yl)-N-(3,4-difluorobenzyl)-5-(6-methylpyridin-2-yl)-1H-imidazol-2-amine | A |
| 13 | N-(3-fluorobenzyl)-4-(1-methyl-1H-indazol-5-yl)-5-(6-methylpyridin-2-yl)-1H-imidazol-2-amine | A |
| 14 | N-(4-fluorobenzyl)-4-(1-methyl-1H-indazol-5-yl)-5-(6-methylpyridin-2-yl)-1H-imidazol-2-amine | A |

-continued
| Example | Structure | Assay |
|---|---|---|
| 15 | 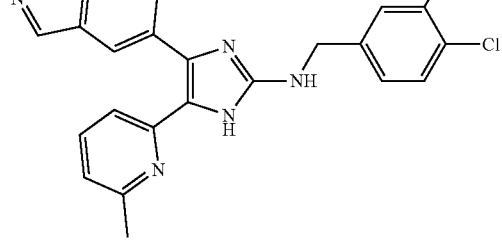 | B |
| 16 | 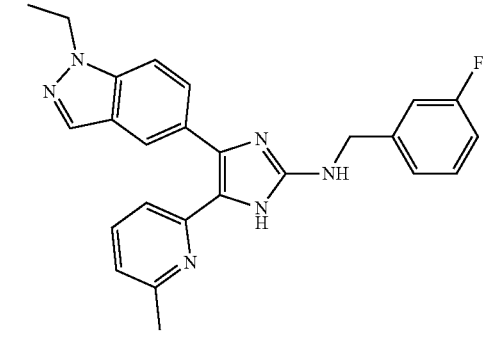 [SMILES: CCn1ncc2cc(-c3nc(NCc4cccc(F)c4)[nH]c3-c3cccc(C)n3)ccc21] | A |
| 17 | 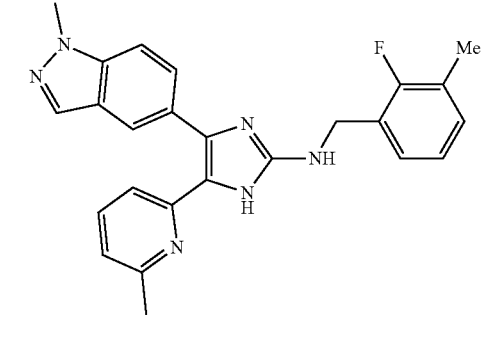 [SMILES: Cc1cccc(-c2[nH]c(NCc3cccc(C)c3F)nc2-c2ccc3c(cnn3C)c2)n1] | B |
| 18 | 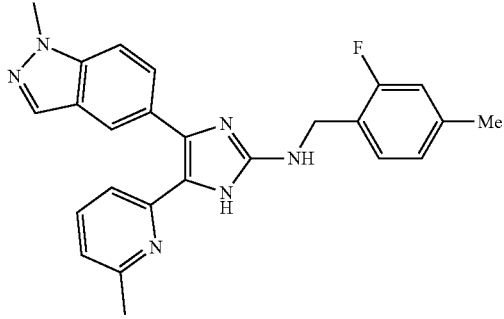 [SMILES: Cc1ccc(CNc2nc(-c3ccc4c(cnn4C)c3)c(-c3cccc(C)n3)[nH]2)c(F)c1] | A |

-continued
| Example | Structure | Assay |
|---|---|---|
| 19 | 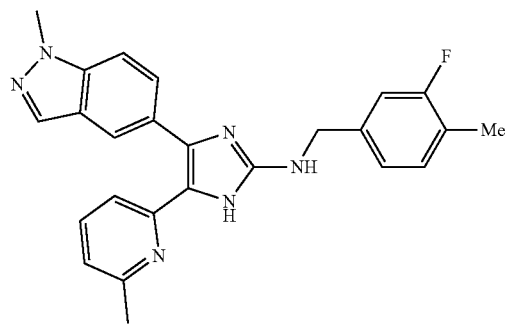 [SMILES: Cc1cccc(-c2[nH]c(NCc3ccc(C)c(F)c3)nc2-c2ccc3c(cnn3C)c2)n1] | A |
| 20 | 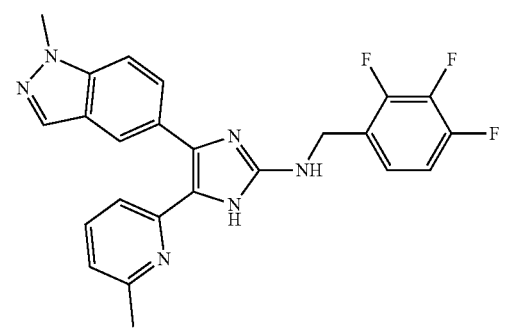 [SMILES: Cc1cccc(-c2[nH]c(NCc3ccc(F)c(F)c3F)nc2-c2ccc3c(cnn3C)c2)n1] | A |
| 21 | 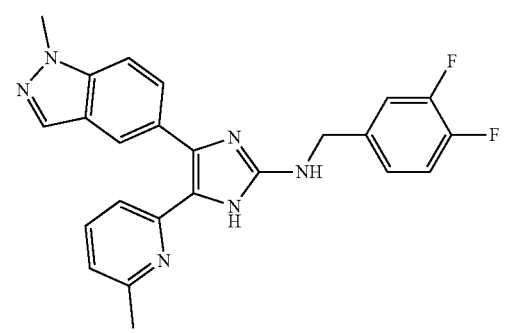 [SMILES: Cc1cccc(-c2[nH]c(NCc3ccc(F)c(F)c3)nc2-c2ccc3c(cnn3C)c2)n1] | A |
| 22 | 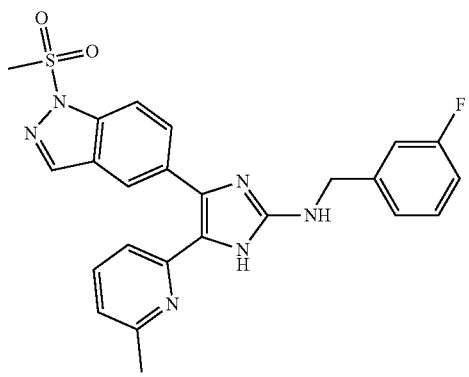 [SMILES: Cc1cccc(-c2[nH]c(NCc3cccc(F)c3)nc2-c2ccc3c(cnn3S(C)(=O)=O)c2)n1] | C |

-continued
| Example | Structure | Assay |
|---------|-----------|-------|
| 23 | 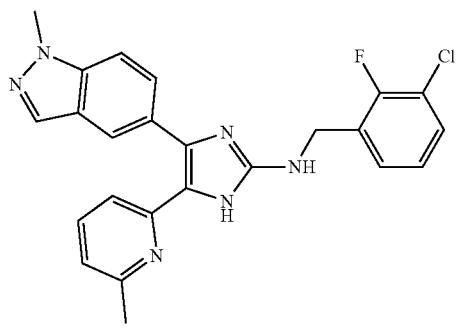 [SMILES: Cc1cccc(-c2[nH]c(NCc3cccc(Cl)c3F)nc2-c2ccc3c(cnn3C)c2)n1] | A |
| 24 | 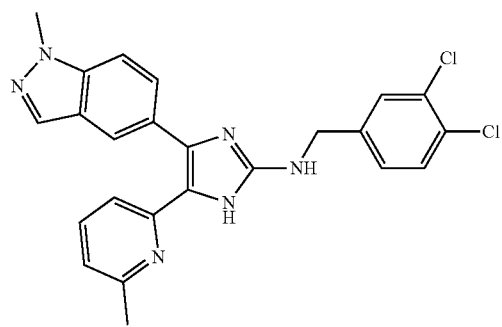 [SMILES: Cc1cccc(-c2[nH]c(NCc3ccc(Cl)c(Cl)c3)nc2-c2ccc3c(cnn3C)c2)n1] | A |
| 25 | 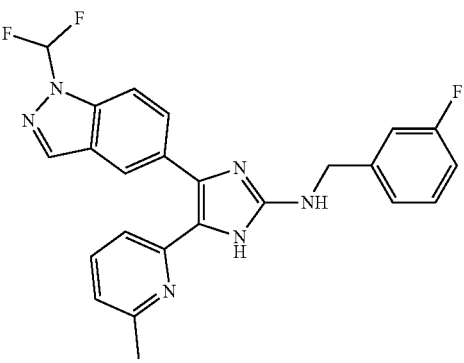 [SMILES: Cc1cccc(-c2[nH]c(NCc3cccc(F)c3)nc2-c2ccc3c(cnn3C(F)F)c2)n1] | A |
| 26 | 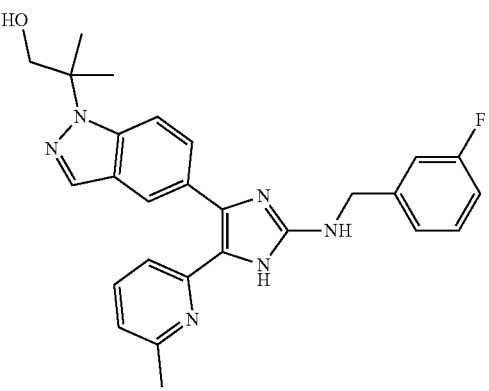 [SMILES: Cc1cccc(-c2[nH]c(NCc3cccc(F)c3)nc2-c2ccc3c(cnn3C(C)(C)CO)c2)n1] | C |

| Example | Structure | Assay |
|---|---|---|
| 27 | 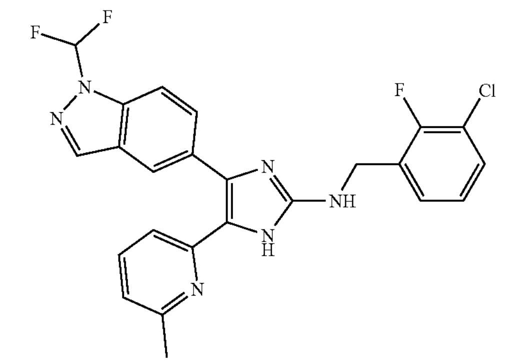 [SMILES: Cc1cccc(-c2[nH]c(NCc3cccc(Cl)c3F)nc2-c2ccc3c(cnn3C(F)F)c2)n1] | B |
| 28 | 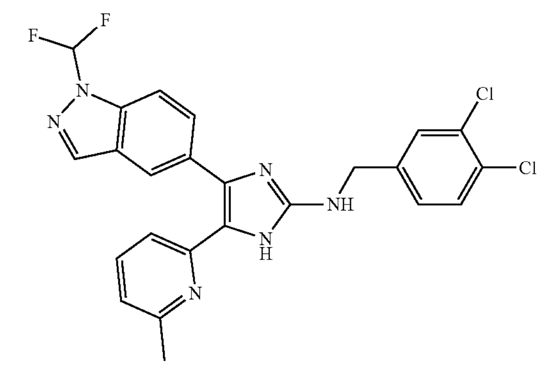 [SMILES: Cc1cccc(-c2[nH]c(NCc3ccc(Cl)c(Cl)c3)nc2-c2ccc3c(cnn3C(F)F)c2)n1] | B |
| 29 | 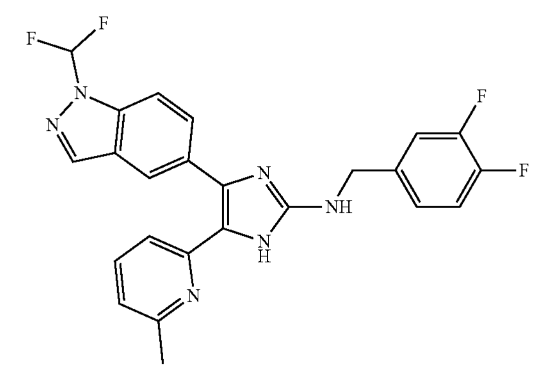 [SMILES: Cc1cccc(-c2[nH]c(NCc3ccc(F)c(F)c3)nc2-c2ccc3c(cnn3C(F)F)c2)n1] | B |
| 30 | 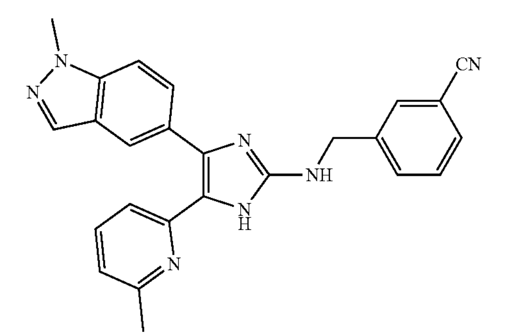 [SMILES: Cc1cccc(-c2[nH]c(NCc3cccc(C#N)c3)nc2-c2ccc3c(cnn3C)c2)n1] | B |

-continued
| Example | Structure | Assay |
|---|---|---|
| 31 | 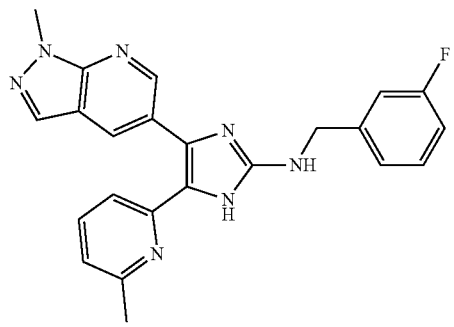 [SMILES: Cc1cccc(-c2[nH]c(NCc3cccc(F)c3)nc2-c2cnc3c(cnn3C)c2)n1] | A |
| 32 | 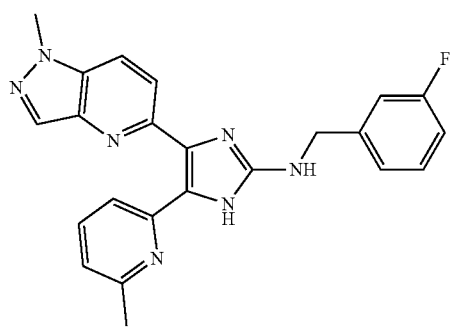 [SMILES: Cc1cccc(-c2[nH]c(NCc3cccc(F)c3)nc2-c2ccc3c(cnn3C)n2)n1] | C |
| 33 | 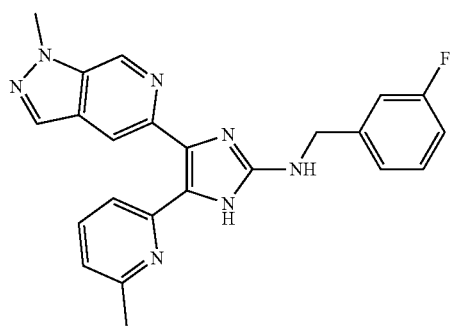 [SMILES: Cc1cccc(-c2[nH]c(NCc3cccc(F)c3)nc2-c2cc3cnn(C)c3cn2)n1] | A |
| 34 | 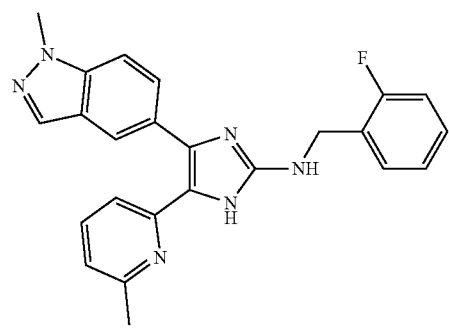 [SMILES: Cc1cccc(-c2[nH]c(NCc3ccccc3F)nc2-c2ccc3c(cnn3C)c2)n1] | A |

| Example | Structure | Assay |
|---|---|---|
| 35 | 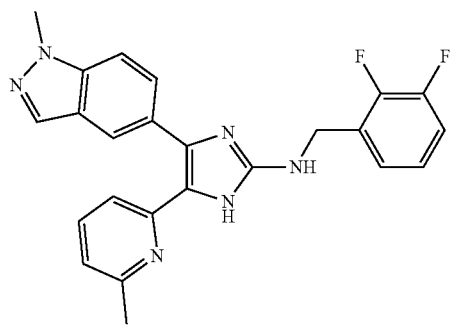 [SMILES: Cc1cccc(-c2[nH]c(NCc3cccc(F)c3F)nc2-c2ccc3c(cnn3C)c2)n1] | B |
| 36 | 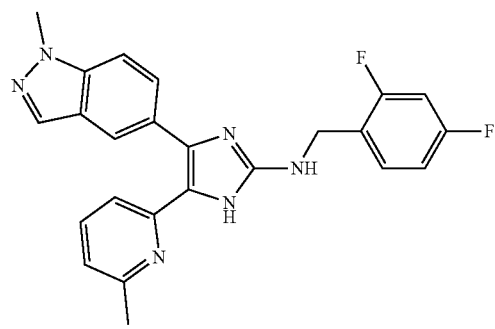 [SMILES: Cc1cccc(-c2[nH]c(NCc3ccc(F)cc3F)nc2-c2ccc3c(cnn3C)c2)n1] | B |
| 37 | 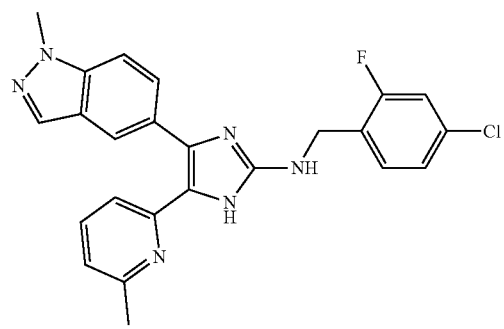 [SMILES: Cc1cccc(-c2[nH]c(NCc3ccc(Cl)cc3F)nc2-c2ccc3c(cnn3C)c2)n1] | B |
| 38 | 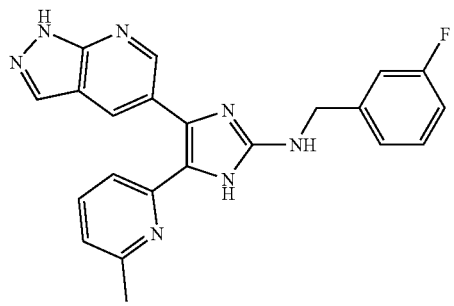 [SMILES: Cc1cccc(-c2[nH]c(NCc3cccc(F)c3)nc2-c2cnc3[nH]ncc3c2)n1] | B |

| Example | Structure | Assay |
|---|---|---|
| 39 | 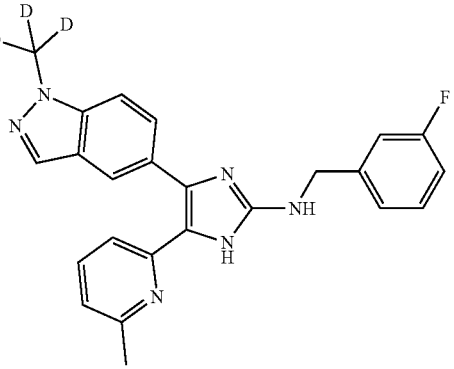 | A |

The invention claimed is:

1. A compound of formula I or a pharmaceutically acceptable salt, solvate, polymorph, ester, or tautomer thereof;

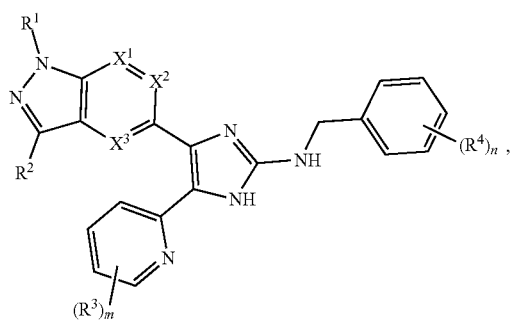

wherein;
$R^1$ is independently selected from the group consisting of H, C1-C6 alkyl, $CD_3$, $CHF_2$, $CF_3$, —(C1-C6) hydroxyalkyl, and —$SO_2$alkyl;
$R^2$ is independently selected from the group consisting of H, Me, $CF_3$, $NO_2$, halogen, C1-C6alkyl, substituted $C_1$-C6alkyl, C1-C6haloalkyl, C3-C7cycloalkyl, alkylcarboxy, cyano, and alkoxy;
$X^1$, $X^2$ and $X^3$ are each independently CH or N;
each $R^3$ is independently selected from the group consisting of hydrogen, halogen, $CF_3$, amino, substituted amino, C1-C6alkyl, substituted C1-C6alkyl, C1-C6haloalkyl, C3-C7cycloalkyl, alkylcarboxy, cyano, nitro, and alkoxy;
each $R^4$ is independently selected from the group consisting of hydrogen, halogen, $CF_3$, amino, substituted amino, C1-C6alkyl, substituted C1-C6alkyl, C1-C6haloalkyl, cyano, nitro, alkoxy, and aryloxy;
m is 1, 2, 3 or 4; and
n is 1, 2, 3, 4 or 5.

2. The compound of claim 1 or the pharmaceutically acceptable salt, solvate, polymorph, ester, or tautomer thereof, wherein the compound is of Formula II:

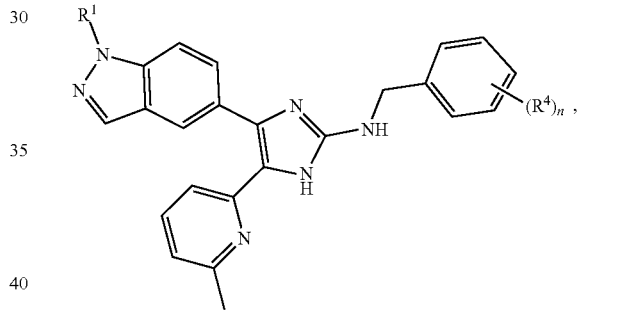

wherein;
$R^1$ is independently selected from the group consisting of H, C1-C6 alkyl, $CD_3$, $CHF_2$, $CF_3$, —(C1-C6) hydroxyalkyl, and —$SO_2$alkyl;
each $R^4$ is independently selected from the group consisting of hydrogen, halogen, $CF_3$, amino, substituted amino, C1-C6alkyl, substituted C1-C6alkyl, C1-C6haloalkyl, cyano, nitro, alkoxy, and aryloxy; and
n is 1, 2, 3, 4 or 5.

3. A pharmaceutical composition comprising a pharmaceutically effective amount of the compound of claim 1 or the pharmaceutically acceptable salt, solvate, polymorph, ester, or tautomer thereof, and a pharmaceutically acceptable carrier.

* * * * *